(12) United States Patent
Russell et al.

(10) Patent No.: US 9,920,320 B2
(45) Date of Patent: Mar. 20, 2018

(54) METHODS OF MODULATING COMPLIANCE OF THE TRABECULAR MESHWORK

(71) Applicant: The Regents of the University of California, Oakland, CA (US)

(72) Inventors: Paul Russell, Davis, CA (US); Christopher J. Murphy, Davis, CA (US); Sara M. Thomasy, Sacramento, CA (US); Vijay Krishna Raghunathan, Davis, CA (US); Joshua T. Morgan, Davis, CA (US); Joshua Wood, Vacaville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/960,310

(22) Filed: Dec. 4, 2015

(65) Prior Publication Data

US 2016/0215285 A1 Jul. 28, 2016

Related U.S. Application Data

(63) Continuation of application No. 14/134,991, filed on Dec. 19, 2013, now Pat. No. 9,206,423.

(60) Provisional application No. 61/747,352, filed on Dec. 30, 2012.

(51) Int. Cl.
| | |
|---|---|
| *A61K 31/70* | (2006.01) |
| *C12N 5/00* | (2006.01) |
| *C12N 15/113* | (2010.01) |
| *C07D 493/06* | (2006.01) |
| *A61K 31/7088* | (2006.01) |
| *A61K 31/713* | (2006.01) |
| *A61K 9/00* | (2006.01) |
| *A61K 45/06* | (2006.01) |

(52) U.S. Cl.
CPC .......... *C12N 15/113* (2013.01); *A61K 9/0048* (2013.01); *A61K 31/7088* (2013.01); *A61K 31/713* (2013.01); *A61K 45/06* (2013.01); *C07D 493/06* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 9,206,423 B2 | 12/2015 | Russell et al. | |
| 2004/0259247 A1* | 12/2004 | Tuschl | A61K 48/00 435/375 |
| 2011/0027186 A1 | 2/2011 | Hong et al. | |
| 2012/0063994 A1 | 3/2012 | Stout et al. | |
| 2014/0187607 A1 | 7/2014 | Russell et al. | |
| 2014/0235678 A1* | 8/2014 | Bottger | A61K 9/0048 514/350 |
| 2015/0157584 A1 | 6/2015 | Guan et al. | |
| 2016/0222385 A1* | 8/2016 | Shen | C12N 15/113 |

OTHER PUBLICATIONS

Clinical Trials.gov https://clinicaltrials.gov/ct2/show/NCT01348126, May 2, 2011.*
Chittenden et al., Genes Dev. vol. 26(12):1300-1305, Jun. 15, 2012.*
Chee et al., (Clinical Genitourinary Cancer vol. 5(7):433-437.*
Roesener et al., (J. Am. Chem. Soc. vol. 108:846-847, 1986.*
Menezes et al. Mol. Cancer Ther. vol. 11(3):730-739, Jun. 13, 2012, published Online Jan. 12, 2012.*
U.S. Notice of Allowance dated Aug. 24, 2015 issued in U.S. Appl. No. 14/134,991.
Chen, et al. , "Verteporfin without light stimulation inhibits YAP activation in trabecular meshwork cells: Implications for glaucoma treatment." Biochemical and Biophysical Research Communications 466:221-225, 2015.
Dupont, et al. "Role of YAP/TAZ in mechanotransduction." Nature 474:179-185, Jun. 9, 2011.
Ly, et al., "YAP translocation in human trabecular meshwork cells." Poster and Abstract #2310, presented at Meeting of American Society for Cell Biology, Dec. 15-19, 2012.
Morgan, et al., "Correlation of cross-linked actin network formation and elastic moduli of human trabecular meshwork cells," Poster and Abstract #1055, presented at Meeting of American Society for Cell Biology, Dec. 15-19, 2012.
Raghunathan, et al., "Substratum topography alters YAP-mediated mechnotransduction response in corneal epithelial cells." Abstract #2120, presented at Meeting of American Society for Cell Biology, Dec. 15-19, 2012.
Raghunathan, et al., "Mechanotransduction response in corneal cells is mediated by the YAP pathway," Poster, presented at Meeting of American Society for Cell Biology, Dec. 15-19, 2012.
Raghunathan, et al. 2013, "Role of Substratum Stiffness in Modulating Genes Associated with Extracellular Matrix and Mechanotransducers YAP and TAZ," *IOVS* 54(1):378-386.
Raghunathan, et al. 2014, "Involvement of YAP, TAZ and HSP90 in Contact Guidance and Intercellular Junction Formation in Corneal Epithelial Cells," *PLOS ONE* 9(10):1-14.
Russell, et al., "Mechanotransduction in Trabecular Meshwork Cells and the Progression of Glaucoma," Abstract #O048, presented at Meeting of International Society of Eye Research, Jul. 21-25, 2012.
Russell, et al., "Mechanotransduction in Trabecular Meshwork Cells and the Progression of Glaucoma," Poster and Abstract #2122, presented at Meeting of American Society for Cell Biology, Dec. 15-19, 2012.

(Continued)

*Primary Examiner* — Sean McGarry
(74) *Attorney, Agent, or Firm* — Weaver Austin Villeneuve & Sampson LLP

(57) ABSTRACT

The present invention relates to method, system, and composition for modulating the compliance of the trabecular meshwork, which may provide treatment to glaucoma.

5 Claims, 23 Drawing Sheets

(56) References Cited

OTHER PUBLICATIONS

Thomasy, et al. 2012, "Substratum Compliance and Latrunculin B Regulate the Gene Expression of YAP/TAZ in Human Trabecular Meshwork Cells." Abstract #2121, presented at Meeting of American Society for Cell Biology, Dec. 15-19, 2012.
Thomasy, et al. 2013, "Substratum stiffness and latrunculin B modulate the gene expression of the mechanotransducers YAP and TAZ in human trabecular meshwork cells," *Experimental Eye Research* 113:66-73.
Wood, et al., "Biophysical Cues and Dexamethasone Modulate YAP/TAZ Expression in Human Trabecular Meshwork Cells," Presentation Abstract and Poster #3269/A114, presented at Meeting of Association for Research in Vison and Ophthalmology, May 6-9, 2012.
Derwent, et al., "Thermoresponsive Hydrogels as a New Ocular Drug Delivery Platform to the Posterior Segment of the Eye" *Trans Am Ophthalmol Soc*, 106:206-214, 2008.
Gao, et al., "A Microparticle/Hydrogel Combination Drug-Delivery System for Sustained Release of Retinoids" *IOVS*, 53(10):6314-6323, 2012.
Liu, et al., "Nanomaterials for ocular drug delivery." *Macromol Biosci*. May 2012;12(5):608-20. Abstract only.
Stanzel, et al., "Subretinal Delivery of Ultrathin Rigid-Elastic Cell Carriers Using a Metallic Shooter Instrument and Biodegradable Hydrogel Encapsulation" *IOVS*, 53(1):490-500, 2012.
Wang, et al., "Extended release of bevacizumab by thermosensitive biodegradable and biocompatible hydrogel." *Biomacromolecules*. Jan 9, 2012;13(1):40-8. Abstract only.

\* cited by examiner

METHODS OF MODULATING COMPLIANCE OF THE TRABECULAR MESHWORK

CROSS-REFERENCE TO RELATED APPLICATIONS

This application is a continuation of U.S. application Ser. No. 14/134,991, filed on Dec. 19, 2013, issued on Dec. 8, 2015 as U.S. Pat. No. 9,206,423, which claims the benefit under 35 U.S.C. § 119(e) of U.S. Provisional Application No. 61/747,352, filed on Dec. 30, 2012, which is hereby incorporated herein by reference for all purposes.

STATEMENT OF GOVERNMENTAL SUPPORT

This invention was made with government support under Grant Nos. R01EY019475, R01EY019970 and P30EY12576, awarded by National Institutes of Health. The government has certain rights in the invention.

FIELD OF INVENTION

The present invention relates to method, system, and composition for modulating the compliance of the trabecular meshwork, which may provide treatment to glaucoma.

BACKGROUND

Glaucoma is a devastating condition associated with irreversible degeneration of the optic nerve head, which can lead to blindness. Although the exact mechanisms contributing to the initiation and progression of most glaucomas are unknown, the primary risk factor is increased intraocular pressure (IOP) (Rhee et al., 2009). IOP is presumably elevated from an abnormal increase in resistance to aqueous outflow within the human trabecular meshwork (HTM) and adjacent Schlemm's canal cells (Last et al., 2011; McKee et al., 2011; Rhee et al., 2009). The HTM is a mechanosensitive structure that is subjected to dynamic strain from changes in intraocular pressure as well as from the ciliary muscle and intrinsic contractile elements (Bradley et al., 2001; Tumminia et al., 1998; Wiederholt et al., 2000). It is comprised of extracellular matrix (ECM) which possesses an intrinsic compliance and complex three-dimensional topography that support and interact with the overlying TM cells. Recently, Last et al. demonstrated that the HTM is stiffer with glaucoma and this change may influence the outflow facility of aqueous humor (Last et al., 2011). In vivo, HTM cells are exposed to dynamic, compliant substrates that markedly differ from flat, rigid substrates such as glass or tissue culture polystyrene (TCP) which are typically used to investigate cellular behavior. Substratum stiffness has been shown to profoundly alter HTM cytoskeletal structure and dynamics, cell stiffness, ECM gene and protein expression patterns, cell behaviors, and the cellular response to therapeutic agents (Han et al., 2011; McKee et al., 2011; Schlunck et al., 2008; Thomasy et al., 2012; Wood et al., 2011a).

While substratum elastic modulus has been shown to modulate a variety of HTM cellular behaviors, the intrinsic mechanisms by which HTM cells perceive biomechanical cues and translate these external stimuli to intracellular signals that control cell behavior and gene transcription remain unknown. A recent study by Dupont et al. identified the Yorkie homologues YAP (Yes-associated protein) and TAZ (transcriptional coactivator with PDZ-binding motif; encoded by WWTR1), as the nuclear relays of mechanical signals exerted by ECM rigidity (Dupont et al., 2011). YAP and/or TAZ are co-activators of transcription and their specific functions are dependent on their spatial localization within the cellular nucleus or cytoplasm (FIG. 1) (Dupont et al., 2011; Zhao et al., 2010a). When localized to the nucleus, YAP and/or TAZ regulates the activity of multiple transcription factors. YAP and TAZ can be phosphorylated by the large tumor suppressor (LATS) 1/2, triggering cytoplasmic retention and loss of transcriptional activity (Zhao et al., 2010a). Once phosphorylated, YAP and TAZ bind with 14-3-3σ and can be targeted for degradation. If there is a decrease in phosphorylation of YAP and/or TAZ, more nuclear localization is possible. In addition, it has been shown that cells cultured on stiffer substrates have increased nuclear localization of YAP and/or TAZ (Dupont et al., 2011).

SUMMARY

Provided herein are methods for reducing intraocular pressure and/or treating symptoms and progression associated with glaucoma. The present invention treats glaucoma by directly targeting the human trabecular meshwork (HTM). More specifically, the present invention provides methods for modulating (e.g., increasing or decreasing) the compliance of trabecular meshwork (TM) tissue, including individual cells and/or the extracellular matrix (ECM) of the TM. The invention is consistent with the rationale that by keeping YAP and/or TAZ in the cytoplasm or modulating the expression and or breakdown of these proteins, the progression of glaucoma would be slowed. Furthermore, the invention is consistent with the finding that HTM substratum stiffness modulates the YAP and/or TAZ pathway and extracellular matrix (ECM) genes in HTM cells, which can affect the onset and progression of glaucoma.

Accordingly, in one aspect, provided are methods of reducing intraocular pressure. In some embodiments, the methods comprising administering to a subject an effective amount of an agent that modulates or alters (e.g., inhibits) the function of Yes-associated protein and/or transcriptional co-activator with PDZ binding motif (TAZ), thereby reducing intraocular pressure in the subject.

In another aspect, provided are methods of mitigating, reducing the severity of and/or preventing one or more symptoms associated with glaucoma. In some embodiment, the methods comprise administering to the subject an effective amount of an agent that modulates or alters (e.g., inhibits) the function of YAP and/or TAZ, thereby mitigating, reducing the severity of and/or preventing one or more symptoms associated with glaucoma in the subject.

In a related aspect, provided are methods of mitigating, delaying, reducing and/or preventing the progression of glaucoma. In some embodiments, the methods comprise administering to a subject an effective amount of an agent that modulates or alters (e.g., inhibits) the function of YAP and/or TAZ, thereby mitigating, delaying, reducing and/or preventing the progression of glaucoma in the subject.

One aspect relates to a composition comprising an agent that modulates or alters (e.g., inhibits) the function of YAP and/or TAZ formulated for ophthalmic administration.

In varying embodiments, the agent administered to the subject is administered intraocularly. In some embodiments, the agent is administered directly to the trabecular meshwork. In other embodiments the agent is administered topically. In alternative embodiments, the agent is administered systemically. In various embodiments, the subject is glaucomatous.

In varying embodiments, the agent modulates or alters (e.g., inhibits) the expression of YAP and/or TAZ. In some embodiments, the agent is an inhibitory nucleic acid that hybridizes to and modulates or alters (e.g., inhibits) the transcription and/or translation of YAP and/or TAZ. Exemplary inhibitory nucleic acids include without limitation short interfering RNAs (siRNAs), short-hairpin RNAs (shRNAs) or micro RNAs (miRNAs). For instance, in one embodiment, the inhibitory nucleic acid is miRNA-375 (e.g., Gene ID: 494324; GenBank Ref. Nos. NC_000002.11, 1.NC_018913.1 and/or 1.AC_000134.1), or a nucleic acid having at least 90%, 91%, 92%, 93%, 94%, 95%, 96%, 97%, 98%, 99% or 100% sequence identity to miRNA-375.

In some embodiments, the agent inhibits, reduces and/or prevents the translocation to the nucleus of YAP and/or TAZ. In some embodiments, the agent alters the transcriptional behavior of YAP and/or TAZ.

In some embodiments, the agent is a small organic compound. Illustrative compounds include, without limitation, e.g., dobutamine (CAS #34368-04-2), HSP90 inhibiting geldanamycin analogue 17-DMAG (CAS #467214-21-7), HSP90 inhibiting geldanamycin analogue 17-AAG (CAS #75747-14-7), HSP90 inhibitor STA-9090 (CAS #888216-25-9), HSP90 inhibitor NVP-HSP990 (CAS #934343-74-5) porphyrin family member verteporfin (CAS #129497-78-5), porphyrin family member protoporphyrin IX (CAS #553-12-8), and mixtures and analogs thereof.

In some embodiments, in addition to administering the agent that inhibits the function of YAP and/or TAZ, the methods further comprise co-administering an anti-LPA agent that reduces, inhibits or prevents the production of lysophosphatidic acid (LPA). In some embodiments, the anti-LPA agent is selected from the group consisting of Ki16425 (CAS 355025-24-0), S32826 (CAS #1096770-84-1), PF-8380 (CAS #1144035-53-9); an agent that inhibits production of serum derived sphinghosine-1-phosphate (S1P), or dihydroS1P, e.g., sphingosine kinase-1 inhibitor PF-543; an agent that inhibits the activity of Akt, e.g., such as Akt inhibitor X (CAS #925681-41-0), MK-2206 2HCl (CAS #1032350-13-2, 1032349-93-1 (free base), 1032349-77-1 (HCl)), Perifosine (CAS #157716-52-4), and mixtures and analogs thereof.

In some embodiments, in addition to administering an agent that modulates or alters (e.g., inhibits) the function of YAP and/or TAZ, the methods further comprise co-administering one or more agents that disrupt the cytoskeleton of a trabecular meshwork cell.

In some embodiments, the anti-cytoskeleton agents comprise an agent that disrupts intermediate filaments. Non-limiting examples include acrylamide.

In varying embodiments, the anti-cytoskeleton agents comprise an agent that disrupts microtubules. Non-limiting examples include colchicine, colecemid, vinca alkaloids (e.g., vinblastine, vincristine, vinorelbine, vindesine), podophyllotoxin, capecotobine, nocodazole, tryprostatin A, rhizoxin, vinflunine, epothilones, ixabepilone, methyl benzimidazol-2-yl-carbamate, estramustine sodium phosphate, taxanes (e.g., paclitaxel, docetaxil, colchitaxel), and indibulin.

In varying embodiments, the anti-cytoskeleton agents comprise an agent that disrupts actin polymerization. Non-limiting examples include Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, latrunculin A, latrunculin B, Swinholide A, Misakinolide A, Bistheonelide A, Scytophycin A, Scytophycin B, Scytophycin D, Scytophycin E, 19-0-Demethylscytophycin C, 6 Hydroxyscytophycin B, 6-Hydroxy-7-o-methylscytophycin E, tolytoxin, Mycalolide A, Mycalolide B, Mycalolide C, secomycalolide A and 30-hydroxymycalolide A, Halichondramide, (19Z)-halichondramide, kabiramides B, kabiramides C, kabiramides D, kabiramides G, kabiramides J, kabiramides K, ulapualide A, jaspamide, Dihydrohalichondramide, Aplyronine A, Aplyronine B, Aplyronine C, Pectenotoxin 2, Pectenotoxin 6, Migrastatin, cucurbitane-type tritepenes B&E, olivetoric acid, chivosazole A, chivosazole F, desmethoxymajusculamide C, rho kinase inhibitors, blebbistatin, and mixtures and analogs thereof.

Definitions

The "Yes-associated protein (YAP) transcriptional co-activator" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a YAP nucleic acid (see, e.g., GenBank Accession No. NM_001130145.2→NP_001123617.1 yorkie homolog isoform 1; NM_006106.4→NP_006097.2 yorkie homolog isoform 2; NM_001195044.1→NP_001181973.1 yorkie homolog isoform 3; 3.NM_001195045.1→NP_001181974.1 yorkie homolog isoform 4); (2) bind to antibodies, e.g., polyclonal antibodies, raised against an immunogen comprising an amino acid sequence of a YAP polypeptide; or an amino acid sequence encoded by a YAP nucleic acid, and conservatively modified variants thereof; (3) specifically hybridize under stringent hybridization conditions to an anti-sense strand corresponding to a nucleic acid sequence encoding a YAP protein, and conservatively modified variants thereof; and/or (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a YAP nucleic acid (e.g., described above). Based on the knowledge of YAP homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the YAP protein. YAP is the human ortholog of chicken YAP protein which binds to the SH3 domain of the Yes proto-oncogene product. This protein contains a WW domain that is found in various structural, regulatory and signaling molecules in yeast, nematode, and mammals, and may be involved in protein-protein interaction. As discussed above, functionally, YAP is a transcriptional co-activator and a major downstream effector of the Hippo pathway (Dong et al., 2007). LATS1/2 inhibit YAP by direct phosphorylation, which results in YAP binding to 14-3-3σ and cytoplasmic sequestration (Dong et al., 2007; Hao et al., 2008; Zhao et al., 2007). The unphosphorylated YAP localizes in the nucleus and acts mainly through TEAD family transcription factors to stimulate expression of genes that promote proliferation and inhibit apoptosis (Zhao et al., 2008). Phosphorylation of YAP by Lats1/2 kinases can also promote its ubiquitination-dependent degradation (Zhao et al., 2010b).

The terms "WW domain containing transcription regulator 1 (WWTR1)" and "transcriptional coactivator with PDZ binding motif (TAZ)" refers to a YAP paralog in mammals and is also regulated by the Hippo pathway through both cytoplasmic retention and proteasome degradation (Lei et al., 2008). TAZ is a WW domain containing a transcriptional coactivator that modulates mesenchymal differentiation and development of multiple organs. TAZ refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a TAZ nucleic acid (see, e.g., GenBank Accession Nos. NM_001168278.1→NP_001161750.1; 2.NM_001168280.1→NP_001161752.1; NM_015472.4→NP_056287.1; see also, Kanai, et al., The EMBO Journal (2000) 19(24):6778-6791); (2) bind to antibodies, e.g., polyclonal antibodies, raised against an immunogen comprising an amino acid sequence of a TAZ polypeptide; or an amino acid sequence encoded by a TAZ nucleic acid, and conservatively modified variants thereof; (3) specifically hybridize under stringent hybridization conditions to an anti-sense strand corresponding to a nucleic acid sequence encoding a TAZ protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a TAZ nucleic acid (e.g., described above). Based on the knowledge of TAZ homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the TAZ protein.

The term "homeomimetic" refers to substrates that have compliance or stiffness values that approximate the normal HTM (~5 kiloPascals (kPa)). The term "pathomimetic" refer to substrates having compliance or stiffness values that approximate the glaucomatous HTM (~75 kPa).

The terms "stiffness" or "compliance" interchangeably refer to the property of a body or substance of yielding to an applied force or of allowing a change to be made in its shape; also, the degree of yielding, measured by the displacement produced by a unit change in the force. Compliance or stiffness can be quantified by elastic modulus or Young's modulus, in units of kPa.

The term "specifically inhibit" refers to the ability of an agent or ligand to inhibit the expression (e.g., transcription and/or translation) or the biological function of a target protein. Specific inhibition typically results in at least about a 2-fold inhibition over background, preferably greater than about 10 fold and most preferably greater than 100-fold inhibition of expression (e.g., transcription or translation) of the target protein or measured biological function, for example, by comparing treated and untreated cells, or a cell population before and after treatment. In some embodiments, the expression or biological function of the target protein is completely inhibited. Typically, specific inhibition is a statistically meaningful reduction in expression or biological function (e.g., p≤0.05) using an appropriate statistical test.

The terms "bind(s) specifically" or "specifically bind(s)" or "attached" or "attaching" refers to the preferential association of an agent or ligand, in whole or part, with a target epitope that binds or competes with another agent or ligand for binding to the target epitope expressed on a cell or tissue. It is, of course, recognized that a certain degree of non-specific interaction may occur between an antibody and a non-target epitope. Nevertheless, specific binding, can be distinguished as mediated through specific recognition of the target epitope. Typically specific binding results in a much stronger association between the delivered molecule and an entity (e.g., an assay well or a cell) bearing the target epitope than between the bound antibody and an entity (e.g., an assay well or a cell) lacking the target epitope. Specific binding typically results in at least about a 2-fold increase over background, preferably greater than about 10-fold and most preferably greater than 100-fold increase in amount of bound agent or ligand (per unit time) to a cell or tissue bearing the target epitope as compared to a cell or tissue lacking the target epitope. Specific binding between two entities generally means an affinity of at least $10^6$ $M^{-1}$. Affinities greater than $10^8$ $M^{-1}$ or greater are preferred. Specific binding can be determined for nucleic acid as well as protein agents and ligands. Specific binding for nucleic acid agents can be determined using any assay known in the art, including but not limited to northern blots, gel shift assays and in situ hybridization. Specific binding for protein agents and ligands can be determined using any binding assay known in the art, including but not limited to gel electrophoresis, Western blot, ELISA, flow cytometry, and immunohistochemistry.

The term "agent" as used herein refers to polypeptides (e.g., ligands, antibodies), peptidomimetics, nucleic acids, small organic compounds, and the like.

The term "inhibitory nucleic acid" refers to a single-stranded nucleic acid that specifically binds or hybridizes to a complementary nucleic acid to inhibit or decrease gene expression of the complementary nucleic acid. Illustrative inhibitory nucleic acids suitable for use with the present invention include small interfering RNA ("siRNA" or "RNAi"), short hairpin RNA (shRNA), micro RNA ("miRNA"), antisense, ribozymes, and the like.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

The terms "decrease," "inhibit" and/or "reduce" is generally made with reference to a predetermined threshold level or a level of expression (e.g., transcription and/or translation) from a diseased or glaucomatous control. A decreased, reduced and/or inhibited expression level is determined when the level of expression in the test biological sample is at least about 10%, 25%, 50%, 75%, 100% (i.e., 1-fold), 2-fold, 3-fold, 4-fold or less, in comparison to the predetermined threshold level of expression or the level of expression from a diseased or glaucomatous control tissue. In determining a decreased, reduced and/or inhibited level of expression, usually the same tissue types are compared.

"Topical application" to the eye refers to the administration of an agent to the eye by applying the agent to the eyelids or to the conjunctival sac in aqueous or viscous solutions or suspensions, in ointments, as fine powders, on cotton pledgets, by drug-impregnated contact lenses, by injection into the eye, by mechanical pumps, or by membrane release systems.

As used herein, "administering" refers to local and systemic administration, e.g., including enteral, parenteral, pulmonary, and topical/transdermal administration. Routes of administration for compounds (e.g., one or more inhibitors of YAP and/or TAZ) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a non-human animal (e.g., mammal or avian) so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administer" refers to the simultaneous presence of two active agents in the blood of an individual. Active agents that are co-administered can be concurrently or sequentially delivered.

The term "therapeutically effective amount" refers to an amount of the compound being administered sufficient to prevent or decrease the development of one or more of the symptoms of the disease, condition or disorder being treated. Preferably, a therapeutically effective amount achieves efficacy with minimal or no undesirable side effects.

As used herein, the terms "treating" and "treatment" refer to delaying the onset of, retarding or reversing the progress of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease (e.g., glaucoma and/or elevated intraocular pressure).

The terms "subject," "patient," or "individual" interchangeably refer to a mammal, in particular, a human or a non-human primate. In some embodiments, the mammal is a domesticated mammal (e.g., canine or feline), an agricultural mammal (e.g., porcine, ovine, bovine, equine) or laboratory mammal (e.g., murine, rattus, lagomorpha, hamster).

The terms "identical" or percent "identity," in the context of two or more nucleic acids or polypeptide sequences, refer to two or more sequences or subsequences that are the same. Sequences are "substantially identical" if they have a specified percentage of amino acid residues or nucleotides that are the same (i.e., at least 60% identity, optionally at least 65%, 70%, 75%, 80%, 85%, 90%, 95%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides for promoters that are substantially identical to any of the GenBank accession numbers described herein. Optionally, the identity exists over a region that is at least about 50 nucleotides or amino acids in length, or more preferably over a region that is 100 to 500 or 1000 or more nucleotides or amino acids in length, or over the full-length of the sequence.

The term "similarity," or "percent similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF DESCRIPTION OF THE DRAWINGS

To further clarify various aspects of some embodiments of the present invention, a more particular description will be rendered by reference to specific embodiments thereof which are illustrated in the appended drawings. It is appreciated that these drawings depict only typical embodiments and are therefore not to be considered limiting of its scope.

The invention will be described and explained with additional specificity and detail through the use of the accompanying drawings.

DETAILED DESCRIPTION

1. Introduction

Primary open-angle glaucoma (POAG) is characterized by increased resistance to aqueous humor outflow and a stiffer human trabecular meshwork (HTM). Two Yorkie homologues, YAP and TAZ are mechanotransducers of the extracellular-microenvironment and co-activators of transcription. One or more embodiments is in part based on the rationale that substratum stiffness modulates the YAP and/or TAZ pathway and extracellular matrix (ECM) genes in HTM cells, which affects the onset and progression of glaucoma. Specifically, the stiffer HTM associated with glaucoma result in nuclear localization of YAP and/or TAZ and a concomitant increase in gene expression of proteins upregulated by YAP such as TGM-2, CTGF and PAI-1.

Figure 1:
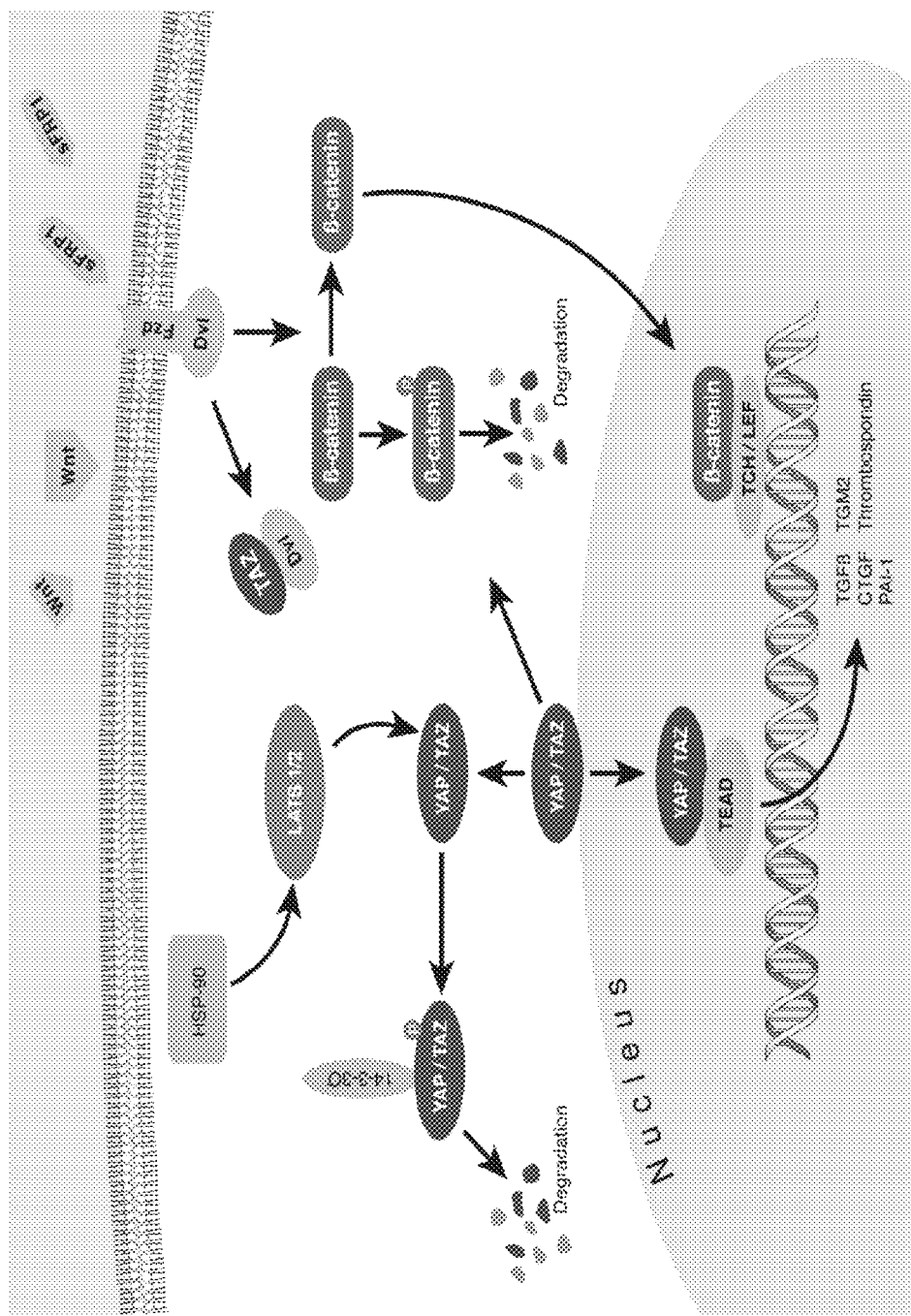
FIG. 1 illustrates a schematic map of the YAP and/or TAZ pathway. YAP and TAZ can be localized to either the nucleus or cytoplasm. In the nucleus, these proteins are co-activators of transcription that lead to the upregulation of genes relevant to glaucoma. In the cytoplasm, YAP and TAZ can be phosphorylated by LATS1 and 2 that are directly influenced by HSP90. Once phosphorylated, YAP and TAZ will bind with 14-3-3σ and be targeted for degradation. TAZ can also bind to the protein Dvl in the Wnt pathway. Once Dvl is bound, β-catenin can be phosphorylated and subsequently degraded instead of localizing to the nucleus. The YAP and TAZ association with Dvl antagonizes the Wnt pathway. Over-expression of an antagonist of the Wnt pathway (sFRP1) increases IOP in mice.

YAP1 and TAZ (YAP and/or TAZ) are proteins in the Hippo pathway that limits organ size as well as being involved in tumorgenesis (FIG. 1). However, the mechanotransduction by these proteins is currently thought to be outside the canonical Hippo pathway. There are multiple reports in the literature involving YAP1 due to its association in yeast with respect to oxidative stress; however, YAP1 does not have this function in mammalian cells. In the Hippo pathway, YAP and/or TAZ are enriched in the nuclear fraction under low cell density. When localized to the nucleus, these proteins regulate the activity of a number of transcription factors and YAP has been shown to upregulate at least 68 genes including TGF-β2, connective tissue growth factor (CTGF), serpine 1 (PAI-1), thrombospondin, and transglutaminase 2 (TGM2). The aforementioned genes have been shown to be upregulated with glaucoma or with glucocorticoid treatment of the HTM cells.

Although YAP and/or TAZ interact with a number of proteins, a recent report suggests one method of regulation to inhibit the nuclear action is through cytoplasmic HSP 90. HSP 90 stabilizes the kinases LATS1 and 2, which phosphorylate YAP and/or TAZ at positions 127 and 89 respectively. When phosphorylated on these residues, YAP and/or TAZ interact with the protein 14-3-3σ and subsequent phosphorylation leads to degradation of YAP and/or TAZ. If there is a decrease in phosphorylation of YAP and/or TAZ, more nuclear localization is possible. In addition, cytoplasmic TAZ has been shown to bind Smad complexes and shuttle them to the nucleus to bind TGF-β response elements. TAZ has also been reported to interact with zonula occulends-1 and 2 in a PDZ-1 dependent manner.

Another function of YAP and/or TAZ in the cytoplasm that can link these proteins to glaucoma involves the Wnt pathway. In the canonical pathway, Wnt binds the membrane receptor frizzled (Fzd). The cytoplasmic target of Fzd is a protein called disheveled (Dvl), which will suppress glycogen synthase kinase 3β. As a result, β-catenin is neither phosphorylated nor degraded and can translocate to the nucleus to activate other transcription factors. In glaucoma, there is an increased expression of the Wnt antagonist secreted frizzled-related protein-1 (sFRP-1) in the HTM and upregulation of this protein was linked to an increase in IOP by two fold. TAZ interacts with Dvl allowing β-catenin to be phosphorylated and eventually degraded. Thus, YAP and/or TAZ antagonize the Wnt pathway and can, like sFRP-1, be associated with an increase in IOP.

Latrunculin-B (Lat-B) is an actin cytoskeleton disruptor that is in human clinical trials for the treatment of glaucoma, and is targeted to the HTM. Cytoskeleton disruptors are thought to decrease IOP by decreasing the resistance to AH outflow through the HTM (Ethier et al., 2006; Kaufman, 2008; Okka et al., 2004; Rao et al., 2005; Rao et al., 2001). It has been reported that primary HTM cells adhered to stiffer substrates were significantly more responsive to Lat-B consistent with the conclusion that the effects of Lat-B treatment would be most pronounced in glaucomatous eyes with a stiffer HTM (McKee et al., 2011). This study also reported that there was a rebound effect on HTM cell stiffness as the actin cytoskeleton was reforming after the Lat-B treatment. Cells became stiffer following the Lat-B treatment than they were prior to the start of treatment. Cells then returned to their pretreatment values several hours subsequent to Lat-B removal.

We have demonstrated that substratum stiffness profoundly influenced gene and protein expression of several extracellular matrix proteins associated with glaucoma including myocilin and secreted protein, acidic, cysteine rich (SPARC) and modulated the impact of Lat-B treatment on the expression of these matrix proteins in primary HTM cells cultured for 24 hours on these substrates (Thomasy et al., 2012). This report also demonstrated that TGM-2, a gene known to be regulated by YAP (Dupont et al., 2011), was significantly decreased on substrates mimicking the stiffness of the normal HTM in comparison to TCP (Thomasy et al., 2012).

One or more embodiments utilize the relationship of substratum stiffness and Lat-B on the gene expression of the mechanotransducers YAP and TAZ as well as 14-3-3σ, connective tissue growth factor (CTGF), and plasma activator inhibitor-1 1 (PAI-1) in primary HTM cells during the initial recovery phase of the HTM cells after the Lat-B treatment (Browne et al., 2011; Dan et al., 2005; Ho et al., 2005; Junglas et al., 2012; Mossbock et al., 2008). During this time period, the stiffness of the HTM cells is only modestly altered from its normal values on the softer hydrogels. In contrast there is a dramatic difference on both the stiffer hydrogels and TCP, which transiently stiffen before relaxing to control values after several hours.

We have recently demonstrated the stiffness of the human meshwork increases twenty fold with glaucoma and the observed alteration in the biophysical property of the tissue correlates with increased outflow resistance. The underlying mechanism responsible for the changes in meshwork tissue stiffness has not been fully elucidated. Several molecules reported to be altered in the outflow pathway of glaucomatous patients could contribute to this stiffening of the meshwork. Transglutaminase has been reported to be increased in glaucoma, and this could lead to an increased percentage of cross-linked extracellular matrix (ECM) proteins and subsequent increased stiffness within the HTM. The stiffness of the glaucomatous meshwork may be elevated further by the decrease in matrix γ-carboxyglutamic acid protein, a calcification inhibitor. Consistent with this finding, an increase in alkaline phosphatase, a marker for calcification, had been reported in association with glaucoma. With the alterations in ECM stiffness, the ultrastructure of the glaucomatous meshwork is also changed. Glaucomatous eyes have elevated amounts of plaque-like material deposited in the JCT and an abundance of long spacing collagen. A correlation of the severity of optic nerve damage in glaucoma with changes in the HTM has been established indicating the progression of visual loss is linked to alterations in the TM.

2. Conditions Subject to Treatment

The present invention provides methods for reducing intraocular pressure and/or treating symptoms and progression associated with glaucoma. The present invention treats glaucoma by directly targeting the human trabecular meshwork (HTM). More specifically, the present invention provides methods for modulating (e.g. increase or decrease) the compliance of trabecular meshwork (TM) tissue, including individual cells and/or the extracellular matrix (ECM) of the TM.

The eye does not collapse because the pressure within the eye (the "intraocular pressure," or "IOP") is greater than that of the surrounding atmosphere. Normally, the IOP is between 10-20 mm Hg greater than the pressure of the atmosphere, although there is some modest daily fluctuation. IOP is created by the aqueous humor, a clear fluid that enters the anterior chamber of the eye via the ciliary body epithelium (inflow), flows through the anterior segment bathing the lens, iris, and cornea, and then leaves the eye via specialized tissues known as the trabecular meshwork (TM) and Schlemm's canal to flow into the venous system. Intraocular pressure is maintained by a balance between fluid secretion and fluid outflow. According to the NEI, most glaucomas result from a defect in the outflow and a subsequent buildup of pressure.

IOP is usually measured by determining the resistance of the eye to an external force. A variety of instruments are used to measure IOP clinically, including the Goldmann tonometer, which uses a prism to flatten the cornea, the Tono-Pen® XL applanation tonometer (Medtronic Xomed Ophthalmics, Inc., Jacksonville, Fla.), a hand-held device containing a plunger, and the Schiotz tonometer, which measures the indentation of the cornea produced by a weight.

Pharmacological agents that increase the compliance of TM tissue facilitate outflow of aqueous humor fluid through the TM, and therefore find use in the treatment (e.g., reversal or delay of progression) and prevention of eye disorders characterized by high intraocular pressures. Accordingly, patients who will benefit from administration of an agent that increases the compliance of TM tissue may present with intraocular pressure of greater than 20 mm Hg above ambient atmospheric pressure. The patient may have glaucoma and/or have been diagnosed by a clinician as having glaucoma.

In some embodiments, the patient has a normal IOP and is undergoing a therapeutic regime of another medication currently used to ameliorate symptoms of glaucoma. Independent of presenting IOP, the patient may be diagnosed as having glaucoma and under a therapeutic regime of an agent to treat glaucoma, e.g., a prostaglandin analog (e.g., latanoprost, bimatoprost, or travoprost); a topical beta-adrenergic receptor antagonist (e.g., timolol, levobunolol, and betaxolol); an alpha2-adrenergic agonist (e.g., brimonidine); a sympathomimetic (e.g., epinephrine, dipivefrin); a miotic agent (e.g., pilocarpine, ecothiopate); a carbonic anhydrase inhibitor (e.g., dorzolamide, brinzolamide, acetazolamide); or physostigmine. Other agents are described herein.

Individuals having increased IOP but who do not have clinically defined glaucoma can also benefit from administration of an agent that increases compliance of the TM.

3. Inhibitors of YAP and/or TAZ

Generally, the activity of proteins having, e.g., at least 80% sequence identity, e.g., at least about 85%, 90%, 91%, 92%, 93%, 94%, 95%, 96%, 97%, 98% or 99% sequence identity, to YAP (e.g., GenBank Accession No. NM_001130145.2→NP_001123617.1 yorkie homolog isoform 1; NM_006106.4→NP_006097.2 yorkie homolog isoform 2; NM_001195044.1→NP_001181973.1 yorkie homolog isoform 3; 3.NM_001195045.1→NP_001181974.1 yorkie homolog isoform 4) and/or TAZ (e.g., GenBank Accession Nos. NM_001168278.1→NP_001161750.1; 2.NM_001168280.1→NP_001161752.1; NM_015472.4→NP_056287.1; see also, Kanai, et al., The EMBO Journal (2000) 19(24):6778-6791) is inhibited or reduced.

YAP and/or TAZ activity can be inhibited at either or both of the protein and transcriptional levels. In various embodiments, an agent that inhibits the enzymatic or catalytic activity or substrate binding activity of a YAP and/or TAZ is administered. In some embodiments, an agent that inhibits the expression, e.g., the transcription and or translation of YAP and/or TAZ is administered. In other embodiments, an agent can affect the translocation of YAP and/or TAZ from the plasma to the nucleus of TM cells.

a. Pharmacological Agents

Modulating or altering (e.g., decreasing or inhibiting) YAP and/or TAZ function and/or expression (e.g., transcription and/or translation) can be achieved using any known method in the art. In some embodiments, the agent that alters (e.g., decreases and/or inhibits) YAP and/or TAZ function and/or expression comprise a small organic compound. Illustrative compounds include, without limitation, e.g., dobutamine (CAS #34368-04-2), HSP90 inhibiting geldanamycin analogue 17-DMAG (CAS #467214-21-7), HSP90 inhibiting geldanamycin analogue 17-AAG (CAS #75747-14-7), HSP90 inhibitor STA-9090 (CAS #888216-25-9), HSP90 inhibitor NVP-HSP990 (CAS #934343-74-5) porphyrin family member verteporfin (CAS #129497-78-5), porphyrin family member protoporphyrin IX (CAS #553-12-8), and mixtures and analogs thereof.

b. Inhibitory Nucleic Acids

Decreasing or inhibiting YAP and/or TAZ gene expression (e.g., transcription and/or translation) can also be achieved through the use of inhibitory nucleic acids (e.g., small interfering RNA (siRNA), micro RNA (miRNA), antisense RNA, ribozymes, etc.). Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. Such inhibitory nucleic acids can be in either the "sense" or "antisense" orientation. See, for example, Tafech, et al., Curr Med Chem (2006) 13:863-81; Mahato, et al., Expert Opin Drug Deliv (2005) 2:3-28; Scanlon, Curr Pharm Biotechnol (2004) 5:415-20; and Scherer and Rossi, Nat Biotechnol (2003) 21:1457-65.

In one embodiment, the inhibitory nucleic acid can specifically bind to a target nucleic acid sequence or subsequence that encodes a YAP protein. In another embodiment, the inhibitory nucleic acid can specifically bind to a target nucleic acid sequence or subsequence that encodes a TAZ protein. Administration of such inhibitory nucleic acids can decrease or inhibit the activity of YAP and/or TAZ and consequently, increase the compliance of HTM. Nucleotide sequences encoding a YAP and/or TAZ are known, see Genbank sequence listed in definitions above. From these nucleotide sequences, one can derive a suitable inhibitory nucleic acid.

Nucleic acids may be RNA or DNA or analogs or derivatives thereof. Nucleic acids may be double-stranded, single-stranded, linear, circular, synthetic, recombinantly produced, as well as altered nucleic acids that differ from naturally occurring RNA or DNA by the addition, deletion, substitution and/or alteration of one or more nucleotides. Such alterations can include addition of non-nucleotide material, such as to the end(s) of the nucleic acid or internally. Nucleotides in the nucleic acid molecules of the present invention can also comprise non-standard nucleotides, such as non-naturally occurring nucleotides or chemically synthesized nucleotides or deoxynucleotides, especially those that enhance the in vivo stability and/or pharmacokinetics of the nucleic acid molecules.

The inhibitory nucleic acid may be capable of giving rise directly to an inhibitory effect, subject to processing by cellular machinery where appropriate, or it may be in the form of a vector which expresses such a nucleic acid, e.g. a viral vector or plasmid. Viral vectors includes lentiviral vectors.

Typically, the inhibitory nucleic acid is an RNA interference agent (RNAi agent) or a nucleic acid vector that expresses or otherwise gives rise to an RNAi agent (e.g. a DNA-directed RNAi (ddRNAi) agent). RNA interference (RNAi) is a form of post-transcriptional gene silencing mediated by small non-coding RNA molecules of approximately 15 to 30 nucleotides in length. There are a wide range of RNA classes and pathways that can result in down-regulation of gene expression or gene silencing. In mammalian cells, RNAi can be triggered by 21-nucleotide (nt) duplexes of short interfering RNA or by micro-RNAs (miRNA), or other dsRNAs. Functional small-hairpin RNAs (shRNA) have an added stem-loop structure which is cleaved to form short interfering RNAs.

The inhibitory nucleic acid can be a polynucleotide with a duplex, asymmetric duplex, hairpin or asymmetric hairpin secondary structure, having self-complementary sense and antisense regions. The inhibitory nucleic acid may also be a circular single-stranded polynucleotide having two or more loop structures and a stem comprising self-complementary sense and antisense regions, wherein the circular polynucleotide can be processed either in vivo or in vitro to generate an active inhibitory nucleic acid molecule capable of mediating RNAi. The inhibitory nucleic acid can also be generated by cleavage of longer dsRNA with RNase III or Dicer. These enzymes process the dsRNA into biologically active siRNA (see, e.g., Yang et al., PNAS USA 99: 9942-7 (2002); Calegari et al., 2002, PNAS USA 99: 14236; Byrom et al., 2003, Ambion TechNotes 10(1): 4-6; Kawasaki et al., 2003, Nucleic Acids Res. 31: 981-7; Knight and Bass, 2001, Science 293: 2269-71; and Robertson et al., 1968, J. Biol. Chem. 243: 82).

In one embodiment, the inhibitory nucleic acid can be a double-stranded polynucleotide molecule comprising self-complementary sense and antisense regions. The inhibitory nucleic acid can be assembled from two separate oligonucleotides, where one strand is the sense strand and the other is the antisense strand.

Alternatively, the inhibitory nucleic acid may be assembled from a single oligonucleotide, where the self-complementary sense and antisense regions of the inhibitory nucleic acid are linked by means of a nucleic acid based or non-nucleic acid-based linker(s), e.g. shRNA. Inhibitory nucleic acids of the present invention may have one or more stem-loop structures where the ends of the double-stranded RNA are connected by a single-stranded, linker RNA. The length of the single-stranded loop portion of is typically from about 5 to 20 nucleotides in length, such as from about 5 to 11 nucleotides in length.

The double-stranded portions of inhibitory nucleic acid molecules may be completely homologous, or may contain non-paired portions due to sequence mismatch (the corresponding nucleotides on each strand are not complementary), bulge (lack of a corresponding complementary nucleotide on one strand), and the like. Such non-paired portions can be tolerated to the extent that they do not significantly interfere with duplex formation or efficacy.

RNAi agent-expressing vectors can be constructed based on, but not limited to, adeno-associated virus, retrovirus, adenovirus, alphavirus or lentivirus plasmid as well as other known vectors. The recombinant vectors capable of expressing the RNA molecules can be delivered to target cells. Such vectors can be repeatedly administered as necessary. Alternatively, certain RNA molecules can be expressed within cells from eukaryotic promoters.

i. Antisense Oligonucleotides

In some embodiments, the inhibitory nucleic acid is an antisense molecule. Antisense oligonucleotides are relatively short nucleic acids that are complementary (or antisense) to the coding strand (sense strand) of the mRNA target sequence. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a YAP or TAZ. Accordingly, antisense oligonucleotides decrease the expression and/or activity of YAP and/or TAZ.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810) or the blood-brain barrier (see, e.g., PCT Publication No. WO 89/10134), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide can be conjugated to another molecule.

The antisense oligonucleotide may comprise at least one modified base moiety which is selected from the group including but not limited to 5-fluorouracil, 5 bromouracil, 5-chlorouracil, 5-iodouracil, hypoxanthine, xanthine, 4-acetylcytosine, 5 (carboxyhydroxytriethyl)uracil, 5-carboxymethylaminomethyl-2-thiouridine, 5 carboxymethylaminomethyluracil, dihydrouracil, beta-D-galactosylqueosine, inosine, N6-isopentenyladenine, 1-methylguanine, 1-methylinosine, 2,2-dimethylguanine, 2 methyladenine, 2-methylguanine, 3-methylcytosine, 5-methylcytosine, N6-adenine, 7 methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an anomeric oligonucleotide. An anomeric oligonucleotide forms specific double-stranded hybrids with complementary RNA in which, contrary to the usual units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding YAP and/or TAZ, one of skill in the art can design antisense oligonucleotides that bind to a target nucleic acid sequence and test these oligonucleotides in an in vitro or in vivo system to confirm that they bind to and mediate the degradation of the mRNA encoding YAP and/or TAZ. To design an antisense oligonucleotide that specifically binds to and mediates the degradation of YAP and/or TAZ encoding nucleic acid, it is preferred that the sequence recognized by the oligonucleotide is unique or substantially unique to YAP and/or TAZ to be inhibited. For example, sequences that are frequently repeated across an encoding sequence may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for YAP and/or TAZ.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription and/or translation of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

ii. Small Interfering RNA (siRNA or RNAi)

In some embodiments, the inhibitory nucleic acid is a small interfering RNA (siRNA or RNAi) molecule. RNAi constructs comprise double stranded RNA that can specifically block expression of a target gene. "RNA interference" or "RNAi" is a term initially applied to a phenomenon where double-stranded RNA (dsRNA) blocks gene expression in a specific and post-transcriptional manner. RNAi provides a useful method of inhibiting gene expression in vitro or in vivo. RNAi constructs can include small interfering RNAs (siRNAs), hairpin RNAs, and other RNA species which can be cleaved in vivo to form siRNAs. RNAi constructs herein also include expression vectors ("RNAi expression vectors") capable of giving rise to transcripts which form dsRNAs or hairpin RNAs in cells, and/or transcripts which can produce siRNAs in vivo.

RNAi expression vectors express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell.

The RNAi constructs contain a nucleotide sequence that hybridizes under physiologic conditions of the cell to the nucleotide sequence of at least a portion of the mRNA transcript for the gene to be inhibited (i.e., YAP and/or TAZ encoding nucleic acid sequence). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity can be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, for example, 95%, 96%, 97%, 98%, 99%, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO 01/77350 describes an exemplary vector for bi-directional transcription and/or translation of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO 01/68836 and WO 01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

For purposes of reducing the activity of YAP and/or TAZ, siRNAs to the gene encoding YAP and/or TAZ can be specifically designed using computer programs.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA. Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence.

iii. Ribozymes

In some embodiments, the inhibitory nucleic acid is a ribozyme. Ribozymes molecules designed to catalytically cleave an mRNA transcripts can also be used to prevent translation of mRNA (See, e.g., PCT International Publication WO 90/11364; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; WO 88/04300; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

4. Formulation and Administration a. Formulation

The pharmacological agents that increase compliance of TM tissue can be prepared and administered in a wide variety of formulations for administration to the eyes. The formulations can be introduced onto or into the eye by, for example, applying the formulation to the eyelids or to the conjunctival sac in aqueous or viscous solutions or suspensions, in ointments, in small pellets, as fine powders, on cotton pledgets, by drug-impregnated contact lenses, by injection, by mechanical pumps, or by membrane release systems. In preferred forms, compounds for topical use in the methods of the present invention can be administered as eye drops, ointments, or small pellets to be placed under the eyelids. Accordingly, the methods permit administration of pharmaceutical compositions comprising a pharmaceutically acceptable carrier or excipient and a selected pharmacological agent, or combination thereof.

The pharmacological agents can be administered systemically (e.g., usually orally, but also intravenously, buccally, subcutaneously and via other systemic routes, as appropriate) or locally (e.g., topically, onto the eye directly or onto tissues around the eye; directly in and/or around the TM tissue; or intraocularly).

Administration of pharmacologically active agents to the eyes is well known, and considerable information is set forth in standard works, such as Zimmerman et al. (eds.), TEXTBOOK OF OCULAR PHARMACOLOGY, Lippincott Williams & Wilkins (1997); Jannus et al., (eds.), CLINICAL OCULAR PHARMACOLOGY, Butterworth-Heinemann (4th Ed., 2001), and Mauger and Craig, HAVENER'S OCULAR PHARMACOLOGY, Mosby-Year Book (6th Ed., 1994), Grosvenor, PRIMARY CARE OPTOMETRY, Butterworth-Heinemann, (4th Ed., 2001), Duvall and Kerschner, OPHTHALMIC MEDICATIONS AND PHARMACOLOGY, SLACK Inc., Thorofare, N.J. (1998), and Fechner and Teichmann, OCULAR THERAPEUTICS: PHARMACOLOGY AND CLINICAL APPLICATION, SLACK Inc., Thorofare, N.J. (1997). These well known techniques can be readily applied to prepare and administer agents that increase the compliance of TM tissue to persons in need thereof.

For preparing pharmaceutical compositions, pharmaceutically acceptable carriers can be either solid or liquid. The carriers may also act, for example, as diluents, binders, or preservatives.

Liquid form preparations include solutions, suspensions, and emulsions, for example, water or water/propylene glycol solutions. Other typical forms for administration of the agents, or combinations thereof are liquid paraffin, polyvinyl alcohol, povidine, carbomers, hypromellose, hydroxyethylcellulose, hydroxypropylcellulose, and carboxymethylcellulose.

Formulations for intravitreous injection are also known in the art. Intravitreal injection is typically performed in the outpatient setting using topical anesthesia and a small-bore needle (e.g., 27 or 30 gauge) to deliver the medication into the vitreous cavity of the eye via the pars plana portion of the globe. Typically, the agents, or combinations thereof are administered as a sterile, preservative-free aqueous solution, which may optionally contain sodium chloride, monobasic sodium phosphate monohydrate, dibasic sodium phosphate heptahydrate, hydrochloric acid, and/or sodium hydroxide and other agents to adjust the viscosity and pH.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as vials or ampoules.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of one or more agents is employed in reducing intraocular pressure, e.g., for slowing or reversing the progression of glaucoma. The dosage of the specific compound for treatment depends on many factors that are well known to those skilled in the art. They include for example, the route of administration and the potency of the particular compound.

In some aspects, the agent, or combinations thereof, is dissolved or suspended in a suitable solvent, such as water, ethanol, or saline, and administered as an aerosol of fine particles by breaking a fluid into fine droplets and dispersing them into a flowing stream of gas. Typically, such aerosols develop approximately 15 to 30 microliters of aerosol per liter of gas in finely divided droplets with volume or mass median diameters in the range of 2 to 4 micrometers. Predominantly, water or saline solutions are used with low solute concentrations, typically ranging from 1.0 to 5.0 mg/mL.

As noted, drugs may be applied to the eyelids or instilled in the conjunctival sac in aqueous or viscous solutions or suspensions, in ointments, as fine powders, on cotton pledgets, by drug-impregnated contact lenses, by injection, by mechanical pumps, or by membrane release systems. In contrast to systemic administration, the ocular concentration after topical administration is high. Dilution of the drug by tears, overflow onto the cheek, and excretion through the nasolacrimal system limit tissue concentration. Placing the drug beneath a contact lens, applying a cotton pledget, or applying a collagen shield saturated with the drug to the eye prolongs the contact and aids penetration.

b. Dosing and Scheduling

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein. Generally, an efficacious or effective amount of one or more agents is determined by first administering a low dose or small amount of the agent and then incrementally increasing the administered dose or dosages, and/or adding a second agent as needed, until a desired effect of inhibiting or preventing high intraocular pressures or symptoms of glaucoma is observed in the treated subject, with minimal or no toxic side effects. Applicable methods for determining an appropriate dose and dosing schedule for administration of a combination of the present invention are described, for example, in Brunton, et al., Goodman and Gilman's The Pharmacological Basis of Therapeutics, 12th Edition, McGraw-Hill Professional, 2010; in a Physicians' Desk Reference (PDR), 66th Edition, 2012; in Loyd, et al., Remington: The Science and Practice of Pharmacy, 22nd Edition, Pharmaceutical Press; in Martindale: The Complete Drug Reference, Sweetman, 2005, London: Pharmaceutical Press., and in Martindale, Martindale: The Extra Pharmacopoeia, 31st Edition., 1996, Amer. Pharmaceutical Assn, each of which are hereby incorporated herein by reference.

Dosage amount and interval can be adjusted individually to provide plasma or tissue levels of the agent sufficient to maintain a therapeutic effect. Single or multiple administrations of the compositions comprising an effective amount of one or more agents can be carried out with dose levels and pattern selected by the treating physician. The dose and administration schedule can be determined and adjusted based on the severity of the glaucoma or high intraocular pressure in the subject, which can be monitored throughout the course of treatment according to methods commonly practiced by clinicians or those described herein. In some embodiments, therapeutic levels will be achieved by administering single daily doses. In other embodiments, the dosing schedule can include multiple daily dose schedules. In still other embodiments, dosing every other day, semi-weekly, or weekly are included in the invention.

In embodiments where the agent is a polypeptide or an antibody, typical dosages can range from about 0.1 µg/kg body weight up to and including about 1 gm/kg body weight, preferably between about 1 µg/kg body weight to about 500 mg/kg body weight. More preferably, about 1, 2, 3, 4, 5, 10, 20, 30, 40, 50, 60, 70, 80, 90, or 100 mg/kg body weight.

In embodiments where the agent is a nucleic acid, typical dosages can range from about 0.1 mg/kg body weight up to and including about 100 mg/kg body weight, preferably between about 1 mg/kg body weight to about 50 mg/kg body weight. More preferably, about 1, 2, 3, 4, 5, 10, 15, 20, 30, 40 or 50 mg/kg body weight.

In embodiments were the agent is a small organic compound, typical dosages can range from about 0.1 µg/kg body weight up to and including about 1 g/kg body weight, preferably between about 1 µg/kg body weight to about 500 mg/kg body weight. More preferably, about 0.1, 1, 2, 3, 4, 5, 10, 20, 30, 40, 50, 60, 70, 80, 90, or 100 mg/kg body weight.

The exact dose will depend on a variety of factors as discussed supra, including the particular inhibitor, severity of the disease, and route of administration. Determining the exact therapeutically effective dose can be determined by a clinician without undue experimentation and can include any dose included within the ranges disclosed above.

In cases of local administration or selective uptake, the effective local concentration of the agent may not be related to plasma concentration. One having skill in the art will be able to optimize therapeutically effective local dosages without undue experimentation.

5. Screening for Inhibitors of YAP and/or TAZ

One can identify lead compounds that are suitable for further testing to identify those that are therapeutically effective inhibitory agents by screening a variety of compounds and mixtures of compounds for their ability to decrease or inhibit YAP and/or TAZ activity and/or reduce IOP and/or treat symptoms and progression of glaucoma as described herein.

The use of screening assays to discover naturally occurring compounds with desired activities is well known and has been widely used for many years. For instance, many compounds with antibiotic activity were originally identified using this approach. Examples of such compounds include monolactams and aminoglycoside antibiotics. Compounds which inhibit various enzyme activities have also been found by this technique, for example, mevinolin, lovastatin, and mevacor, which are inhibitors of hydroxymethylglutamyl Coenzyme A reductase, an enzyme involved in cholesterol synthesis. Antibiotics that inhibit glycosyltransferase activities, such as tunicamycin and streptovirudin have also been identified in this manner.

Thus, another important aspect of the present invention is directed to methods for screening samples for inhibition or reduction of YAP and/or TAZ activity. A "sample" as used herein can be any mixture of compounds suitable for testing in a YAP and/or TAZ assay. A typical sample comprises a mixture of synthetically produced compounds or alternatively a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like.

In the typical screening assay, a sample, for example a fungal broth, is added to a standard YAP and/or TAZ assay. If inhibition or enhancement of activity as compared to control assays is found, the mixture is usually fractionated to identify components of the sample providing the inhibiting or enhancing activity. The sample is fractionated using standard methods such as ion exchange chromatography, affinity chromatography, electrophoresis, ultrafiltration, HPLC and the like. See, e.g., Scopes, Protein Purification, Principles and Practice, 3rd Edition, 1994, Springer-Verlag. Each isolated fraction is then tested for inhibiting or enhancing activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure modulating agent as defined herein is an activity inhibiting or enhancing compound which migrates largely as a single band under standard electrophoretic conditions or largely as a single peak when monitored on a chromatographic column. More specifically, compositions of substantially pure modulating agents will comprise less than ten percent miscellaneous compounds.

In some embodiments, the assays are designed to screen large chemical libraries by automating the assay steps and providing compounds from any convenient source to assays, which are typically run in parallel (e.g., in microtiter formats on microtiter plates in robotic assays).

As noted, the invention provides in vitro assays for YAP and/or TAZ activity in a high throughput format. For each of the assay formats described, "no inhibitor" control reactions which do not include an inhibitory agent provide a background level of YAP and/or TAZ activity. In the high throughput assays, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay many different plates per day; assay screens for up to about 6,000-20,000, and even up to about 100,000-1,000,000 different compounds is possible using the integrated systems. The steps of labeling, addition of reagents, fluid changes, and detection are compatible with full automation, for instance using programmable robotic systems or "integrated systems" commercially available, for example, through BioTX Automation, Conroe, Tex.; Qiagen, Valencia, Calif.; Beckman Coulter, Fullerton, Calif.; and Caliper Life Sciences, Hopkinton, Mass.

In some assays it will be desirable to have positive controls to ensure that the components of the assays are working properly. For example, a known inhibitor of YAP and/or TAZ activity can be incubated with one sample of the assay, and the resulting increase or decrease in signal determined according to the methods herein.

Essentially any chemical compound can be screened as a potential inhibitor of YAP and/or TAZ activity in the assays. Most preferred are generally compounds that can be dissolved in aqueous or organic (especially DMSO-based) solutions and compounds which fall within Lipinski's "Rule of 5" criteria. The assays are designed to screen large chemical libraries by automating the assay steps and providing compounds from any convenient source to assays, which are typically run in parallel (e.g., in microtiter formats on multiwell plates in robotic assays). It will be appreciated that there are many suppliers of chemical compounds, including Sigma-Aldrich (St. Louis, Mo.); Fluka Chemika-Biochemica Analytika (Buchs Switzerland), as well as numerous providers of small organic molecule libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), Tripos, Inc. (St. Louis, Mo.), Reaction Biology Corp. (Malvern, Pa.), Biomol Intl. (Plymouth Meeting, Pa.), TimTec (Newark, Del.), and AnalytiCon (Potsdam, Germany), among others.

In one preferred embodiment, inhibitors of YAP and/or TAZ activity are identified by screening a combinatorial library containing a large number of potential therapeutic compounds (potential inhibitor compounds). Such "combinatorial chemical or peptide libraries" can be screened in one or more assays, as described herein, to identify those library members particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with beta-D-glucose scaffolding (Hirschmann et al., J. Amer. Chem. Soc. 114: 9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Ausubel and Sambrook, all supra), peptide nucleic acid libraries (see, e.g., U.S. Pat. No. 5,539,083), antibody libraries (see, e.g., Vaughn et al., Nature Biotechnology, 14(3): 309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.).

Lead compounds that have been identified for their capability to reduce or inhibit the activity of YAP and/or TAZ in vitro are then evaluated for their ability to lower IOP in in vivo and in vitro assays, as described herein, and/or to treat glaucoma in vivo. The ability of a particular compound to prevent, reduce or inhibit manifestations of disease in an animal model can be measured using any known technique. For example, test and control samples in in vitro assays and test and control animals in in vivo assays can be comparatively tested for disease signs, e.g., significantly elevated IOP.

6. Methods of Monitoring

In varying embodiment, monitoring methods entail determining a baseline value of intraocular pressure (IOP) in a patient before administering a dosage of YAP and/or TAZ inhibitor, and comparing this with a value IOP after administering a dosage of one or more YAP and/or TAZ inhibitor, respectively.

With respect to therapies using one or more YAP and/or TAZ inhibitors, a significant decrease (i.e., greater than the typical margin of experimental error in repeat measurements of the same sample, expressed as one standard deviation from the mean of such measurements) in value of IOP signals a positive treatment outcome (i.e., that administration of the one or more YAP and/or TAZ inhibitors has prevented, reduced, inhibited and/or mitigated high IOP in the subject). IOP can be determined using measures appropriate to the species.

In other methods, a control value of IOP is determined from a control population of individuals who have received a low dose of one or more YAP and/or TAZ inhibitors. Measured values of IOP in a patient are compared with the control value. If the measured level of IOP in the patient is not significantly different (e.g., more than one standard deviation) from the control value, treatment can be discontinued. If the measured level of IOP in the patient is significantly above the control value, continued or additional administration of the one or more YAP and/or TAZ inhibitors may be warranted.

Alternatively, the value measured in a patient can be compared with a control value (mean plus standard deviation) determined in a population of patients after receiving one or more YAP and/or TAZ inhibitors. Alternatively, the measured value in a patient can be compared with a control value in populations of prophylactically treated patients who were free of symptoms of glaucoma, or populations of therapeutically treated patients who show mitigation and/or amelioration of symptoms of glaucoma. If the measured level of IOP in the patient is significantly above the control value, continued or additional administration of the one or more YAP and/or TAZ inhibitors may be warranted.

EXAMPLES

The following examples are offered to illustrate, but not to limit the claimed invention.

Example 1

Substratum Stiffness Modulates Genes Associated with ECM, YAP and TAZ

Primary open-angle glaucoma (POAG) is characterized by increased resistance to aqueous humor outflow and a stiffer human trabecular meshwork (HTM). Two Yorkie homologues, YAP and TAZ are mechanotransducers of the extracellular-microenvironment and co-activators of transcription. This example explores how substratum stiffness modulates the YAP and/or TAZ pathway and extracellular matrix (ECM) genes in HTM cells.

Materials and Methods

Preparation of Substrates.

Polyacrylamide hydrogels mimicking the elastic modulus of normal (5 kPa) and glaucomatous (75 kPa) HTM were fabricated and characterized by atomic force microscopy as described previously (8-10). Briefly, the hydrogels were sterilized with ultraviolet light and rinsed thoroughly three times for 24 h each in Dulbecco's phosphate buffered saline (DPBS) to remove any toxic monomeric acrylamide and hydrate the hydrogels completely. The polymer hydrogels (20 mm diameter) were then allowed to adhere to tissue cultured plastic (TCP), stored in growth medium for 24 h, and coated with a proprietary mixture of fibronectin/collagen (FNC; Athena ES, Baltimore, Md.) prior to cell culture. Atomic force microscopy was used to validate the elastic modulus of the fully hydrated hydrogels, and the elastic modulus of the hydrogels used were 4±2 kPa and 71±5 kPa for 5 and 75 kPa, respectively (8, 11).

Isolation and Culture of Human Trabecular Meshwork Cells.

Primary human trabecular meshwork cells were isolated from donor corneoscleral rims (Heartland Lions Eye Bank, St. Louis, Mo.) as described previously (9, 11, 53). Cells isolated from 4 donors (designated as HTM631, HTM265, HTM211 and HTM516) were used in this study. Isolated cells were maintained in DMEM/F-12 with 2.5 mM L-glutamine (Thermo Scientific HyClone, Logan, Utah) supplemented with 10% fetal bovine serum (Atlanta Biologicals, Lawrence, Ga.) and 1% penicillin/streptomycin/amphotericin B (Lonza, Walkerville, Md.). Cells in passages 3-7 were used for all experiments. For RNA extraction, cells were seeded on FNC coated polyacrylamide hydrogel substrates, in 6 well dishes at $2\times10^5$ (75 kPa) or $3\times10^5$ (5 kPa) cells/well. For protein extraction, cells were seeded on FNC coated polyacrylamide hydrogels in 1 well plates (110 $cm^2$) at approximately $2\times10^6$ (75 kPa) or $3\times10^6$ (5 kPa) cells/plate. A higher density of cells were seeded on the 5 kPa hydrogels because HTM cells proliferate more slowly on softer versus stiffer substrates (9).

In addition, HTM cells were treated with DEX to investigate the influence of substratum stiffness on GC-stimulated HTM cells. HTM cells were treated with DEX. HTM cells, 24 h after plating, were treated with 10-7 M DEX in ethanol (EtOH) or the vehicle only (equivalent volume of EtOH, i.e., at a 1:1000 dilution). The media was changed after 3 days. Seven days after the first treatment, the cells were rinsed with DPBS, and RNA or protein was extracted.

RNA Isolation and Quantitative Real Time PCR.

RNA was isolated using the RNeasy kit (Qiagen, Valencia, Calif.) following the manufacturer's instructions and equal amounts were used for the quantitative real time PCR (qPCR) reactions. The qPCR was performed using a One-Step kit (TaqMan, Applied Biosystems, Carlsbad, Calif.) and commercially available primers for 18S (Hs99999901_s1), ANGPTL7 (Hs00221727_m1), CTGF (Hs00170014_m1), MYOC (Hs00165354_m1), sFRP1 (Hs00610060_m1), SFN (Hs00968567_s1), TGM2 (Hs01096681_m1), YAP (Hs00371735_m1), and WWTR1 (Hs00210007_m1) in total volumes of 10 µl per reaction (Applied Biosystems). The TAZ protein is encoded by the gene WWTR1; in this example both the mRNA and the protein encoded by the WWTR1 gene are termed TAZ. The reverse transcription reaction was performed in a StepOne qPCR machine (Applied Biosystems) with the following parameters: 30 minutes at 50° C. followed by 10 minutes at 95° C.; forty cycles of 60° C. for 1 minute followed by 95° C. for 15 seconds. Relative expression levels of the mRNAs of interest were normalized to the expression of the ribosomal RNA 18S. At least three reactions were run for each sample, and the experiments were performed for HTM cells from three individual donors. Gene expression was normalized relative to the expression of mRNA from HTM cells on homeomimetic (5 kPa) hydrogels treated with vehicle (EtOH), which was given a value of 1.0. In brief, equal amounts of RNA (60 ng) were loaded for all PCR reactions to account for variations in cell density. The $C_t$ values obtained represent logarithmic changes in gene expression. The difference in $C_t$ (i.e. $\Delta C_t$) between the gene of interest (e.g. YAP, TAZ etc.) and the calibrator gene (18S) were calculated. Next, the $\Delta C_t$ values between the 75 kPa data was normalized with the control (5 kPa, EtOH treated) data. Control data was normalized for each experiment and the logarithmic changes in gene expression were expressed as relative expression to the control data.

Gene Downregulation by siRNA Transfection.

At 60-80% confluence of HTM cells, siRNA transfections were performed using the DharmaFect 4 transfection reagent (Dharmacon, Lafayette, Colo.) following the manufacturer's instructions with final concentrations of 28.5 nM of YAP siRNA (Hs_YAP1_5) or control siRNA (ON-TARGETplus Non-targeting siRNA #3, Dharmacon). At 48 and 72 h post transfection, cells were harvested for RNA isolation. Knockdown to expression levels below 30% was achieved as determined by quantitative real time PCR (qPCR) analyses. The gene knockdown was done three times with cells from different donors.

Immunohistochemistry.

The corneoscleral rim from a 57 year old donor with no history of disease was fixed overnight in 10% neutral buffered formalin, paraffin embedded and sectioned. Sections were deparaffinized in Xylene, subjected to citrate antigen retrieval, peroxidase blocked, and incubated overnight at 4° C. with mouse anti-human YAP-H9 (Santa Cruz Biotechnologies, Santa Cruz, Calif.) and TAZ (Abnova, Walnut, Calif.) antibodies. Sections were then treated with horse anti-mouse biotinylated secondary antibody, followed by streptavidin-horseradish peroxidase, and developed with Vector Red chromogen prior to counterstaining with hematoxylin and coverslipping.

Protein Isolation and Western Blotting.

Cell monolayers cultured on polyacrylamide hydrogels were washed once in PBS and lysed and scraped into RIPA buffer (ThermoScientific, Waltham, Mass.) supplemented with protease and phosphatase inhibitors (Fisher Scientific, Hampton, N.H.) on ice. The cells were then homogenized and centrifuged at 1000 g for 1 min to remove any cell debris. Protein was quantified using a modified Lowry assay (DC assay, Bio-Rad, Hercules, Calif.) with bovine serum albumin as the standard. Protein homogenate was then denatured in Laemmli buffer (Sigma-Aldrich, St. Louis, Mo.) by boiling for 10 min. Approximately 10 µg protein was loaded per well for each sample. Protein was separated on NuPAGE® 10% Bis-Tris precast gels (Invitrogen, Carlsbad, Calif.) and transferred onto nitrocellulose membranes. Immunoblotting was done against anti-human YAPH9 (Santa Cruz Biotechnologies, USA), TAZ (Abnova), and beta-actin (Abcam, Cambridge, Mass.) overnight at 4° C. This was followed by incubation with secondary antibodies conjugated with horseradish peroxidase (HRP; Kirkegaard & Perry Laboratories, Inc, MD, USA) for 1 h at 37° C. The bands were then amplified and detected colorimetrically following protocols detailed using the Amplified Opti-4CN kit (Bio-Rad Laboratories, USA). Blots were then imaged using ImageQuant 350 imaging system (GE Healthcare Life Sciences, USA). The optical densities of the protein bands were quantified using NIH ImageJ (54, 55).

Statistics.

All statistics were performed using SigmaPlot 11 (Systat Software, Inc, San Jose, Calif.). Pairwise comparisons were assessed using Student's t-test. Throughout the example statistically significant differences are denoted with *$p<0.05$, $p<0.01$, *$p<0.001$ unless stated otherwise.

Results

Figure 2:
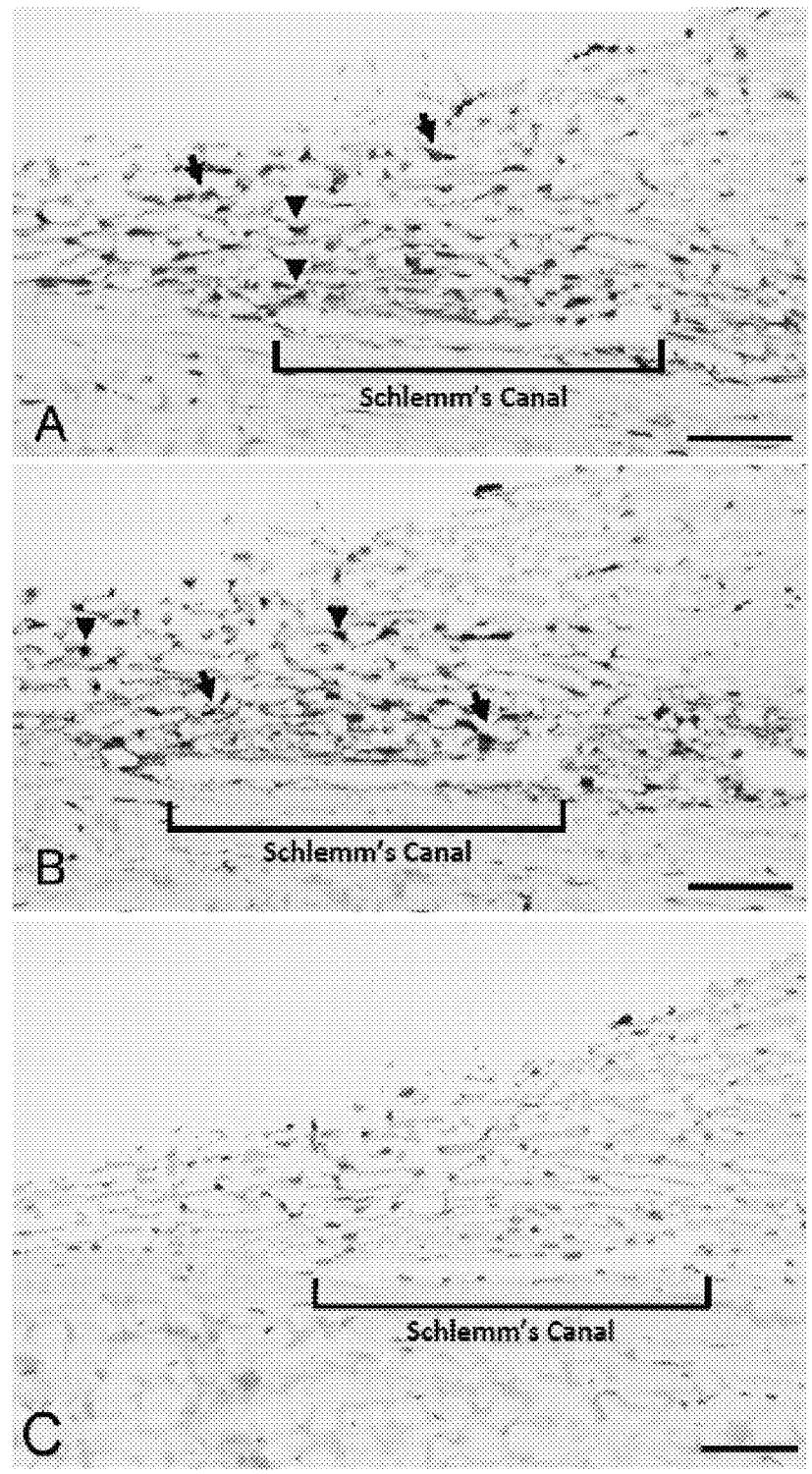
FIGS. 2A-C illustrate that YAP (A) and TAZ (B) are expressed in human trabecular meshwork tissue. Strong cytoplasmic localization (black arrows) was observed for YAP and TAZ in all cells with multifocal nuclear localization in some cells (black arrow heads). No protein expression was observed in sections stained without primary antibody (C). Schlemm's canal is indicated with a bracket. Scale bar represents 50 μm.

Immunohistochemical staining of HTM tissue from a normal donor showed both YAP and TAZ were present in HTM cells as well as in Schlemm's canal cells (FIG. 2). Both YAP and TAZ were found to be broadly localized in the cytoplasm (black arrows) with some cells having a strong nuclear localization (black arrowheads).

Figure 3:
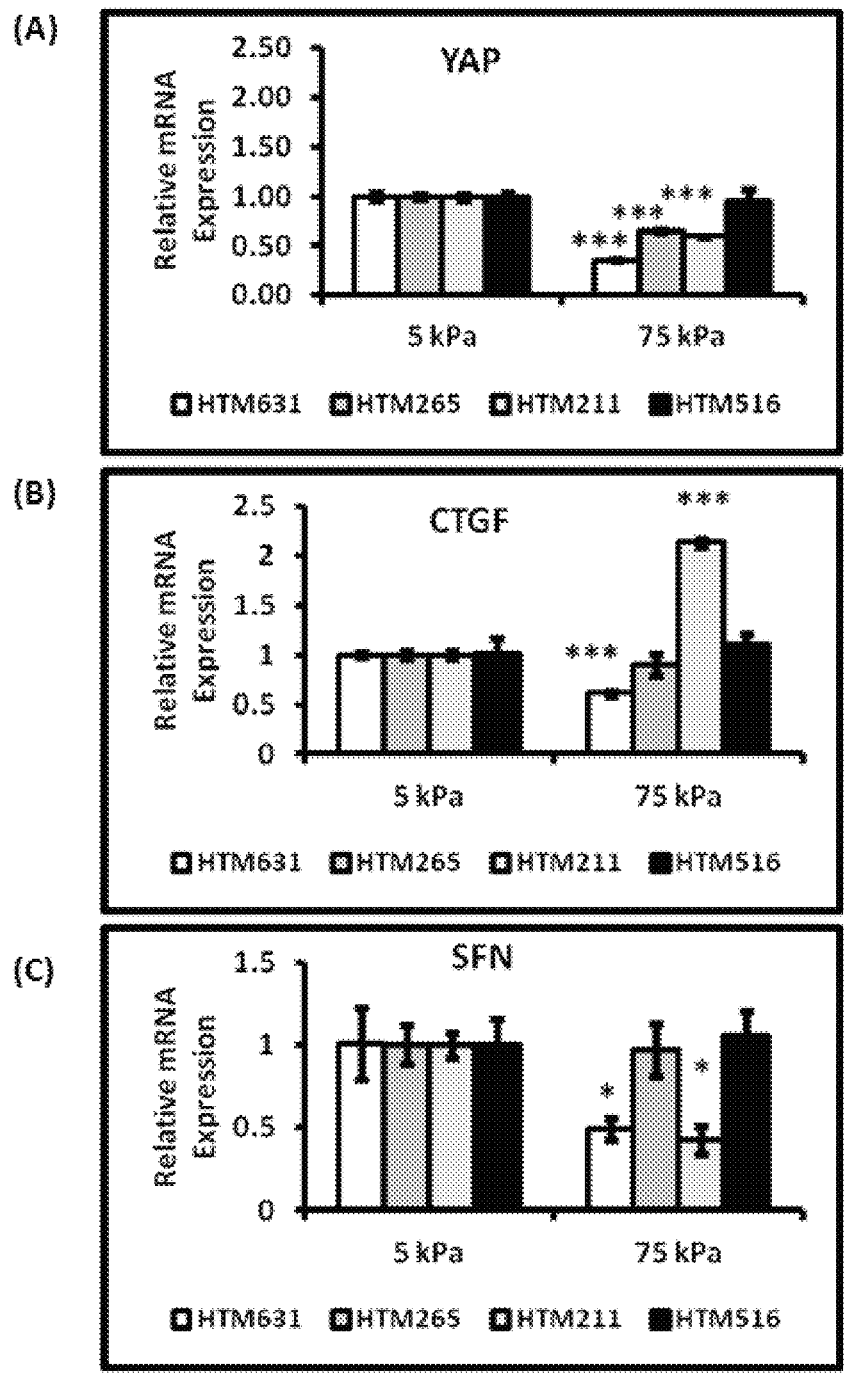
FIGS. 3A-C illustrate that YAP, CTGF and SFN expression were differentially modulated significantly by substratum stiffness in HTM cells. Graphs demonstrate significant downregulation of (A) YAP (B) CTGF and (C) SFN in HTM631 cells that were cultured on the pathomimetic substrate. Expression of CTGF and SFN genes in the other cells closely followed the expression of YAP on the 75 kPa substrate, but was not significantly different than the 5 kPa substrate. Donor lineage is indicated by HTM631, HTM265, HTM211 and HTM516. Results are mean±SD, n=3, *p<0.05, ***p<0.001 with respect to 5 kPa values, t-test.
Figure 4:
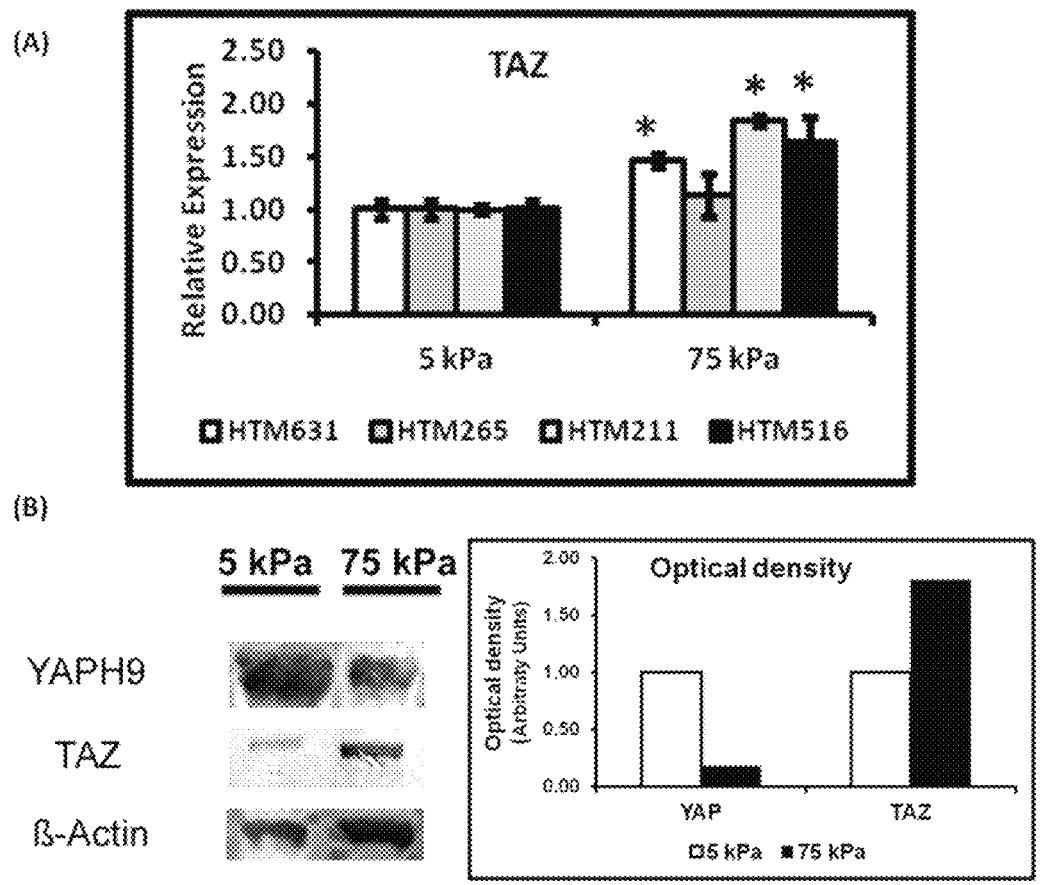
FIGS. 4A-B. Panel (A) illustrates that expression of TAZ was significantly elevated in HTM cells when cultured on stiffer substrates. TAZ expression on the 75 kPa substrates was elevated in HTM516 and HTM631 cells. This increase in gene expression was also accompanied by an increase in its protein expression. Donor lineage is indicated by HTM631, HTM265, HTM211 and HTM516. Results are mean±SD, n=3, *p<0.05 with respect to values on 5 kPa, t-test. Panel (B) illustrates Western blot analyses of YAP and TAZ normalized to β-actin in control HTM631 cells. The desired representative blots were cut and aligned together as is shown here. The band for YAP occurred at a molecular weight between 65-75 kDa, TAZ around 75 kDa, and β-actin around 42 kDa. YAP is downregulated while TAZ is upregulated on stiffer substrates consistent with the mRNA expression of YAP and TAZ. Graph demonstrates the optical density of the bands normalized to β-actin.
Figure 5:
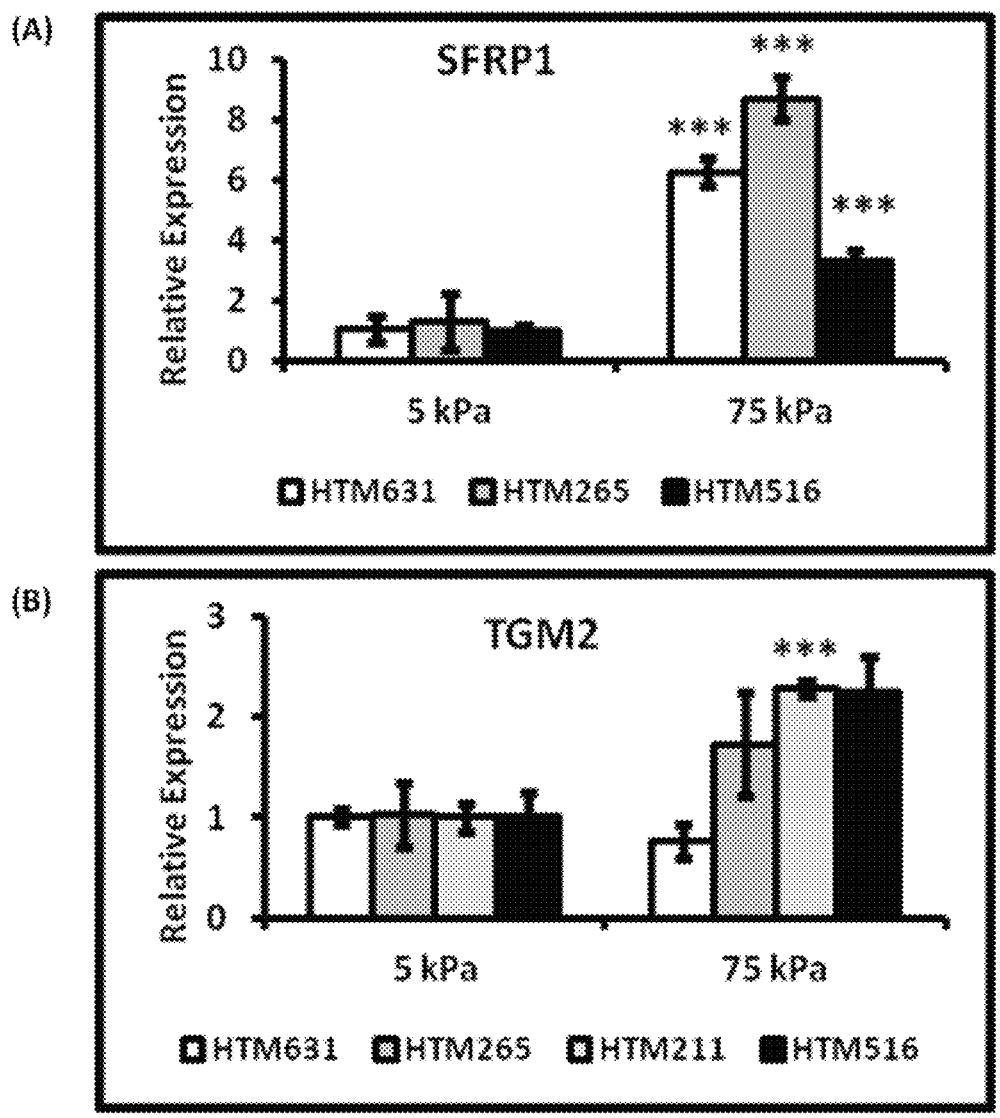
FIGS. 5A-B illustrate that SFRP-1 (panel A) and TGM2 (panel B) expression were upregulated on the pathomimetic substrates. SFRP-1 and TGM2 were markedly increased in HTM cells grown on the 75 kPa substrates in comparison to the 5 kPa substrates. Donor lineage is indicated by HTM631, HTM265, HTM211 and HTM516. Results are mean±SD, n=3, ***p<0.001 with respect to 5 kPa values, t-test; for TGM2 expression in HTM516 cells (p=0.052).

To determine the effects of substrate stiffness on the expression of YAP and/or TAZ, HTM cells were grown on homeomimetic (5 kPa) and pathomimetic (75 kPa) hydrogels for seven days in the absence of DEX. Homeomimetic hydrogel has biophysical attributes that mimic the normal and soft state of biological tissues, while pathomimetic gel mimics the disease and stiff state. The mRNA expression of YAP was significantly downregulated in three of the four donor HTM cells (HTM631, HTM265 and HTM211 cells) cultured on stiffer substrates (FIG. 3A). YAP protein expression was also markedly decreased in HTM631 cells on the 75 kPa hydrogels (FIG. 4B). In contrast, TAZ mRNA expression in 3 of the 4 donors was greater in cells cultured on stiffer substrates. For example, in HTM516 and HTM211 cells, gene expression of TAZ was ~1.8 fold greater in cells cultured on 75 kPa versus 5 kPa hydrogels (FIG. 4A). CTGF mRNA expression was also influenced by the substrate stiffness, but the effect was donor dependent. While, cells isolated from one donor (HTM631) demonstrated a 1.6 fold decrease in CTGF. HTM211 cells showed a dramatic increase (>2 fold) in mRNA expression on the stiffer substrates compared to the homeomimetic ones. There was no significant difference in the cells isolated from the other two donors (HTM265 and HTM516), but decreases in CTGF followed decreases in YAP (FIG. 3B vs. FIG. 3A). Donor dependent variability in expression patterns was also observed with SFN mRNA expression (encoding for 14-3-3σ). In HTM631 and HTM211 donor cells, SFN mRNA was two-fold lower (FIG. 3C), but with other donors (HTM265 and HTM516) no significant differences were seen. Together the trend is consistent with the conclusion that a decrease in expression of SFN in cells on the stiffer hydrogels followed YAP (FIG. 3C vs. FIG. 3A). In contrast to the trends shown by YAP, CTGF and SFN, SFRP-1 and TGM2 expression tended to increase on stiffer substrates. SFRP-1 was significantly increased in cells from at least three donors (FIG. 5A). TGM2 followed a similar trend in cells from three of four donors (HTM265, HTM211 and HTM516), consistent with previous findings (11). For example in HTM516 and HTM211 cells, TGM2 increased more than 2-fold on the stiffer hydrogels (FIG. 5B).

Figure 6:
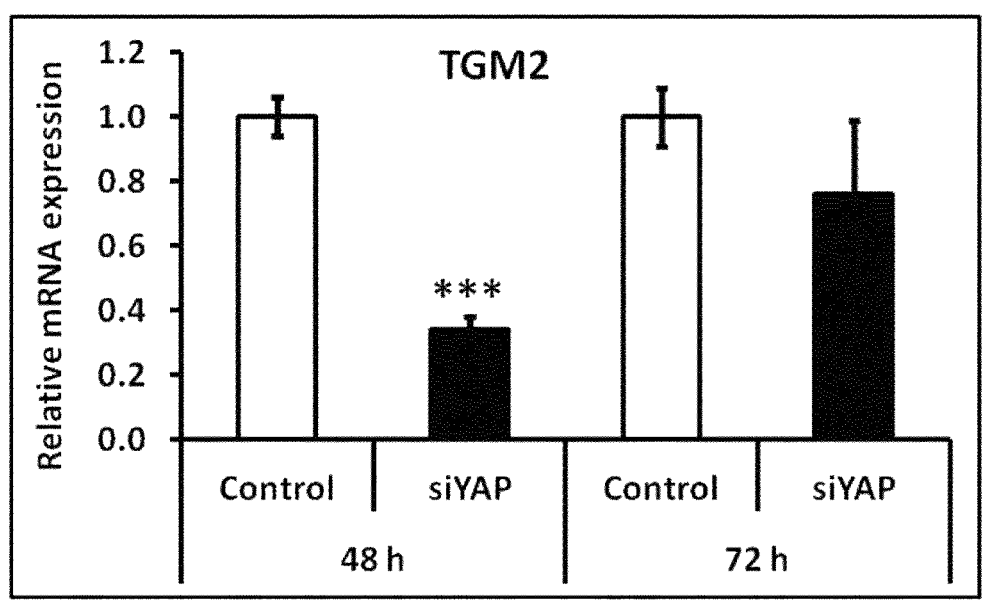
FIG. 6 illustrates that TGM2 was also regulated by YAP. To investigate the relationship between YAP and TGM2, YAP was knocked-down, using siRNA specific to YAP, to levels<20% of control siRNA. YAP knockdown was associated with a dramatic inhibition of TGM2 expression (<30% when compared with control) within 48 h. However, TGM2 mRNA levels appeared to recover to approximately 80% expression in control cells after 72 h although YAP expression remained below 20%. Results are mean±SD, n=3, ***p<0.001 with respect to 5 kPa values, t-test.

To determine a specific role of YAP in TGM2 expression, we knocked down YAP expression in HTM cells using siRNA. At 48 h after transfection, YAP knockdown was confirmed at 13% of control and TGM2 expression dropped to 34% of control (FIG. 6). However, this loss was transient. 72 h after transfection, YAP was still effectively silenced (15% of control), but TGM2 expression had mostly recovered (76%).

Figure 7:
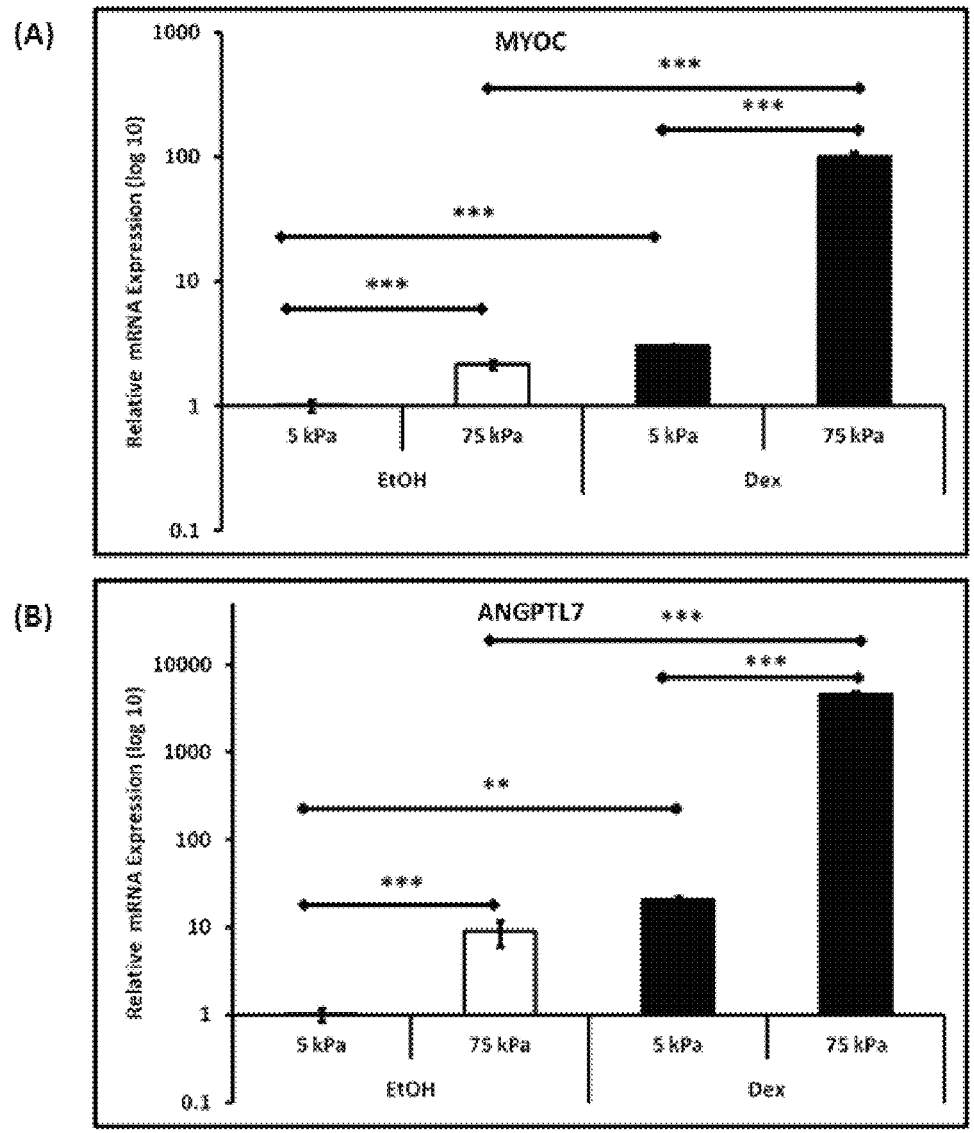
FIGS. 7A-B illustrate that Myocilin (MYOC) and ANGPTL7 expression in HTM cells were modulated significantly by substratum stiffness. Representative graphs to illustrate the trends in expression of (A) Myocilin and (B) ANGPTL7 in HTM631 cells clearly demonstrate that both genes were significantly upregulated when cultured on stiffer substrates. A similar trend was demonstrated for HTM cells from two other donors. Treatment with $10^{-7}$ M dexamethasone (DEX) accentuated this response. Results are mean±SD (n=3), *p<0.001, p<0.01, t-test.

Finally, to determine the influence of dexamethasone on substrate stiffness of HTM cells, we treated cells from all donors with DEX over seven days. In our expression panel, we included two ECM related genes MYOC and ANGPTL7 known to be upregulated with dexamethasone. Substratum stiffness had a marked effect on the mRNA expression of MYOC and ANGPTL7 with upregulation of both genes found in all three donors after 7 days on the pathomimetic polyacrylamide hydrogels compared to the homeomimetic substrates (FIG. 7). However, the relative response to MYOC and ANGPTL7 were suppressed when cells were cultured on the softer 5 kPa substrates. For example, in HTM631 cells, MYOC expression increased 3-fold on 5 kPa hydrogels on treatment with DEX, but it was elevated more than 100-fold on the 75 kPa hydrogels, compared to vehicle control on 5 kPa hydrogels (FIG. 7). In HTM631 cells, ANGPTL7 expression was increased 20-fold on 5 kPa hydrogels and greater than 4500-fold on 75 kPa hydrogels with DEX treatment (FIG. 7). No trends in other genes were noted with the DEX treatment.

Discussion

Discussion of examples includes theories regarding the biological and chemical mechanisms that underlie the data observed. These theories and mechanisms do not form any part. Similarly, the invention is not limited by the theories or mechanisms described herein.

Alterations in trabecular meshwork ECM have long been correlated with glaucoma (56, 57). In addition to the morphologic changes documented with light and electron microscopy, atomic force microscopy studies have recently documented that the meshwork is stiffer with glaucoma (7). The altered mechanical properties of the HTM in glaucoma (7) and the changes in the substratum biophysical properties have dramatic effects on HTM cell phenotype (9, 11). In this example, two of the proteins known to be involved with the ECM, MYOC and ANGPTL-7 were significantly upregulated when HTM cells were grown on substrates with stiffness similar to the glaucomatous meshwork in vivo. It is important to note that elevated stiffness has previously been reported to downregulate ANGPTL-7 (11), however, those experiments used a much shorter (24 h) time point. Taken together, these reports revealed a temporal component to ANGPTL-7 regulation.

Both MYOC and ANGPTL-7 have previously been reported to be upregulated by GCs such as DEX (58, 59). In the present example, DEX added to HTM cells grown on hydrogels, resulted in marked increases in mRNA expression of these two genes. Additionally, this DEX stimulated response of MYOC and ANGPTL-7 was even more striking in HTM cells grown on the pathomimetic substrates in comparison to the homeomimetic substrates. This is particularly important to consider while using GCs as a model for glaucoma. The DEX response of MYOC and ANGPTL7 observed on stiffer substrates is significantly attenuated on softer substrates (typical of normal HTM), is consistent with the conclusion that stiff substrates, such as the cultureware used in many previous studies, induces a dramatically different DEX phenotype than would be observed in vivo. Thus, growing HTM cells on the homeomimetic and pathomimetic substrates described in this report may be a better in vitro model for studying glaucoma than HTM cells grown on TCP. Furthermore, these data are consistent with the conclusion that feedback loops in tissue stiffening. An increase in ANGPTL7 can reduce the deposition of key ECM proteins (29), resulting in reduced ECM stiffness and therefore reduced ANGPTL7 expression.

While the prime event responsible for changing the biophysical attributes of the microenvironment surrounding cells remains unknown, an increasing body of literature suggests that various proteins are involved in mechanosensing and mechanotransduction. YAP and TAZ were identified as two mechanotransducers of substrate rigidity that also act as nuclear relays for activation of transcription factors (35). Additionally, recent studies have demonstrated that YAP and/or TAZ plays a critical role in tumorigenesis, and renal and pulmonary diseases (36, 60, 61). We thus explored the expression of YAP and/or TAZ in HTM cells as well as other genes related to YAP and/or TAZ and the ECM. This example shows that YAP and TAZ were present in all layers of HTM including the JCT, which is thought to provide the majority of resistance to aqueous humor outflow (5). Undoubtedly, it would be very interesting to compare YAP and/or TAZ expression in the HTM of normal and glaucomatous donors but HTM tissue from patients with glaucoma is difficult to obtain. We investigated the regulation of YAP and/or TAZ in HTM cells grown on biologically relevant substrates. Indeed, altered expression of YAP and/or TAZ in response to substrate properties was observed. YAP mRNA and protein expression was elevated on the softer hydrogels, while TAZ mRNA and protein was elevated on the stiffer hydrogels demonstrating that YAP and/or TAZ are actively regulated in the HTM and therefore may serve as mechanotransducers in HTM cells. This inverse relation between YAP and/or TAZ expression, if conserved in vivo, would point to divergent influences of the two proteins, with YAP being more important during normal functioning of the HTM, and TAZ growing in influence as the HTM is altered in glaucoma and contrasted with the Dupont study which demonstrated that both YAP and TAZ were upregulated on stiffer substrates in mammary epithelial cells (35). Consistent with a recent publication, (62) these results demonstrate that YAP and TAZ may respond differently in various cell types and it is important to investigate their role in the cell type of interest.

In line with this, it is important to keep in mind other biophysical or biochemical stimuli capable of modulating YAP and/or TAZ expression and localization may be present in the HTM. Iyer and colleagues have recently shown that the activity of autotaxin, the enzyme that produces lysophosphatidic acid (LPA), is upregulated in glaucoma and inhibition of LPA production led to a reduction in IOP (63). While the previous study did not describe a complete mechanism, Yu et al. (64) and Miller et al. (62) have identified LPA as an activator of YAP and/or TAZ. These reports, considered together, point to a novel autotaxin-LPA-YAP and/or TAZ signaling axis.

CTGF is highly expressed in the HTM (65), modulates the expression of ECM proteins relevant to POAG (66), and has been linked to elevated IOP (67). Importantly, YAP (68, 69) and TAZ (70) are both capable of directly regulating CTGF. In the present example, CTGF expression closely mirrored YAP expression in three of the four donor cells. In cells from one donor (HTM631), CTGF was strongly inhibited on the stiffer substrates while there was minimal change in cells from the other two donors (HTM265 and HTM516). However, in cells from HTM211, CTGF expression was markedly elevated. Concurrently it was also observed that TAZ expression was elevated in 3 of the 4 donor cells (HTM631, HTM211 and HTM516). These data are consistent with the conclusion that there is high inter-individual variability in CTGF expression. The data also are consistent with the conclusion that differential regulation by YAP or TAZ following exposure to different substrates. This result is especially intriguing. It must be noted that most data published on YAP and/or TAZ and gene regulation do not individually distinguish the specificity of YAP or TAZ. A more nuanced mechanism is demonstrated by our studies. We infer, from our data, that CTGF expression may be determined by the relative dominance of YAP or TAZ. Without limiting the current invention to the underlying biological and chemical mechanisms, TAZ expression is more dominant under glaucomatous or pathomimetic conditions to drive CTGF expression, while YAP is the dominant regulator of CTGF under normal conditions or homeostasis.

TGM2 is an enzyme which crosslinks ECM proteins and thus increases their resistance to mechanical or proteolytic degradation (71). It is upregulated in glaucoma and contributes to the decreased outflow facility of glaucomatous TM (52). Importantly, it is regulated by YAP and/or TAZ35, and our results are consistent with the conclusion that it is influenced particularly by TAZ in HTM cells, as silencing YAP only resulted in a transient reduction in TGM2; specifically TGM2 expression levels recovered in the cells 72 h after siRNA treatment while YAP expression levels remained below 20%. Similar to TAZ expression, our results show increased TGM2 expression on pathomimetic substrates, consistent with our previous demonstration of increased TGM2 after acute (24 h) exposure to pathomimetic substrates (11). These data show a persistent effect of substrate stiffness on TGM2 expression, concordant with data showing increased TGM2 expression in glaucomatous tissue (52). In vivo, this association could result in positive feedback of HTM stiffening with elevated stiffness leading to increased TGM2 expression, which in turn crosslinks the ECM, resulting in further stiffening of the tissue. Thus, decreasing the expression of TAZ, and thus downstream TGM2, is a novel therapeutic target in the treatment of glaucoma.

A key regulator of YAP and/or TAZ, SFN (14-3-3σ), was also modulated by substrate stiffness. Interestingly, the trend for expression of SFN across 3 of the 4 donors followed that of YAP. SFN sequesters both YAP and TAZ in the cytoplasm thus inhibiting their transcriptional activity (38, 40). The ability of SFN to regulate YAP and/or TAZ in HTM cells is important to consider in the development of new therapeutic targets for glaucoma.

The Wnt signaling pathway, an important pathway in glaucoma (43, 72), is also influenced by YAP and/or TAZ. The results from the present example also implicate substratum stiffness in Wnt regulation. SFRP-1, a canonical Wnt antagonist (73, 74), was significantly increased on pathomimetic substrates. These data were consistent with previous reports of SFRP-1 being over-expressed in glaucomatous HTM cells and increased expression resulting in elevated IOP (43, 72). TAZ, also upregulated on pathomimetic substrates, has been identified as a Wnt antagonist (41). Our results are consistent with the conclusion that the overexpression of SFRP-1 and TAZ in cells cultured on pathomimetic substrates inhibits Wnt signaling in glaucoma. These data are consistent with the view that antagonism of Wnt signaling was a causative factor in increased IOP (43) or that constitutive Wnt expression is important in maintaining a normal IOP in the HTM.

Data of this example show the importance of changes in the ECM and the mechanosensors YAP and/or TAZ in glaucoma. Additionally, we highlight the importance of incorporating substratum biophysical properties into an in vitro study design for investigating molecular mechanisms of diseases such as glaucoma. This example points to YAP and/or TAZ mechanotransduction as a central pathway in mediating HTM cell response to the increased stiffness observed in glaucoma. This is particularly exciting as it identifies molecular targets for glaucoma therapeutics.

References for Example 1

1. Quigley H A, Broman A T. The number of people with glaucoma worldwide in 2010 and 2020. Br J Ophthalmol 2006; 90:262-267.
2. Quigley H A. Open-angle glaucoma. N Engl J Med 1993; 328:1097-1106.
3. Johnson M. What controls aqueous humour outflow resistance? Exp Eye Res 2006; 82:545-557.
4. Johnstone M A, Grant W G. Pressure-dependent changes in structures of the aqueous outflow system of human and monkey eyes. Am J Ophthalmol 1973; 75:365-383.
5. Maepea O, Bill A. Pressures in the juxtacanalicular tissue and Schlemm's canal in monkeys. Exp Eye Res 1992; 54:879-883.
6. Gottanka J, Johnson D H, Martus P, Lutjen-Drecoll E. Severity of optic nerve damage in eyes with POAG is correlated with changes in the trabecular meshwork. Journal of glaucoma 1997; 6:123-132.
7. Last J A, Pan T, Ding Y, et al. Elastic modulus determination of normal and glaucomatous human trabecular meshwork. Investigative Ophthalmology & Visual Science 2011; 52:2147-2152.
8. McKee C T, Wood J A, Shah N M, et al. The effect of biophysical attributes of the ocular trabecular meshwork associated with glaucoma on the cell response to therapeutic agents. Biomaterials 2011; 32:2417-2423.
9. Wood J A, McKee C T, Thomasy S M, et al. Substratum compliance regulates human trabecular meshwork cell behaviors and response to latrunculin B. Investigative Ophthalmology & Visual Science 2011; 52:9298-9303.
10. Wood J A, Shah N M, McKee C T, et al. The role of substratum compliance of hydrogels on vascular endothelial cell behavior. Biomaterials 2011; 32:5056-5064.
11. Thomasy S M, Wood J A, Kass P H, Murphy C J, Russell P. Substratum Stiffness and Latrunculin B Regulate Matrix Gene and Protein Expression in Human Trabecular Meshwork Cells. Investigative Ophthalmology & Visual Science 2012; 53:952-958.
12. Saha K, Keung A J, Irwin E F, et al. Substrate Modulus Directs Neural Stem Cell Behavior. Biophysical Journal 2008; 95:4426-4438.
13. Pelham R J, Wang Y. Cell locomotion and focal adhesions are regulated by substrate flexibility. Proceedings of the National Academy of Sciences 1997; 94:13661.
14. Chew S Y, Low W C. Scaffold-based approach to direct stem cell neural and cardiovascular differentiation: An analysis of physical and biochemical effects. Journal of Biomedical Materials Research Part A 2011; 97A:355-374.
15. Leipzig N D, Shoichet M S. The effect of substrate stiffness on adult neural stem cell behavior. Biomaterials 2009; 30:6867-6878.
16. Georges P C, Janmey P A. Cell type-specific response to growth on soft materials. J Appl Physiol 2005; 98:1547-1553.
17. Wong J Y, Velasco A, Rajagopalan P, Pham Q. Directed movement of vascular smooth muscle cells on gradient-compliant hydrogels. Langmuir 2003; 19:1908-1913.
18. Reinhart-King C A, Dembo M, Hammer D A. Cell-cell mechanical communication through compliant substrates. Biophysical Journal 2008; 95:6044-6051.
19. Han H, Wecker T, Grehn F, Schlunck G. Elasticity-Dependent Modulation of TGF-β Responses in Human Trabecular Meshwork Cells. Investigative Ophthalmology & Visual Science 2011; 52:2889-2896.
20. Gasiorowski J Z, Russell P. Biological properties of trabecular meshwork cells. Experimental eye research 2009; 88:671-675.
21. Stokes J, Walker B R, Campbell J C, Seckl J R, O'Brien C, Andrew R. Altered peripheral sensitivity to glucocorticoids in primary open-angle glaucoma. Investigative Ophthalmology & Visual Science 2003; 44:5163-5167.
22. Clark A F, Morrison J C. Steroid-induced glaucoma. Glaucoma: science and practice 2003; 197-206.
23. Zhuo Y H, He Y, Leung K W, et al. Dexamethasone disrupts intercellular junction formation and cytoskeleton organization in human trabecular meshwork cells. Mol Vis 2010; 16:61-71.
24. Knepper P A, Collins J A, Frederick R. Effects of dexamethasone, progesterone, and testosterone on IOP and GAGs in the rabbit eye. Investigative Ophthalmology & Visual Science 1985; 26:1093-1100.
25. Clark A F, Brotchie D, Read A T, et al. Dexamethasone alters F-actin architecture and promotes cross-linked actin network formation in human trabecular meshwork tissue. Cell Motility and the Cytoskeleton 2005; 60:83-95.
26. Clark A F, Wilson K, McCartney M D, Miggans S T, Kunkle M, Howe W. Glucocorticoid-induced formation of cross-linked actin networks in cultured human trabecular meshwork cells. Invest Ophthalmol Vis Sci 1994; 35:281-294.

27. Russell P, Gasiorowski J Z, Nealy P F, Murphy C J. Response of human trabecular meshwork cells to topographic cues on the nanoscale level. Investigative Ophthalmology & Visual Science 2008; 49:629-635.
28. Rozsa F W, Reed D M, Scott K M, et al. Gene expression profile of human trabecular meshwork cells in response to long-term dexamethasone exposure. Mol Vis 2006; 12:125-141.
29. Comes N, Buie L K, Borrás T. Evidence for a role of angiopoietin-like 7 (ANGPTL7) in extracellular matrix formation of the human trabecular meshwork: implications for glaucoma. Genes Cells 2011; 16:243-259.
30. Fingert J H, Stone E M, Sheffield V C, Alward W L M. Myocilin Glaucoma. Surv Ophthalmol 2002; 47:547-561.
31. Polansky J. Current perspectives on the TIGR/MYOC gene (Myocilin) and glaucoma. Ophthalmol Clin North Am 2003; 16:515.
32. Tamm E R. Myocilin and glaucoma: facts and ideas. Prog Retin Eye Res 2002; 21:395-428.
33. Kuchtey J, Kallberg M E, Gelatt K N, Rinkoski T, Komaromy A M, Kuchtey R W. Angiopoietin-like 7 secretion is induced by glaucoma stimuli and its concentration is elevated in glaucomatous aqueous humor. Invest Ophthalmol Vis Sci 2008; 49:3438-3448.
34. Polansky J R, Fauss D J, Zimmerman C C. Regulation of TIGR/MYOC gene expression in human trabecular meshwork cells. Eye 2000; 14:503-514.
35. Dupont S, Morsut L, Aragona M, et al. Role of YAP and/or TAZ in mechanotransduction. Nature 2011; 474:179-183.
36. Wang K, Degerny C, Xu M, Yang X J. YAP, TAZ, and Yorkie: a conserved family of signal-responsive transcriptional coregulators in animal development and human disease. Biochem Cell Biol 2009; 87:77-91.
37. Zhao B, Tumaneng K, Guan K L. The Hippo pathway in organ size control, tissue regeneration and stem cell self-renewal. Nature cell biology 2011; 13:877-883.
38. Zhao B, Li L, Guan K L. Hippo signaling at a glance. J Cell Sci 2010; 123:4001-4006.
39. Dong J, Feldmann G, Huang J, et al. Elucidation of a Universal Size-Control Mechanism in *Drosophila* and Mammals. Cell 2007; 130:1120-1133.
40. Kanai F, Marignani P A, Sarbassova D, et al. TAZ: a novel transcriptional co-activator regulated by interactions with 14-3-3 and PDZ domain proteins. EMBO J 2000; 19:6778-6791.
41. Varelas X, Miller B W, Sopko R, et al. The Hippo pathway regulates Wnt/beta-catenin signaling. Dev Cell 2010; 18:579-591.
42. Finch P W, He X, Kelley M J, et al. Purification and molecular cloning of a secreted, Frizzled-related antagonist of Wnt action. Proc Natl Acad Sci USA 1997; 94:6770-6775.
43. Wang W H, McNatt L G, Pang I H, et al. Increased expression of the WNT antagonist sFRP-1 in glaucoma elevates intraocular pressure. J Clin Invest 2008; 118:1056.
44. Vassilev A, Kaneko K J, Shu H, Zhao Y, DePamphilis M L. TEAD/TEF transcription factors utilize the activation domain of YAP65, a Src/Yes-associated protein localized in the cytoplasm. Genes Dev 2001; 15:1229-1241.
45. Cui C B, Cooper L F, Yang X, Karsenty G, Aukhil I. Transcriptional coactivation of bone-specific transcription factor Cbfa1 by TAZ. Mol Cell Biol 2003; 23:1004-1013.
46. Hill C S. Nucleocytoplasmic shuttling of Smad proteins. Cell Res 2008; 19:36-46.
47. Varelas X, Sakuma R, Samavarchi-Tehrani P, et al. TAZ controls Smad nucleocytoplasmic shuttling and regulates human embryonic stem-cell self-renewal. Nature cell biology 2008; 10:837-848.
48. Tripathi R C, Li J, Chan W F, Tripathi B J. Aqueous humor in glaucomatous eyes contains an increased level of TGF-beta 2. Experimental eye research 1994; 59:723-727.
49. Kottler U B, Junemann A G, Aigner T, Zenkel M, Rummelt C, Schlotzer-Schrehardt U. Comparative effects of TGF-beta 1 and TGF-beta 2 on extracellular matrix production, proliferation, migration, and collagen contraction of human Tenon's capsule fibroblasts in pseudoexfoliation and primary open-angle glaucoma. Experimental eye research 2005; 80:121-134.
50. Junglas B, Kuespert S, Seleem A A, et al. Connective tissue growth factor causes glaucoma by modifying the actin cytoskeleton of the trabecular meshwork. Am J Pathol 2012; 180:2386-2403.
51. Taylor A W. Primary Open-Angle Glaucoma: A Transforming Growth Factor-beta Pathway-Mediated Disease. Am J Pathol 2012; 180:2201-2204.
52. Tovar-Vidales T, Roque R, Clark A F, Wordinger R J. Tissue Transglutaminase Expression and Activity in Normal and Glaucomatous Human Trabecular Meshwork Cells and Tissues. Investigative Ophthalmology & Visual Science 2008; 49:622-628.
53. Rhee D J, Tamm E R, Russell P. Donor corneoscleral buttons: a new source of trabecular meshwork for research. Experimental eye research 2003; 77:749-756.
54. ImageJ N. Image processing and analysis in Java. Accessed February 2010.
55. Schneider C A, Rasband W S, Eliceiri K W. NIH Image to ImageJ: 25 years of image analysis. Nature Methods 2012; 9:671-675.
56. Yue B Y. The extracellular matrix and its modulation in the trabecular meshwork. Surv Ophthalmol 1996; 40:379-390.
57. Acott T S, Kelley M J. Extracellular matrix in the trabecular meshwork. Experimental eye research 2008; 86:543-561.
58. Tamm E R, Russell P, Epstein D L, Johnson D H, Piatigorsky J. Modulation of myocilin/TIGR expression in human trabecular meshwork. Invest Ophthalmol Vis Sci 1999; 40:2577-2582.
59. Kuchtey J, Kallberg M E, Gelatt K N, Rinkoski T, Komaromy A M, Kuchtey R W. Angiopoietin-like 7 secretion is induced by glaucoma stimuli and its concentration is elevated in glaucomatous aqueous humor. Invest Ophthalmol Vis Sci 2008; 49:3438-3448.
60. Makita R, Uchijima Y, Nishiyama K, et al. Multiple renal cysts, urinary concentration defects, and pulmonary emphysematous changes in mice lacking TAZ. American Journal of Physiology-Renal Physiology 2008; 294:F542-F553.
61. Zhao B, Li L, Lei Q, Guan K L. The Hippo-YAP pathway in organ size control and tumorigenesis: An updated version. Genes Dev 2010; 24:862.
62. Miller E, Yang J, Deran M, et al. Identification of Serum-Derived Sphingosine-1-Phosphate as a Small Molecule Regulator of YAP. Chem Biol 2012.
63. Iyer P, Lalane R, 3rd, Morris C, Challa P, Vann R, Rao P V. Autotaxin-lysophosphatidic Acid axis is a novel molecular target for lowering intraocular pressure. PloS one 2012; 7:e42627.

64. Yu F X, Zhao B, Panupinthu N, et al. Regulation of the Hippo-YAP Pathway by G-Protein-Coupled Receptor Signaling. Cell 2012; 150:780-791.
65. Tomarev S I, Wistow G, Raymond V, Dubois S, Malyukova I. Gene expression profile of the human trabecular meshwork: NEIBank sequence tag analysis. Invest Ophthalmol Vis Sci 2003; 44:2588-2596.
66. Junglas B, Yu A H, Welge-Lussen U, Tamm E R, Fuchshofer R. Connective tissue growth factor induces extracellular matrix deposition in human trabecular meshwork cells. Experimental eye research 2009; 88:1065-1075.
67. Junglas B, Kuespert S, Seleem A A, et al. Connective tissue growth factor causes glaucoma by modifying the actin cytoskeleton of the trabecular meshwork. Am J Pathol 2012; 180:2386-2403.
68. Zhao B, Ye X, Yu J, et al. TEAD mediates YAP-dependent gene induction and growth control. Genes Dev 2008; 22:1962-1971.
69. Huntoon C J, Nye M D, Geng L, et al. Heat shock protein 90 inhibition depletes LATS1 and LATS2, two regulators of the mammalian hippo tumor suppressor pathway. Cancer Research 2010; 70:8642-8650.
70. Zhang H, Liu C-Y, Zha Z-Y, et al. TEAD Transcription Factors Mediate the Function of TAZ in Cell Growth and Epithelial-Mesenchymal Transition. J Biol Chem 2009; 284:13355-13362.
71. Beninati S, Piacentini M. The transglutaminase family: an overview: minireview article. Amino Acids 2004; 26:367-372.
72. Mao W, Millar J C, Wang W H, et al. Existence of the canonical Wnt signaling pathway in the human trabecular meshwork. Invest Ophthalmol Vis Sci 2012.
73. Katoh Y, Katoh M. WNT antagonist, SFRP1, is Hedgehog signaling target. Int J Mol Med 2006; 17:171.
74. Kawano Y, Kypta R. Secreted antagonists of the Wnt signaling pathway. J Cell Sci 2003; 116:2627-2634.

Example 2

Substratum Stiffness and Lat-B Modulate Genes Associated with YAP and TAZ

The compliance of the human trabecular meshwork (HTM) has been shown to dramatically stiffen in glaucomatous patients. This example determines the impact of substratum stiffness and latrunculin-B (Lat-B), on the expression and activity of the mechanotransducers, Yes-associated protein (YAP) and transcriptional coactivator with PDZ-binding domain (TAZ), in primary HTM cells as the cells start to recover from Lat-B treatment.

Materials and Methods

Hydrogel Fabrication.

Polyacrylamide hydrogels mimicking the stiffness of the normal (5 kPa) and glaucomatous (75 kPa) HTM were prepared utilizing previously described procedures (McKee et al., 2011; Wood et al., 2011b). Briefly, hydrogels were fabricated and then sterilized with ultraviolet light and rinsed every 24 hours for at least 72 hours in Dulbecco's phosphate buffered solution (DPBS, Hyclone, Logan, Utah) to fully hydrate the hydrogels and to ensure removal of monomeric acrylamide since free acrylamide has been previously shown to disrupt cytoskeletal structure (Arocena, 2006). Following hydration, the hydrogels (10 mm) were adhered to TCP, stored in HTM cell medium, DME/F-12 medium containing 2.5 mM L-glutamine supplemented with 1% penicillin-streptomycin with amphotericin b (Lonza, Walkerville, Md.) and 10% fetal bovine serum (Atlanta Biologicals, Lawrence, Ga.), for 24 hrs and coated with a proprietary fibronectin/collagen (FNC) mixture (AthenaES, Baltimore, Md.) for 20 minutes. The elastic modulus of the hydrogels used were previously validated with atomic force microscopy at 4±2 kPa and 71±5 kPa for the 5 and 75 kPa gels respectively (McKee et al., 2011; Radmacher et al., 1992).

HTM Cell Isolation and Culture.

Primary HTM cells were isolated from corneoscleral rims considered unsuitable for transplant from donors with no prior history of ophthalmic disease as previously described (McKee et al., 2011; Rhee et al., 2003; Wood et al., 2011b). Isolated cells were cultured in HTM cell medium and all studies were conducted using cells prior to the eighth passage. HTM cells were plated at a density of 1.5×105 on FNC-coated TCP and 75 kPa hydrogels and 2.5×105 on FNC-coated 5 kPa hydrogels for 24 h prior to Lat-B treatment. The 5 kPa hydrogels were plated a higher density than the other substrates because HTM cells proliferate more slowly on the 5 kPa hydrogels (Wood et al., 2011a), and to ensure that there was enough mRNA present to perform PCR.

Latrunculin-B Treatment.

Lyophilized Lat-B (Cal Biochem, La Jolla, Calif.) was re-suspended to a final concentration of 2.5 mM in dimethyl sulfoxide (DMSO) (Fisher, Pittsburg, Pa.). Fresh solutions of 2.0 µM Lat-B were prepared in serum free DPBS for all experiments. Control samples were treated with an equivalent concentration of DMSO in serum free DPBS. Treatment with DMSO was compared to serum free DPBS only to ensure DMSO did not have an additional effect on HTM cells. Following 30 min. of exposure to Lat-B, DMSO, or DPBS, all samples were rinsed twice with HTM cell medium since serum has been shown to neutralize Lat-B (Spector et al., 1989) and then placed in 3-5 mL of HTM cell medium.

Fixation and Immunofluoresence.

One hour after treatment with Lat-B or DMSO, the cells were rinsed twice with warm DPBS and fixed in warm DPBS with 4% paraformaldehyde (Sigma-Aldrich, St. Louis, Mo.) for 20 min. They were rinsed twice more and permeabilized in DPBS with 0.5% Triton-X100 (Sigma-Aldrich, St. Louis, Mo.). They were rinsed and stored in DPBS until staining. Rabbit anti-YAP (H-125, Santa Cruz Biotechnology, Santa Cruz, Calif.) was diluted in PBS containing 0.2% A-type cold fish gelatin (Sigma-Aldrich, St. Louis, Mo.) as a blocking agent. After primary staining, cells were rinsed twice in PBS. Dylight 594-conjugated goat anti-rabbit IgG (Thermo Scientific Pierce, Rockford, Ill.) was similarly diluted. After secondary staining, the cells were again rinsed, counterstained with DAPI (Life Technologies, Carlsbad, Calif.), rinsed a final time, and stored in PBS for imaging. Cells were imaged on an Axiovert 200 M (Carl Zeiss AG, Oberkochen, Germany) inverted microscope with a 20× objective. To mitigate background signal, images were filtered with a 77.5 µm rolling ball background and local median filtering (ImageJ, NIH, Bethesda, Md.).

RNA Extraction and Quantitative Real-Time PCR.

One hour after treatment with Lat-B or DMSO, RNA was extracted using the Qiagen RNeasy kit following the manufacturer's protocol (Qiagen, Valencia, Calif.). Semi-quantitative real-time PCR (qPCR) was performed with 60 ng RNA per sample using the one-step TaqMan kit and commercially available primers for 18 S (Hs99999901_s1), YAP (Hs00371735_m1), WWTR1 (Hs00210007_m1), 14-3-3σ (Hs00968567_s1), CTGF (Hs00170014_m1), and PAI-1 (Hs01126606_m1) in total volumes of 10 μl per reaction (Applied Biosystems, Carlsbad, Calif.). The reverse transcription reaction was performed for 20 minutes at 50° C. followed by PCR enzyme activation for 10 minutes at 95° C. and forty cycles of 60° C. for 1 minute followed by 95° C. for 15 seconds. The cycle threshold ($C_t$) ranges were 11-22 for 18S, 23-27 for YAP, 23-34 for WWTR1, 27-32 for 14-3-3σ, 21-30 for CTGF and 17-23 for PAI-1. The 18S ribosomal RNA served as a reference. At least three reactions were run for each sample, and the experimental setup was performed for HTM cells from three individuals. Gene expression was normalized relative to the expression of mRNA from HTM cells on TCP treated with vehicle (DMSO), which was given a value of 1.0. In order to control for slight variations in the amount of RNA loaded into the PCR reactions, the difference in cycle threshold ($\Delta C_t$) between the gene of interest (e.g. YAP) and the average cycle threshold ($C_t$) of the house keeping gene, 18S (ran in triplicate) were calculated. By calculating the difference in $\Delta C_t$ between an experimental condition and the control condition (TCP DMSO), the experimental data was normalized to the control data. Ratios with respect to this control were calculated for all other values. The protein TAZ is encoded by the WWTR1 gene, for ease of reading, the mRNA obtained from the WWTR1 gene is designated as TAZ mRNA.

Statistical Analysis.

Data were analyzed using the Sigma Plot 11 software package (Systat Software, Chicago, Ill.). A one-way repeated measures analysis of variance (RMANOVA) was used to assess the effect of stiffness on the expression of TAZ, CTGF and PAI-1 with or without Lat-B treatment. If the one-way RMANOVA was significant, Student's t tests were performed with a sequentially rejective adaptation of the Bonferroni correction for multiple comparisons to compare each compliant hydrogel to the other compliant hydrogel or TCP with or without Lat-B treatment. A two-way RMANOVA was used to assess the effects of stiffness and donor on the expression of YAP and 14-3-3σ. If the two-way RMANOVA was significant, Student's t tests were performed with a sequentially rejective adaptation of the Bonferroni correction for multiple comparisons to compare each compliant hydrogel to other substrates with or without Lat-B treatment. A paired Student's t test was used to compare the effect of Lat-B versus DMSO treatment for each substrate. Significance was set at $p < 0.05$ for all analyses. All data are presented as mean±standard error (SEM).

Results

Substratum Stiffness & Lat-B Alters YAP and TAZ Expression.

Figure 8:
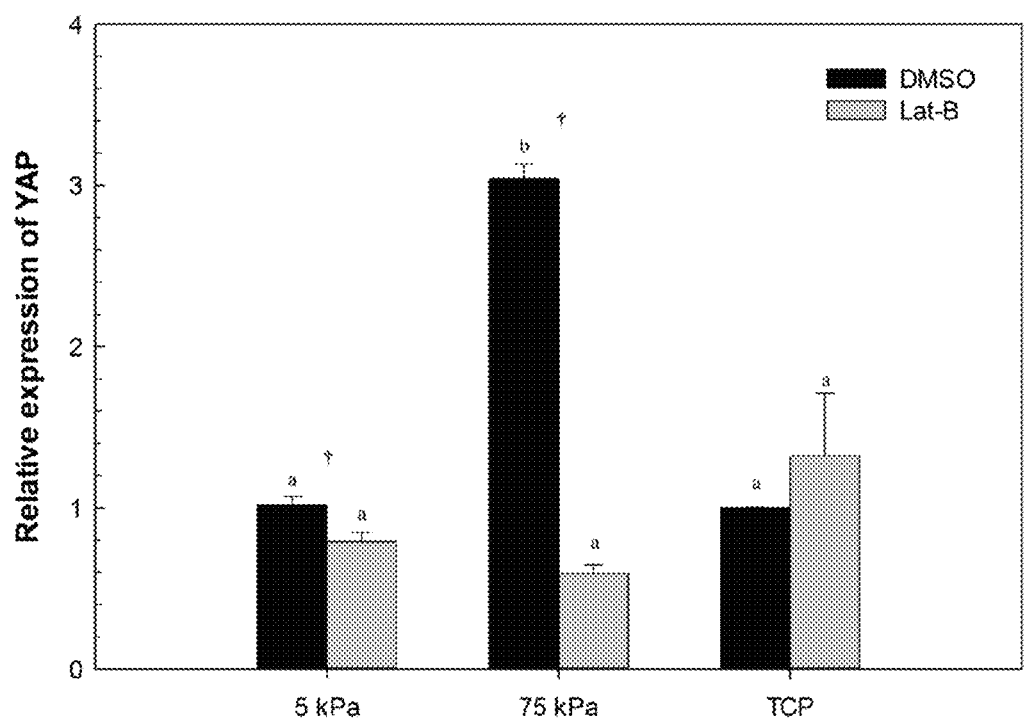
FIG. 8 illustrates that substratum stiffness impacts YAP mRNA and cellular response to Lat-B treatment in HTM cells. Cells grown on stiff hydrogels and treated with DMSO had significantly different YAP mRNA expression in comparison to DMSO-treated cells on TCP (>1 GPa) or more compliant hydrogels. Cells grown on hydrogels and treated with Lat-B had significantly less YAP mRNA expression versus treatment with DMSO. In contrast, cells grown on TCP and treated with Lat-B did not have significantly different YAP mRNA expression versus cells treated with DMSO. Data are mean±SEM for HTM 424 donor. (a,b, c=p<0.05 between the different substrates; †=p<0.05 for DMSO versus Lat-B).
Figure 9:
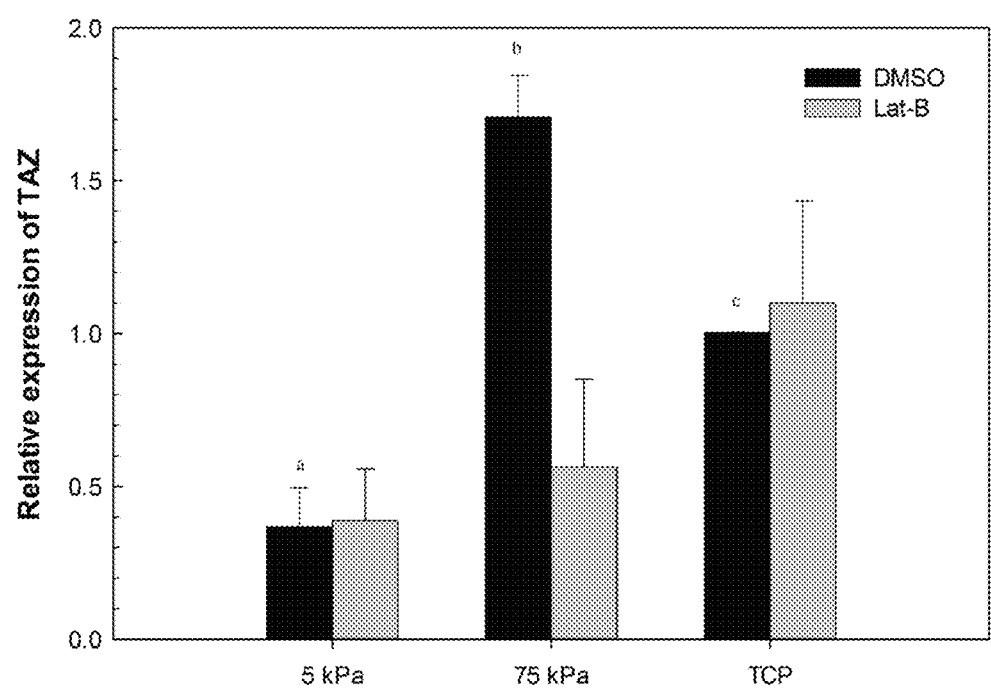
FIG. 9 illustrates that substratum stiffness impacts TAZ mRNA and cellular response to Lat-B treatment in HTM cells. Cells grown on stiff hydrogels and treated with DMSO had significantly different TAZ mRNA expression in comparison to DMSO-treated cells on TCP (>1 GPa) or the more compliant hydrogel. Cells grown on stiff hydrogels and treated with Lat-B from all 3 donors had markedly less TAZ mRNA expression versus treatment with DMSO. Data are mean±SEM for 3 HTM donors. (a,b,c=p<0.05 between the different substrates).

Substratum stiffness alone consistently altered the relative amount of YAP and TAZ mRNA (FIGS. 8 and 9). For all three donors, YAP mRNA was significantly increased in HTM cells grown on the 75 kPa hydrogels in comparison to the 5 kPa hydrogels (Table 1). Even in the least responsive HTM cells (HTM 211) from a 21-year old donor, the 75 kPa hydrogel resulted in a 2.5-fold increase in YAP mRNA in comparison to the 5 kPa hydrogel. TAZ mRNA was 1.7 and 4.6 fold greater on the 75 kPa hydrogels in comparison to TCP and the 5 kPa substrates, respectively (FIG. 9). To ensure that vehicle (DMSO) treatment did not have an appreciable effect on the YAP and TAZ mRNA expression, HTM cells were treated with an equal volume of DPBS without vehicle. The results were similar between the DMSO and the DPBS groups.

TABLE 1

Relative quantitative PCR for YAP mRNA

| | DMSO | | | Lat-B | | |
|---|---|---|---|---|---|---|
| | 211 | 424 | 431 | 211 | 424 | 431 |
| 5 kPa | 0.28 ± 0.02$^a$ | 1.0 ± 0.06$^a$ | 0.85 ± 0.01$^a$ | 0.33 ± 0.01$^a$ | 0.79 ± 0.06$^{a,\dagger}$ | 1.6 ± 0.01$^{a,\dagger}$ |
| 75 kPa | 0.70 ± 0.02$^b$ | 3.0 ± 0.09$^b$ | 5.4 ± 0.11$^b$ | 0.06 ± 0.01$^{b,\dagger}$ | 0.59 ± 0.05$^{a,\dagger}$ | 0.83 ± 0.05$^{b,\dagger}$ |
| TCP | 1.0$^c$ | 1.0$^a$ | 1.0$^c$ | 0.48 ± 0.0$^{c,\dagger}$ | 1.3 ± 0.39$^a$ | 0.55 ± 0.02$^{c,\dagger}$ |

Relative quantification of mean ± SEM YAP mRNA for the HTM 211, 424, and 431 cells when grown on 5 or 75 kPa hydrogels or TCP (>1 GPa) under control conditions (DMSO) or with 2 μM Lat-B.
$^{a,b,c}$For each variable, different subscripts mean significant effect between substrates (P < 0.05).
$^{\dagger}$Statistically significant difference from the YAP mRNA following DMSO or Lat-B treatment (P <0.05).

One hour following treatment with Lat-B, HTM cells on 75 kPa hydrogels produced significantly less YAP mRNA ($p < 0.05$) in all three donors' cells (Table 1). HTM cells grown on 75 kPa hydrogels and treated with Lat-B showed a trend towards less TAZ mRNA in comparison to DMSO-treated cells (P=0.11). In contrast, HTM cells cultured on TCP did not consistently modulate their expression of YAP or TAZ mRNA in response to Lat-B treatment. HTM cells grown on the 5 kPa hydrogels showed no consistent response to Lat-B in terms of YAP and TAZ mRNA, but in general there was little change on these substrates. Variations in response of HTM cells from different donors can occur (Oh et al., 2006; Russell et al., 2008) and this is observed in the present study of YAP with cells from three donors (HTM 211, 424, and 431) that were aged 21, 42, and 43, respectively. However, trends were similar with regard to effects of substratum stiffness and treatment with Lat-B despite variations in the magnitude of YAP expression between the three donors.

Substratum Stiffness & Lat-B Alters CTGF, 14-3-3σ, and PAI-1 Expression.

Figure 10:
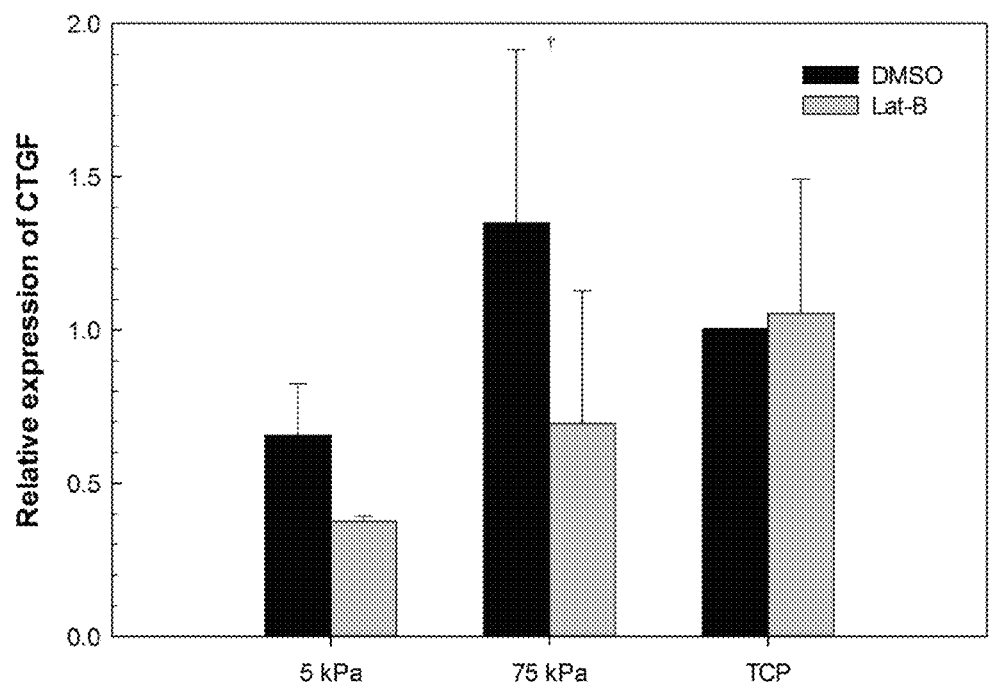
FIG. 10 illustrates that substratum stiffness and Lat-B impacts CTGF mRNA in HTM cells grown on substrates mimicking the stiffness of the glaucomatous HTM. Cells grown on stiff hydrogels and treated with Lat-B had significantly less (p=0.02) CTGF mRNA expression in comparison to DMSO treated cells. For all 3 donors, cells grown on stiff hydrogels had more CTGF mRNA in comparison to the more compliant hydrogels. Data are mean±SEM from 3 HTM donors. (†=p<0.05).
Figure 11:
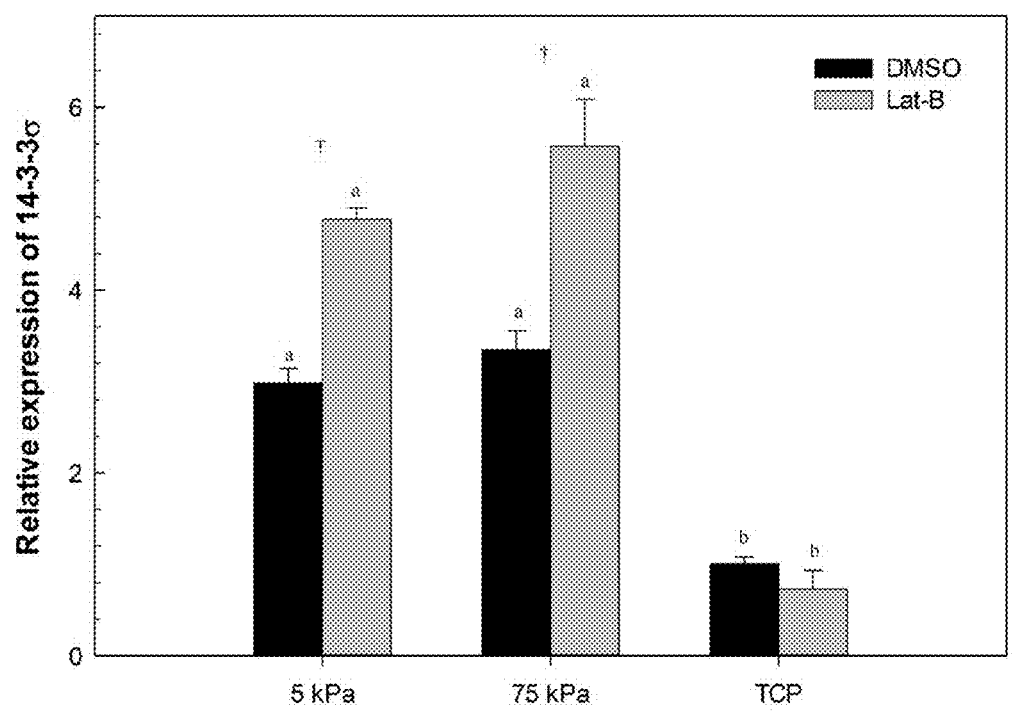
FIG. 11 illustrates that substratum stiffness impacts 14-3-3σ mRNA and cellular response to Lat-B treatment in HTM cells. Cells grown on hydrogels and treated with DMSO had significantly different 14-3-3σ mRNA expression in comparison to DMSO-treated cells on TCP (>1 GPa). Cells grown on hydrogels and treated with Lat-B had significantly more 14-3-3σ mRNA expression versus treatment with DMSO. In contrast, cells grown on TCP and treated with Lat-B did not have significantly different 14-3-3σ mRNA expression versus cells treated with DMSO. Data are mean±SEM for HTM 424 donor. (a,b=p<0.05 between the different substrates; †=p<0.05 for DMSO versus Lat-B).
Figure 12:
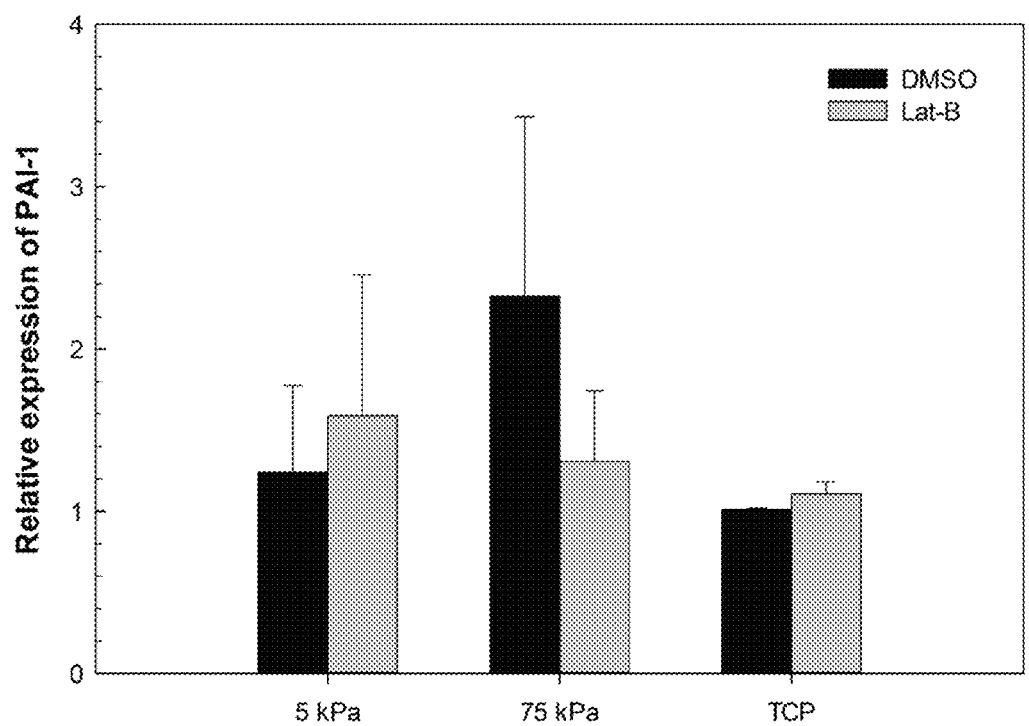
FIG. 12 illustrates that substratum stiffness and Lat-B impacts PAI-1 mRNA in HTM cells. Treatment with Lat-B decreased PAI-1 mRNA expression in comparison to DMSO treatment on the 75 kPa hydrogels for all 3 donors. Data are mean±SEM for 3 HTM donors.

Similar to YAP and/or TAZ, CTGF mRNA was increased in all 3 donors on the 75 kPa hydrogels in comparison to the 5 kPa hydrogels at the one hour time point. In addition, Lat-B significantly decreased CTGF mRNA on the 75 kPa hydrogels (FIG. 10). In contrast, Lat-B treatment markedly increased 14-3-3σ expression on the stiffer hydrogels for all three donors (HTM 211, 424, and 431) in comparison to DMSO treatment (Table 2; FIG. 11). There was a trend towards cells grown on the softer substrates and treated with DMSO having more PAI-1 mRNA expression in comparison to DMSO-treated cells on TCP (FIG. 12). Cells grown on 75 kPa hydrogels and treated with Lat-B had less PAI-1 mRNA expression for all three donors (HTM 424, 211, 553) in comparison to cells treated with DMSO.

TABLE 2

Relative quantitative PCR for 14-3-3σ mRNA.

| | DMSO | | | Lat-B | | |
|---|---|---|---|---|---|---|
| | 211 | 424 | 431 | 211 | 424 | 431 |
| 5 kPa | $15 \pm 0.28^a$ | $3.0 \pm 0.16^a$ | $1.5 \pm 0.15^a$ | $15 \pm 0.82^a$ | $4.8 \pm 0.12^{a,\dagger}$ | $1.09 \pm 0.02^a$ |
| 75 kPa | $18 \pm 0.11^b$ | $3.4 \pm 0.21^a$ | $0.42 \pm 0.05^b$ | $29 \pm 1.8^{b,\dagger}$ | $5.6 \pm 0.51^{a,\dagger}$ | $1.57 \pm 0.11^{b,\dagger}$ |
| TCP | $1.0^c$ | $1.0^b$ | $1.0^a$ | $1.2 \pm 0.25^c$ | $0.73 \pm 0.20^b$ | $0.53 \pm 0.02^{c,\dagger}$ |

Relative quantification of mean ± SEM 14-3-3σ mRNA for the HTM 211, 424, and 431 cells when grown on 5 or 75 kPa hydrogels or TCP (>1 GPa) under control conditions (DMSO) or with 2 μM Lat-B.
$^{a,b,c}$For each variable, different subscripts mean significant effect between substrates (P < 0.05).
$^{\dagger}$Statistically significant difference from the 14-3-3σ mRNA following DMSO or Lat-B treatment (P <0.05).

Substratum Stiffness & Lat-B Alters Localization of YAP.

Figure 13:
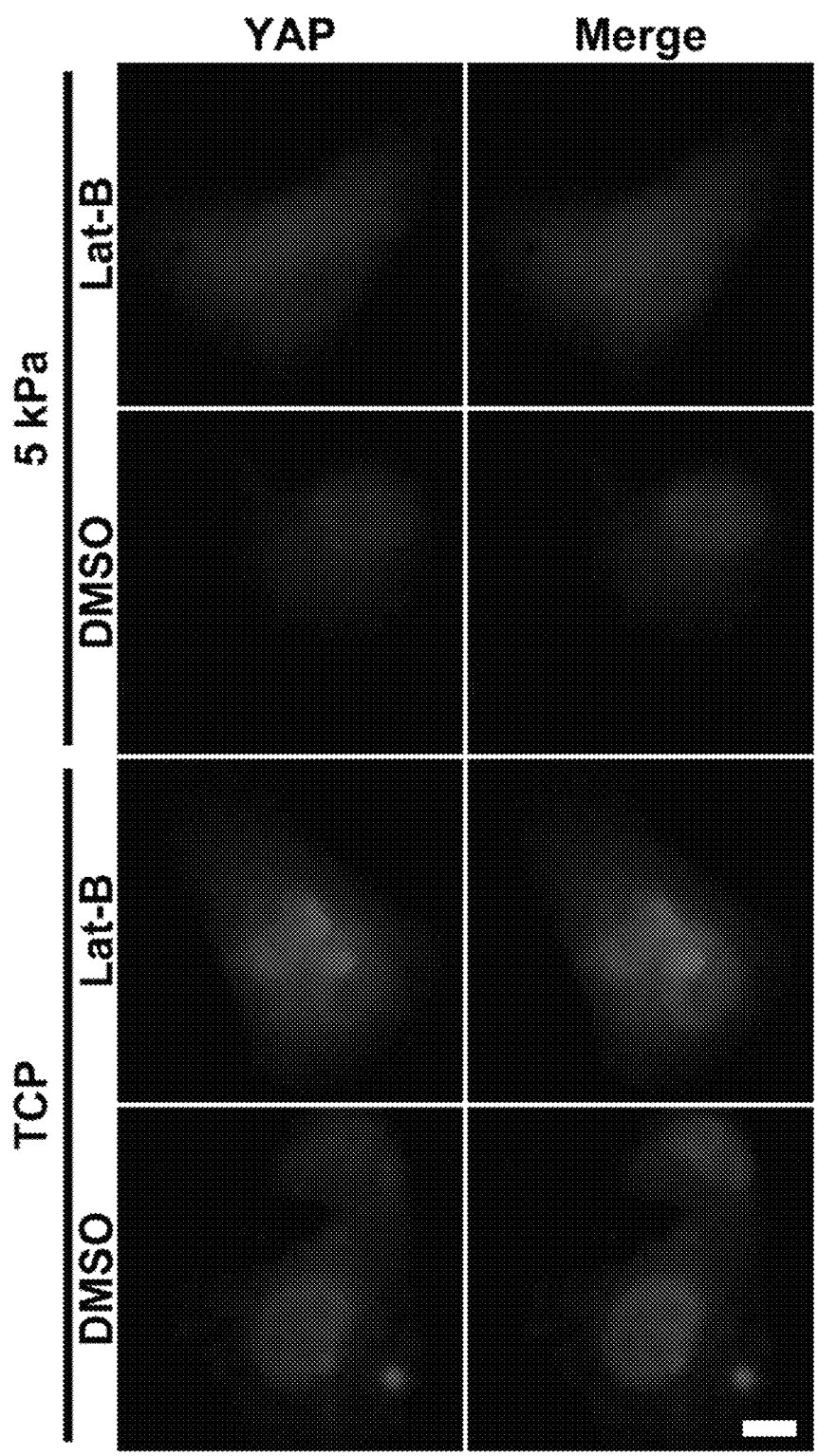
FIG. 13 illustrates that substratum stiffness and Lat-B alters nuclear/cytoplasmic localization in HTM cells. HTM cells stained for YAP (red) and counterstained with DAPI (blue) to identify the nuclei. YAP localization in HTM cells is mixed between nuclear and cytoplasmic. Nuclear localization is more pronounced on TCP (>1 GPa) than on the 5 kPa hydrogel. With Lat-B treatment, nuclear localization is decreased regardless of substrate but the decrease is more pronounced on the 5 kPa hydrogel in comparison to TCP. Scale bar is 10 µm.

Staining of YAP revealed a mix of nuclear and cytoplasmic localizations (FIG. 13). Concomitant with the increased expression of the YAP target gene CTGF on stiffer substrates, cells stained for YAP reveal increased nuclear localization on TCP in comparison to the more compliant 5 kPa hydrogel (FIG. 13, 5 kPa DMSO vs. TCP DMSO). On the 5 kPa hydrogel, Lat-B treatment resulted in a dramatic reduction of YAP in the nucleus (FIG. 13, 5 kPa DMSO vs. Lat-B). On TCP, some nuclear localization remained following Lat B treatment (FIG. 13, TCP DMSO vs. Lat-B) which is consistent with the changes in YAP expression on TCP following Lat-B treatment. A similar trend was observed on the 75 kPa hydrogels.

Discussion

Primary open-angle glaucoma (POAG) is associated with structural changes in the HTM as well as increased resistance to AH outflow in the HTM resulting in elevated IOP (Grant, 1963). Specifically, POAG patients have an accumulation of cross-linked ECM proteins in the TM (Lutjen-Drecoll, 1999; Rohen and Witmer, 1972) such that the extent of ECM deposition in the juxtacanalicular TM correlates with the severity of their optic nerve damage (Gottanka et al., 1997). This increase in cross-linked ECM proteins would result in a stiffening of the HTM, which was recently confirmed with a study demonstrating that the elastic modulus of the HTM increases with glaucoma (Last et al., 2011). There is ample evidence that biophysical stimuli, especially substratum stiffness, profoundly modulate HTM cellular behaviors (Gasiorowski and Russell, 2009; Han et al., 2011; McKee et al., 2011; Schlunck et al., 2008; Thomasy et al., 2012; Wood et al., 2011a; WuDunn, 2009).

The Yorkie-homologues YAP and TAZ are co-activators of transcription that through their participation in the Hippo pathway are important in determining organ size and tumorigenesis (Zhao et al., 2010b). A recent report identified YAP and/or TAZ as nuclear transducers for mechanical cues such as substratum stiffness and cell shape independent of the Hippo/LATS pathway (Dupont et al., 2011). The present example demonstrated that expression of YAP and/or TAZ as well as nuclear localization of YAP are dramatically influenced by substratum compliance in primary HTM cells. YAP and/or TAZ can influence greater than 60 genes in response to changes in substratum stiffness (Dupont et al., 2011) including TGM-2, a calcium-dependent enzyme that is critical to post-translational modification of the ECM via protein cross-linkage. Thus, YAP and/or TAZ may be integral to the progression of glaucoma via further stiffening of the HTM.

Connective tissue growth factor is a member of the CCN family of matricellular regulatory proteins (Ihn, 2002; Phanish et al., 2010) with high constitutive expression in the HTM (Tomarev et al., 2003). Recently, CTGF has been implicated in pseudoexfoliation glaucoma (Browne et al., 2011; Ho et al., 2005) and CTGF overexpression in the mouse eye increased IOP and led to optic nerve damage (Junglas et al., 2012). Similar to YAP and TAZ, cells on hydrogels mimicking the stiffness of the glaucomatous HTM had greater mRNA expression of CTGF in comparison to hydrogels mimicking the normal HTM stiffness, consistent with increased nuclear localization of YAP on stiffer substrates (FIG. 13). This is not surprising given that YAP and TAZ are co-activators of transcription for CTGF as well as transforming growth factor-β (TGF-β), an upstream regulator of CTGF (Junglas et al., 2012). Given that other matricellular genes implicated in glaucoma are markedly altered with substratum stiffness (Thomasy et al., 2012), culturing HTM cells on the 75 kPa hydrogels, a stiffness that approximates that found in glaucomatous HTM, represents an attractive method for conducting in vitro investigations of ECM proteins, their role in glaucoma progression and the impact of therapeutic interventions.

Similar to CTGF, PAI-1 expression also tended to increase on substrates that mimic the stiffness of the glaucomatous HTM. As a serine protease inhibitor, PAI-1 is important in fibrinolysis and also modulates matrix metalloproteinase activity. In glaucoma patients, PAI-1 has been found to be increased in the aqueous humor consistent with the conclusion that PAI-1 may play a role in sclerosis of the juxtacanalicular TM (Dan et al., 2005). A previous study in HTM cells also demonstrated that substratum elasticity modulated PAI-1 gene and protein expression in the presence and absence of TGF-β (Han et al., 2011). Thus, YAP and TAZ could activate transcription and/or translation of PAI-1 directly or mediate its activity indirectly by altering TGF-β expression.

This example also demonstrated that after Lat-B treatment as the HTM cells were reassembling their cytoskeleton, there was a rapid decrease in YAP and TAZ mRNA on hydrogels imitating the stiffness of the glaucomatous HTM (75 kPa), compared to the 5 kPa hydrogels or TCP. In addition, nuclear localization of YAP was markedly decreased on the 5 kPa hydrogels while some nuclear retention of YAP remained on TCP following Lat-B treatment. While Lat-B directly targets the conventional aqueous humor outflow pathway to lower IOP, the exact mechanism by which Lat-B decreases resistance to aqueous outflow within the HTM is unknown. Interestingly, the present example demonstrated that Lat-B increased 14-3-3σ mRNA on the 75 kPA hydrogels but had no effect on the softer substrates. It is an unexpected finding that 14-3-3σ is expressed in HTM cells and is modulated by substratum stiffness. 14-3-3σ is an isoform from a family of highly conserved acidic molecules (Kjarland et al., 2006) important in diverse biologic functions such as stress responses (van Heusden, 2005), transcription (Mhawech, 2005) and protein trafficking (Mhawech, 2005) but the regulatory signaling pathways involving 14-3-3σ proteins are poorly understood. Modulating 14-3-3σ expression may represent a mechanism by which Lat-B can mitigate the transcriptional activity of YAP and TAZ especially on the downstream ECM genes implicated as participating in the onset and/or progression of glaucoma such as CTGF (Thomasy et al., 2012). In addition, 14-3-3σ may represent a potential target for pharmaceutical intervention.

In Example 2 after Lat-B treatment, there were minimal effects on YAP and TAZ expression on hydrogels possessing values for stiffness that mimic the normal HTM. This is consistent with previous studies showing that Lat-B treatment of HTM cells on soft hydrogels, approximating the stiffness of the normal HTM, had a minimal effect on HTM cell morphology and cell elastic modulus in this time frame. In contrast, Lat B treatment dramatically impacted these parameters for cells grown on substrates approximating the stiffness of the glaucomatous HTM as they recover from this drug (McKee et al., 2011; Thomasy et al., 2012). The nearly two fold increase in the modulus of the HTM cells during this recovery phase appears to be highly influential in initiating changes that would appear to be beneficial to the HTM in general. The expression and nuclear localization of YAP and/or TAZ is decreased and this might ultimately cause decreased expression of those genes associated with the transcriptional co-activation by these two proteins.

One of the unexpected results of this example was demonstration that HTM cells grown on TCP had gene expression changes that were not reflective of alterations on the stiffer hydrogels. Thus, hydrogels with stiffness similar to glaucomatous HTM should be a better model for the in vivo condition. The data document the rapid alterations in multiple genes that are occurring during this period when the cell stiffness is altered dramatically in the stiffer hydrogels compared to the softer hydrogels. The TCP results are consistent with the conclusion that the almost four fold increase in stiffness during this critical time of cytoskeleton rearrangement might interfere with cell transcription and might not be insightful for the changes in HTM cells during this time period. Our results also point out that although YAP and/or TAZ might be co-activators of transcription and/or translation of certain genes, other conditions within the cell also influence the eventual levels of gene expression particularly during this time period of very active cytoskeleton assembly. It is also important to note, this example addresses what alterations in gene expression may be occurring in the HTM cells as a result of this transient alteration of the cytoskeleton. While this will influence protein expression on longer timescales, such expression is affected by multiple confounding factors.

In conclusion, YAP and/or TAZ respond to changes in substratum stiffness and influence the expression of genes associated with glaucoma in humans. In addition, Lat-B rapidly decreased YAP and/or TAZ mRNA expression on substrates that had elastic moduli similar to that measured in glaucomatous HTM. Alteration of other genes reported to be increased in glaucoma appeared to reflect the importance of YAP and/or TAZ on their expression. Thus, YAP and/or TAZ may be significantly impacted by Lat-B treatment in the glaucomatous meshwork.

References for Background, Summary, Detailed Description and Example 2

Arocena, M., 2006. Effect of acrylamide on the cytoskeleton and apoptosis of bovine lens epithelial cells. Cell. Biol. Int. 30, 1007-1012.

Bradley, J. M., Kelley, M. J., Zhu, X., Anderssohn, A. M., Alexander, J. P., Acott, T. S., 2001. Effects of mechanical stretching on trabecular matrix metalloproteinases. Invest. Ophthalmol. Vis. Sci. 42, 1505-1513.

Browne, J. G., Ho, S. L., Kane, R., Oliver, N., Clark, A. F., O'Brien, C. J., Crean, J. K., 2011. Connective tissue growth factor is increased in pseudoexfoliation glaucoma. Invest. Ophthalmol. Vis. Sci. 52, 3660-3666.

Dan, J., Belyea, D., Gertner, G., Leshem, I., Lusky, M., Miskin, R., 2005. Plasminogen activator inhibitor-1 in the aqueous humor of patients with and without glaucoma. Arch. Ophthalmol. 123, 220-224.

Dong, J., 2007. Elucidation of a universal size-control mechanism in *Drosophila* and mammals. Cell. 130, 1120-1133.

Dupont, S., Morsut, L., Aragona, M., Enzo, E., Giulitti, S., Cordenonsi, M., Zanconato, F., Le Digabel, J., Forcato, M., Bicciato, S., Elvassore, N., Piccolo, S., 2011. Role of YAP and/or TAZ in mechanotransduction. Nature. 474, 179-183.

Ethier, C. R., Read, A. T., Chan, D. W., 2006. Effects of latrunculin-B on outflow facility and trabecular meshwork structure in human eyes. Invest. Ophthalmol. Vis. Sci. 47, 1991-1998.

Gasiorowski, J. Z., Russell, P., 2009. Biological properties of trabecular meshwork cells. Exp. Eye Res. 88, 671-675.

Gottanka, J., Johnson, D. H., Martus, P., Lutjen-Drecoll, E., 1997. Severity of optic nerve damage in eyes with POAG is correlated with changes in the trabecular meshwork. J. Glaucoma. 6, 123-132.

Grant, W. M., 1963. Experimental aqueous perfusion in enucleated human eyes. Arch. Ophthalmol. 69, 783-801.

Han, H., Wecker, T., Grehn, F., Schlunck, G., 2011. Elasticity-dependent modulation of TGF-beta responses in human trabecular meshwork cells. Invest. Ophthalmol. Vis. Sci. 52, 2889-2896.

Heijl, A., Leske, M. C., Bengtsson, B., Hyman, L., Hussein, M., 2002. Reduction of intraocular pressure and glaucoma progression: results from the Early Manifest Glaucoma Trial. Arch. Ophthalmol. 120, 1268-1279.

Ho, S. L., Dogar, G. F., Wang, J., Crean, J., Wu, Q. D., Oliver, N., Weitz, S., Murray, A., Cleary, P. E., O'Brien, C., 2005. Elevated aqueous humour tissue inhibitor of matrix metalloproteinase-1 and connective tissue growth factor in pseudoexfoliation syndrome. Br. J. Ophthalmol. 89, 169-173.

Ihn, H., 2002. Pathogenesis of fibrosis: role of TGF-beta and CTGF. Curr. Opin. Rheumatol. 14, 681-685.

Junglas, B., Kuespert, S., Seleem, A. A., Struller, T., Ullmann, S., Bosl, M., Bosserhoff, A., Kostler, J., Wagner, R., Tamm, E. R., Fuchshofer, R., 2012. Connective tissue growth factor causes glaucoma by modifying the actin cytoskeleton of the trabecular meshwork. Am. J. Pathol. 180, 2386-2403.

Kaufman, P. L., 2008. Enhancing trabecular outflow by disrupting the actin cytoskeleton, increasing uveoscleral outflow with prostaglandins, and understanding the pathophysiology of presbyopia interrogating Mother Nature: asking why, asking how, recognizing the signs, following the trail. Exp. Eye Res. 86, 3-17.

Kjarland, E., Keen, T. J., Kleppe, R., 2006. Does isoform diversity explain functional differences in the 14-3-3 protein family? Curr. Pharm. Biotechnol. 7, 217-223.

Last, J. A., Pan, T., Ding, Y., Reilly, C. M., Keller, K., Acott, T. S., Fautsch, M. P., Murphy, C. J., Russell, P., 2011. Elastic modulus determination of normal and glaucomatous human trabecular meshwork. Invest. Ophthalmol. Vis. Sci. 52, 2147-2152.

Lutjen-Drecoll, E., 1999. Functional morphology of the trabecular meshwork in primate eyes. Prog. Retin. Eye. Res. 18, 91-119.

McKee, C. T., Wood, J. A., Shah, N. M., Fischer, M. E., Reilly, C. M., Murphy, C. J., Russell, P., 2011. The effect of biophysical attributes of the ocular trabecular meshwork associated with glaucoma on the cell response to therapeutic agents. Biomaterials. 32, 2417-2423.

Mhawech, P., 2005. 14-3-3 proteins—an update. Cell. Res. 15, 228-236.

Miller, E., Yang, J., DeRan, M., Wu, C., Su, A. I., Bonamy, G. M., Liu, J., Peters, E. C., Wu, X., 2012. Identification of serum-derived sphingosine-1-phosphate as a small molecule regulator of YAP. Chem. Biol. 19, 955-962.

Mossbock, G., Weger, M., Faschinger, C., Schmut, O., Renner, W., 2008. Plasminogen activator inhibitor-1 4G/5G gene polymorphism and primary open-angle glaucoma. Mol. Vis. 14, 1240-1244.

Oh, D. J., Martin, J. L., Williams, A. J., Russell, P., Birk, D. E., Rhee, D. J., 2006. Effect of latanoprost on the expression of matrix metalloproteinases and their tissue inhibitors in human trabecular meshwork cells. Invest. Ophthalmol. Vis. Sci. 47, 3887-3895.

Okka, M., Tian, B., Kaufman, P. L., 2004. Effects of latrunculin B on outflow facility, intraocular pressure, corneal thickness, and miotic and accommodative responses to pilocarpine in monkeys. Trans. Am. Ophthalmol. Soc. 102, 251-257; discussion 257-259.

Phanish, M. K., Winn, S. K., Dockrell, M. E., 2010. Connective tissue growth factor-(CTGF, CCN2)—a marker, mediator and therapeutic target for renal fibrosis. Nephron. Exp. Nephrol. 114, e83-92.

Radmacher, M., Tillamnn, R. W., Fritz, M., Gaub, H. E., 1992. From molecules to cells: imaging soft samples with the atomic force microscope. Science. 257, 1900-1905.

Rao, P. V., Deng, P., Sasaki, Y., Epstein, D. L., 2005. Regulation of myosin light chain phosphorylation in the trabecular meshwork: role in aqueous humour outflow facility. Exp. Eye Res. 80, 197-206.

Rao, P. V., Deng, P. F., Kumar, J., Epstein, D. L., 2001. Modulation of aqueous humor outflow facility by the Rho kinase-specific inhibitor Y-27632. Invest. Ophthalmol. Vis. Sci. 42, 1029-1037.

Rhee, D. J., Haddadin, R. I., Kang, M. H., Oh, D. J., 2009. Matricellular proteins in the trabecular meshwork. Exp. Eye Res. 88, 694-703.

Rhee, D. J., Tamm, E. R., Russell, P., 2003. Donor corneoscleral buttons: a new source of trabecular meshwork for research. Exp. Eye Res. 77, 749-756.

Rohen, J. W., Witmer, R., 1972. Electron microscopic studies on the trabecular meshwork in glaucoma simplex. Albrecht. Von Graefes Arch. Klin. Exp. Ophthalmol. 183, 251-266.

Russell, P., Gasiorowski, J. Z., Nealy, P. F., Murphy, C. J., 2008. Response of human trabecular meshwork cells to topographic cues on the nanoscale level. Invest. Ophthalmol. Vis. Sci. 49, 629-635.

Schlunck, G., Han, H., Wecker, T., Kampik, D., Meyer-ter-Vehn, T., Grehn, F., 2008. Substrate rigidity modulates cell matrix interactions and protein expression in human trabecular meshwork cells. Invest. Ophthalmol. Vis. Sci. 49, 262-269.

Spector, I., Shochet, N. R., Blasberger, D., Kashman, Y., 1989. Latrunculins—novel marine macrolides that disrupt microfilament organization and affect cell growth: I. Comparison with cytochalasin D. Cell. Motil. Cytoskeleton. 13, 127-144.

Thomasy, S. M., Wood, J. A., Kass, P. H., Murphy, C. J., Russell, P., 2012. Substratum stiffness and latrunculin B regulate matrix gene and protein expression in human trabecular meshwork cells. Invest. Ophthalmol. Vis. Sci. 53, 952-958.

Tomarev, S. I., Wistow, G., Raymond, V., Dubois, S., Malyukova, I., 2003. Gene expression profile of the human trabecular meshwork: NEIBank sequence tag analysis. Invest. Ophthalmol. Vis. Sci. 44, 2588-2596.

Tovar-Vidales, T., Roque, R., Clark, A. F., Wordinger, R. J., 2008. Tissue transglutaminase expression and activity in normal and glaucomatous human trabecular meshwork cells and tissues. Invest. Ophthalmol. Vis. Sci. 49, 622-628.

Tumminia, S. J., Mitton, K. P., Arora, J., Zelenka, P., Epstein, D. L., Russell, P., 1998. Mechanical stretch alters the actin cytoskeletal network and signal transduction in human trabecular meshwork cells. Invest. Ophthalmol. Vis. Sci. 39, 1361-1371.

van Heusden, G. P., 2005. 14-3-3 proteins: regulators of numerous eukaryotic proteins. IUBMB Life. 57, 623-629.

Wiederholt, M., Thieme, H., Stumpff, F., 2000. The regulation of trabecular meshwork and ciliary muscle contractility. Prog. Retin. Eye Res. 19, 271-295.

Wood, J. A., McKee, C. T., Thomasy, S. M., Fischer, M. E., Shah, N. M., Murphy, C. J., Russell, P., 2011. Substratum compliance regulates human trabecular meshwork cell behaviors and response to latrunculin B. Invest. Ophthalmol. Vis. Sci. 52, 9298-9303.

Wood, J. A., Shah, N. M., McKee, C. T., Hughbanks, M. L., Liliensiek, S. J., Russell, P., Murphy, C. J., 2011b. The role of substratum compliance of hydrogels on vascular endothelial cell behavior. Biomaterials. 32, 5056-5064.

WuDunn, D., 2009. Mechanobiology of trabecular meshwork cells. Exp. Eye Res. 88, 718-723.

Zhao, B., 2008. TEAD mediates YAP-dependent gene induction and growth control. Genes. Dev. 22, 1962-1971.

Zhao, B., Li, L., Guan, K. L., 2010a. Hippo signaling at a glance. J. Cell. Sci. 123, 4001-4006.

Zhao, B., Li, L., Lei, Q., Guan, K. L., 2010b. The Hippo-YAP pathway in organ size control and tumorigenesis: an updated version. Genes. Dev. 24, 862-874.

Example 3

Substratum Stiffness, Wnt Pathway, and Gene Silencing

Example 3 provides further information on substratum stiffness and its relation to YAP and/or TAZ related genes and proteins in the HTM. Furthermore, Example 3 elucidates the relation between the Wnt pathway and YAP and/or TAZ. In addition, Example 3 shows that silencing YAP and TAZ in the HTM causes an alteration in gene and protein expression in HTM cells. This example includes both empirical data that were collected from actual experiments (described in past tense), and expected data that can be obtained by one skilled in the art using the proposed experiments (described in present tense).

Materials and Methods

Materials and methods similar to those in Examples 1 and 2 were used. Alternatively or additionally, at least some of the following methods were or can be used for the experiments described hereafter.

Cell Culture.

Primary HTM cells is obtained from normal human donor corneoscleral rims deemed not suitable for transplant (50). HTM cells are cultured in DMEM/F12 medium with 10% fetal bovine serum. Only cells before the $7^{th}$ passage are used to conduct these studies. Only normal HTM cells are used because growth of cells from glaucomatous HTM is generally not robust enough to guarantee a successful completion of the experiment (51-54). Cells are plated onto hydrogels with Young's moduli of 5 kPa (homeomimetic) or 75 kPa (pathomimetic) that are fabricated to fit in a single well of a standard 6 well culture plate with 300,000 cells per surface. The cells are allowed to attach to the surfaces for 24 hours prior to subsequent experimentation.

Fabrication of Hydrogel Substrates.

Hydrogels are composed of 5.8% acrylamide/0.2% bisacrylamide (5 kPa) or 17.4% acrylamide/0.6% bisacrylamide (75 kPa). Each of the gels contains 4% (v/v) acrylamidoisopropyl trimethyl ammonium chloride. After polymerization, the gels are stored in phosphate buffered saline for two days to allow maximal swelling. One day prior to seeding of the cells on the hydrogels, culture medium with 10% fetal bovine serum is added to the gel to allow the hydrogel to be coated with the various proteins and components present in the serum. The Young's moduli of the hydrogels have been validated by atomic force microscopy (14, 55).

Real-Time PCR.

Real-time PCR is conducted with 70 ng of mRNA using a StepOne PCR machine. Reverse transcription is done for 30 minutes at 50° C. and subsequent PCR is done for 40 cycles of 15 seconds at 95° C. and 1 minute at 60° C.

Transfection of Primary HTM Cells with siRNA.

At 60-80% confluence of HTM cells, siRNA transfections is completed using the DharmaFect 4 transfection reagent (Dharmacon, Lafayette, Colo.) following the manufacturer's instructions with a final concentration of 28.5 nM of siRNA or control siRNA (ON-TARGETplus Non-targeting siRNA #3, Dharmacon). About 48 h after transfection, cells are harvested for RNA isolation. Knockdown to expression levels below 20% is achieved as determined by real-time qPCR analyses.

Western Blotting.

After growth of HTM cells on homeomimetic or pathomimetic hydrogels, cells are lysed with M-PER® Mammalian Protein Extraction Reagent containing phosphatase and protease inhibitors or with the ProteoExtract Cytoskeleton Enrichment and Isolation Kit, and the lysate is collected into 1.5 ml Eppendorf tubes. Removal of insoluble cellular debris is performed by centrifugation at maximum speed (14K rpm) in a tabletop microcentrifuge for 5 minutes; supernatants are collected into fresh tubes. Equivalent volumes of protein samples are loaded onto a NuPAGE® Bis-Tris Pre-Cast gel after mixing with loading buffer and denaturation by boiling. Gel electrophoresis is performed at 140 V for 1 hr followed by transfer to nitrocellulose at 35 V for 45 minutes. The nitrocellulose membrane is blocked for 1 hr at room temperature in Milk Diluent Blocking Concentrate diluted 1:10 in ultrapure water prior to incubating with primary antibody. After overnight incubation with primary antibody, the membrane is washed and incubated with appropriate secondary antibody for one hour. The membrane is washed again and developed with chemiluminescent probes.

Immunocytochemistry.

Cells are seeded onto hydrogels and after 72 hours in experimental medium, cells are washed 3 times in 1×PBS, then fixed with 4% formaldehyde in 1×PBS for 10 minutes. Following three additional 1×PBS washes, the cells are permeabilized with 0.1% Triton X-100 for 10 minutes. Blocking is performed with 1% bovine serum albumin (BSA) in 1×PBS for 30 minutes at room temperature. The samples are then incubated with antibody in 1% BSA at room temperature for 60 minutes. Cells are washed 3 times with 1×PBS before incubation with Alexa 488-conjugated antibody at 1:400 in 1% BSA at room temperature in the dark for 30 minutes. Cell nuclei are stained for 10 minutes at room temperature in the dark with 4',6-diamidino-2-phenylindole (DAPI). Finally, the cells are left in 1×PBS until immunofluorescent imaging with a Zeiss Axiovert 200M epifluorescence microscope.

Organ Culture and RNA Silencing.

Perfused anterior segment organ culture and Lentiviral-shRNA silencing can be conducted as previously detailed (42-49). Briefly, anterior segments, comprised of the cornea, trabecular meshwork and approximately 10 mm of sclera, is dissected from postmortem human eyes and the ciliary body and iris carefully removed. The anterior segments are clamped tightly into a standard flow cell. In a culture incubator maintained at 37° C., 5% $CO_2$ and 100% humidity, serum-free Dulbecco's modified Eagle medium (DMEM) with 1% penicillin-streptomycin-Fungizone and intermediate glucose levels is perfused at a constant pressure of 8.8 mm Hg; flow rates, which average between 1 and 7 μl/min, is determined gravimetrically. After flow rates have stabilized, usually 1-2 days, $10^8$ pfu of lentivirus, containing shRNA for YAP, TAZ or non-targeted control is added to the perfusion chambers by media exchange and flow rates measured for several additional days. In some cases, the pressure head then is increased to 2× and flow rates measured for several additional days to assess the effects of silencing on the ability to mount a homeostatic response to pressure elevation. At the end of the perfusion experiments, anterior segments is removed and portions used for immunohistochemical analysis, while the TM is removed from other portions and used for qPCR assessment of specific mRNA levels or Western immunoblot assessment of specific protein levels. Some wedges is also used to evaluate cellular and structural integrity by H & E staining of 5 μm radial sections.

Replication of Lentivirus.

Replication incompetent lentivirus is generated in the 293FT cell line (Invitrogen). The 293FT cells are maintained in DMEM containing 10% fetal calf serum, 4 mM glutamine, 1 mM Minimal Essential Medium (MEM) sodium pyruvate, 0.1 mM MEM non-essential amino acids, 1% penicillin-streptomycin and 500 μg/ml Geneticin (Invitrogen). The pLenti expression plasmid (3 μg) containing the silencing cassette are co-transfected with ViraPower packaging mix (9 μg) into 293FT cells using Lipofectamine 2000 (Invitrogen). Lipofectamine-DNA complexes are incubated overnight with the 293FT cells and then replaced with DMEM containing the above supplements without Geneticin. Lentiviral-containing supernatants are harvested 72 hours post-transfection and centrifuged at 3,000 rpm for 10 minutes to pellet cell debris. Viral supernatants are then aliquoted and stored at −80° C. until use.

Effectiveness of shRNA Silencing.

To determine viral titers and assess effectiveness of shRNA silencing, various dilutions of lentivirus (ranging from $10^{-2}$ to $10^{-6}$) in DMEM+10% FCS are added to TM cells in culture with 1:1000 dilution of Polybrene (Sigma). Virus are replaced by complete medium the following day and the selection agent, blasticidin (1 μg/ml), is added to cultures 48 hours after infection. After 5 days, adherent cells are washed 3 times in phosphate buffered saline (PBS) and stained with 1% crystal violet for 10 minutes. Cells are washed 3 times in PBS and the number of stained plaques counted for each lentiviral dilution. Titers are determined in this manner for each silencing lentivirus, including the ineffective shRNA control.

Results

Substratum Compliance and YAP and TAZ

Figure 14:
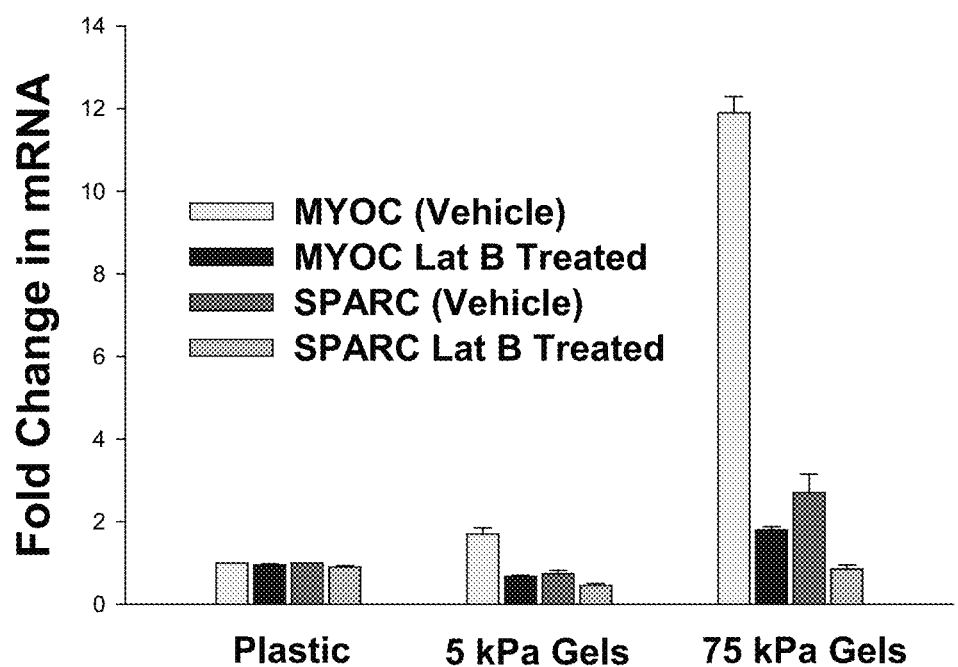
FIG. 14 illustrates that Latrunculin B modulates the mRNA expression of Myocilin and SPARC. Myocilin mRNA was significantly increased in HTM cells cultured on 5 kPa and 75 kPa hydrogels compared to cells cultured on tissue culture plastic (TCP, GPa). Myocilin levels were increased greater than 12 fold in cells cultured on the stiffer gels. SPARC expression was lower on the 5 kPa hydrogels when compared to TCP, but was higher on the stiffer gels compared to TCP. Addition of Latrunculin B significantly decreased expression of both mRNAs on the hydrogels; however, there was no change in either mRNA on TCP. This demonstrates that vastly different results can be obtained performing experiments on substrates with non-physiological values and highlights the need to conduct experiments on substrates with biomimetic compliance values. Experiments performed with biomimetic substrates will better predict the effect of therapeutics obtained in vivo.

We determined the effects of Latrunculin B (Lat B), a drug currently in clinical trials for reducing IOP on HTM cells grown on homeomimetic and pathomimetic substrates (FIG. 14). Prior to addition of the drug, myocilin (MYOC) mRNA expression was seven fold higher on pathomimetic hydrogels compared to homeomimetic hydrogels. SPARC (serine protein, acidic, rich in cysteine) was increased about 3.6 fold on the stiffer pathomimetic hydrogels. The SPARC knockout mouse was recently reported to have reduced IOP (15) consistent with the conclusion that SPARC is involved in outflow resistance. When Lat B was added to the culture medium for 30 minutes followed by a seven hours recovery, MYOC and SPARC mRNA levels were significantly reduced on both homeo- and pathomimetic hydrogels. Cells grown on tissue culture plastic (GigaPascal (GPa) compliance value) showed no change in MYOC or SPARC mRNA levels after Lat B treatment.

As shown above in FIG. 14, the protein SPARC was elevated approximately 4 fold on pathomimetic hydrogels compared to the homeomimetic ones, which could cause increased IOP. The addition of Lat B to HTM cells on both hydrogels significantly reduced the levels of SPARC. Also, our results indicated that after Lat B treatment, HTM cells had decreased mRNA levels of YAP and TAZ by 1.8 fold and 1.9 fold respectively. Again, these results showed the actions of Lat B extend beyond the known interaction with actin.

Figure 15:
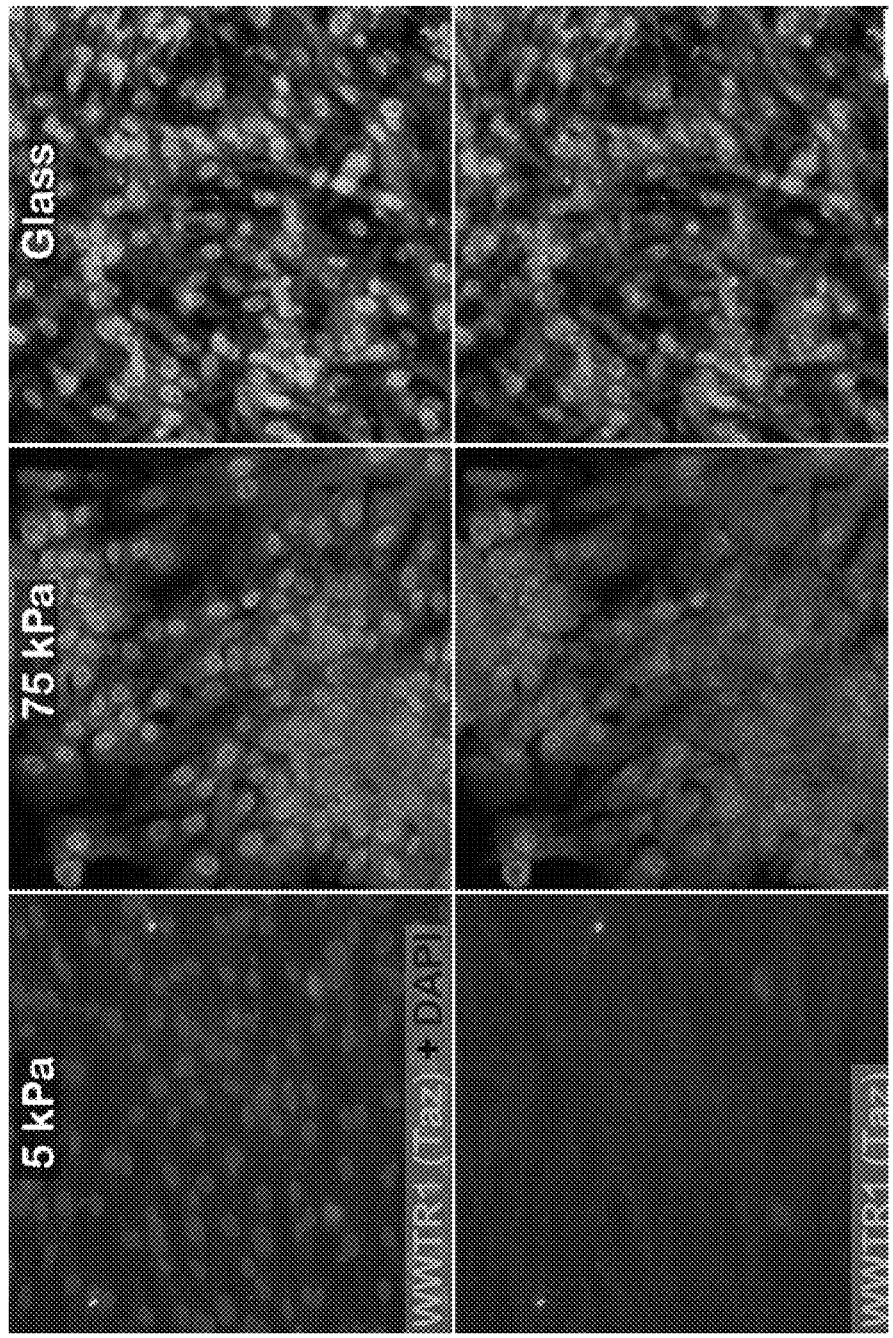
FIG. 15 illustrates that substratum stiffness affects spatial localization of TAZ in HTM Cells. HTM cells were plated onto 5 kPa and 75 kPa hydrogels and on glass substrates. The cells were fixed, permeabilized and stained with an antibody to TAZ as well as stained with DAPI to visualize the cell nucleus. TAZ staining in the cells on the softer hydrogel was cytoplasmic and diffuse. On the stiffer hydrogels, TAZ staining was visible in the cytoplasm but also was localized and expressed in the nucleus. In HTM cells cultured on glass, TAZ expression was increased in the nucleus of the cell. These data demonstrate increased nuclear localization of TAZ in cells cultured on stiffer substrates, which is consistent with published reports. Immunofluorescence was captured for the same time period for all images. An increase of TAZ in the nucleus should increase expression of genes upregulated in glaucoma. Bar=50 µm.

TAZ in the HTM cells on the stiffer pathomimetic substrates had increased levels of nuclear staining compared to HTM cells on the softer homeomimetic hydrogels (FIG. 15). There was more nuclear localization of TAZ in HTM cells on glass (>1 GPa) compared to the cells on hydrogels.

Figure 16:
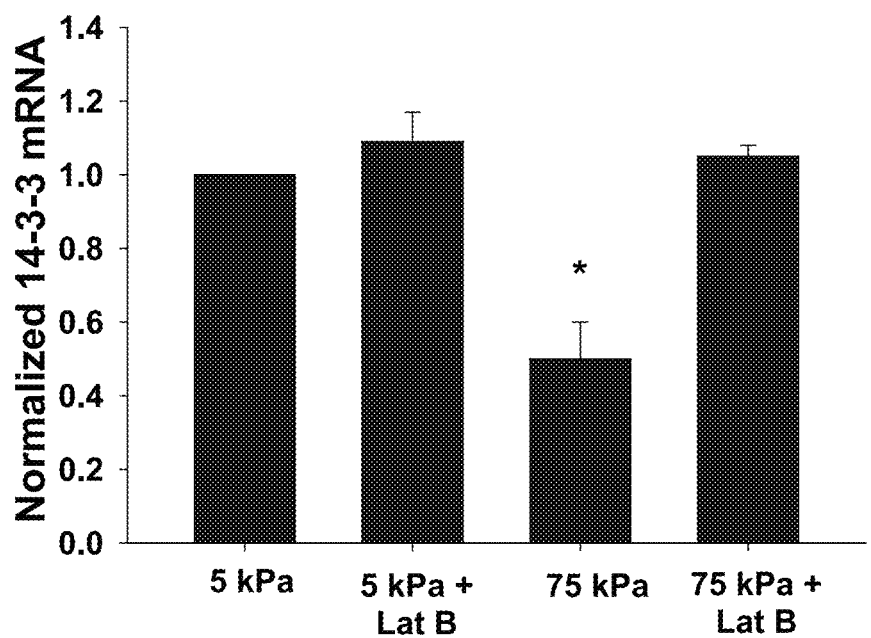
FIG. 16 illustrates that the amount of 14-3-3σ mRNA varies with substrate stiffness and is modulated by Latrunculin B. The amount of 14-3-3σ mRNA in cells cultured on stiffer hydrogels is one half the level in cells cultured on homeomimetic hydrogels. When Latrunculin B was added, the level of 14-3-3σ mRNA in the HTM cells on the stiffer hydrogels doubled; however, the drug had no effect on cells cultured on the softer hydrogels. Decreased levels of 14-3-3σ in cells on the stiffer hydrogels lead to a decrease in the YAP and TAZ targeted for degradation. These data point out the importance of performing experiments on biomimetic substrates.

The mRNA level of 14-3-3σ on the pathomimetic hydrogels was reduced 50% compared to control homeomimetic hydrogels (FIG. 16). The amount of 14-3-3σ in the HTM cells could influence the amount of YAP and/or TAZ targeted for degradation. Downregulation of 14-3-3σ would allow more TAZ to bind to Dvl thereby disrupting the Wnt pathway. After treatment with Lat B, the mRNA levels of 14-3-3σ increased on the pathomimetic hydrogels so that cells on both hydrogels had similar amounts of mRNA.

Data showed that cells treated for three days with $10^{-7}$M dexamethasone (DEX) on homeomimetic surfaces evidenced no change in transglutaminase 2 mRNA levels, but on pathomimetic surfaces the mRNA levels increased from 1.3±0.13 fold to 1.7±0.01 (relative to homeomimetic hydrogels).

The Wnt Pathway in HTM Cells is Modified by YAP and TAZ

Figure 17:
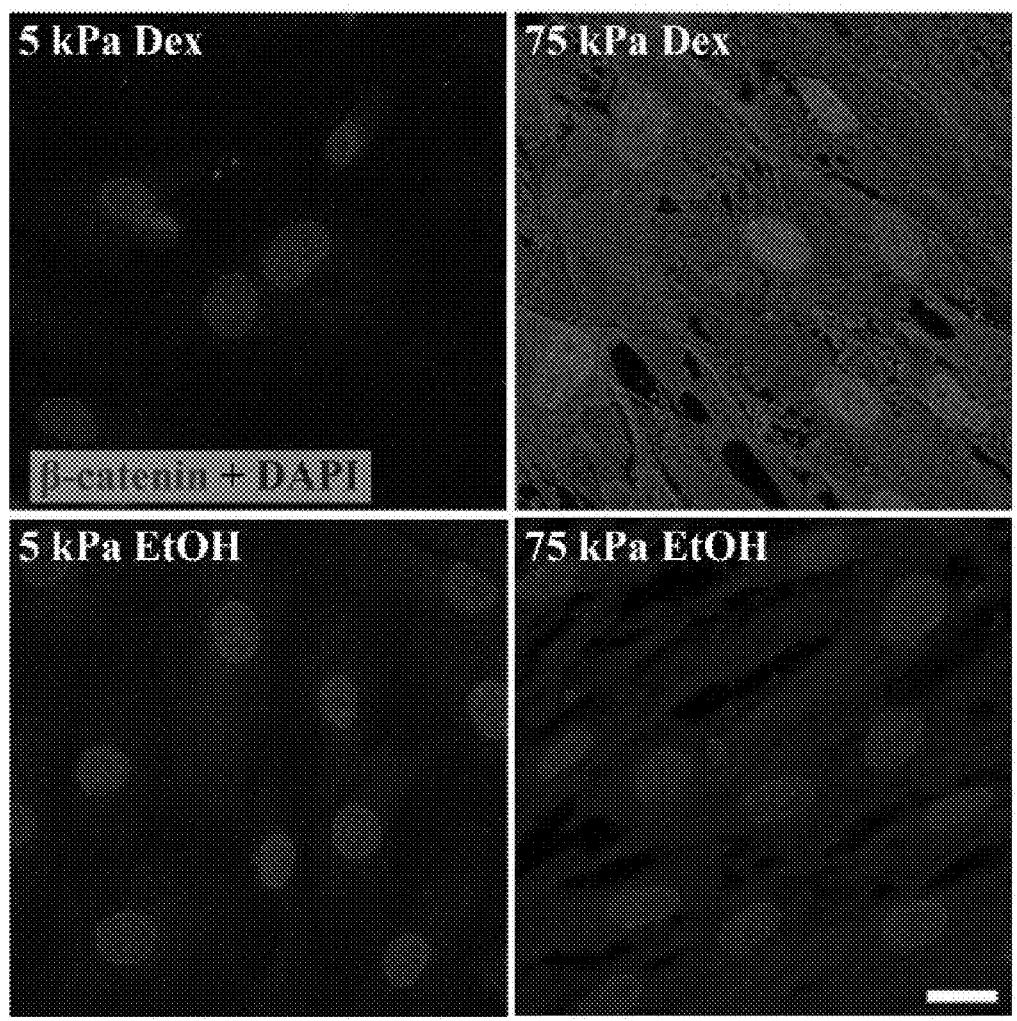
FIG. 17 illustrates that immunostaining of phosphorylated β-Catenin in HTM cells is increased on pathomimetic hydrogels after treatment with Dexamethasone. HTM cells were treated with vehicle (EtOH) or $10^{-7}$M dexamethasone for three days. Cells cultured on the homeomimetic and pathomimetic hydrogels were then fixed, permeabilized and stained with an antibody to phosphorylated β-catenin. Cells were also stained with DAPI to reveal the nucleus. Immunofluorescence was captured with the same settings for all images. The cells on the pathomimetic hydrogels treated with vehicle alone had increased levels of staining compared to the homeomimetic gels. After treatment with dexamethasone, there appeared to be a slight decrease in phosphorylated β-catenin in the cells on the homeomimetic gels, but a large increase on the pathomimetic gels. These data are consistent with the conclusion that a dysregulation of the Wnt pathway on the stiffer hydrogels after dexamethasone treatment. Bar=20 µm.

Data using an antibody to phosphorylated β-catenin showed low levels of β-catenin immunofluorescence in HTM cells on homeomimetic and pathomimetic substrates (FIG. 17). There was more staining in the cells on the pathomimetic hydrogel consistent with the increased expression of the TAZ mRNA on the stiffer gels. The increased TAZ could associate with Dvl and result in more phosphorylation of β-catenin. After dexamethasone treatment of HTM cells on the homeomimetic gels, there could be a slight reduction in the phosphorylated form of β-catenin. In cells on the pathomimetic gels after treatment of HTM cells with dexamethasone, there was a large increase of phospho-β-catenin immunofluorescence.

Silencing YAP and TAZ in the HTM

Figure 18:
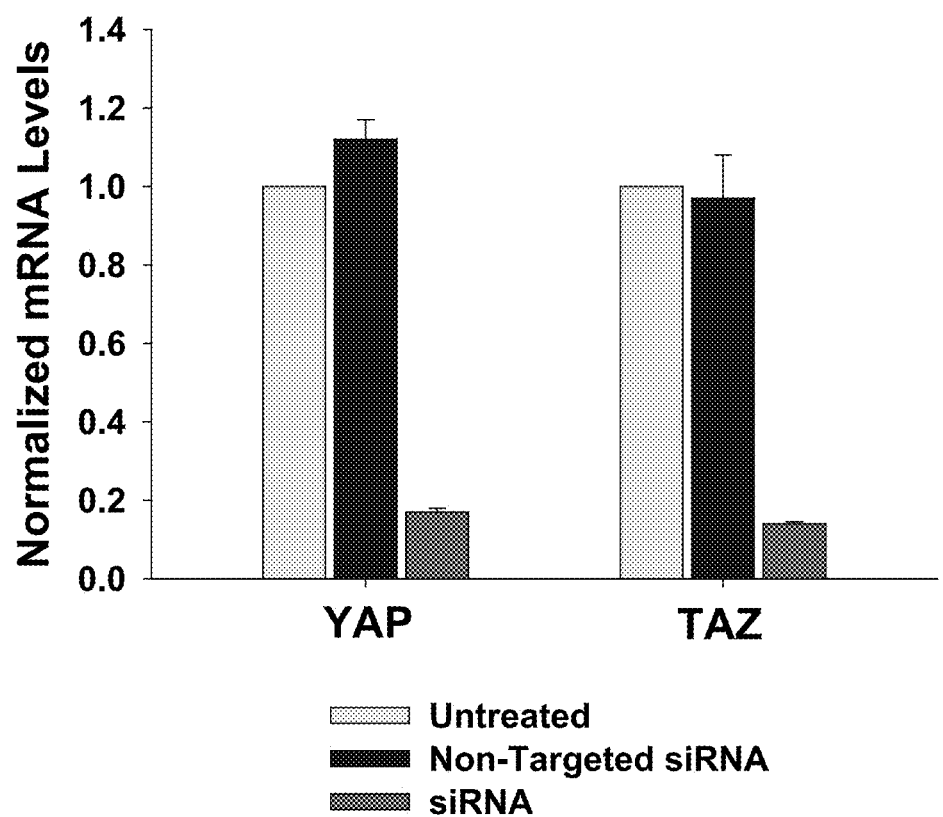
FIG. 18 illustrates that YAP and TAZ can be silenced in primary human trabecular cells. Using the Dharmacon protocol, HTM cells were left untreated, treated with a non-targeting siRNA or siRNA specific to YAP or TAZ. After 48 hours, the mRNA was extracted from the cells using the RNeasy protocol and the levels of YAP and TAZ mRNA were determined by qPCR. In both cases, the mRNA level was lower in the cells silenced for YAP or TAZ. YAP was 17%±0.01 of the level in the untreated cells. The non-targeted siRNA had a value of 112%±0.05. For TAZ, the value for the targeted siRNA was 14%±0.003 compared to the untreated cells. The non-targeted siRNA had a value of 97%±0.11.

We used mRNA silencing of YAP and TAZ to determine changes in gene and protein expression of the genes directly influenced by these co-activators of transcription. HTM cells grown of homeomimetic and pathomimetic substrates were used. Data in FIG. 18 showed that we successfully silenced YAP and TAZ in primary HTM cells. With both YAP and TAZ, we achieved around 80% gene silencing up to forty-eight hours after addition of the siRNA to our primary HTM cells. We used the Dharmacon silencing procedure since we found this was far superior to the Qiagen protocol (~60% silencing).

Figure 19:
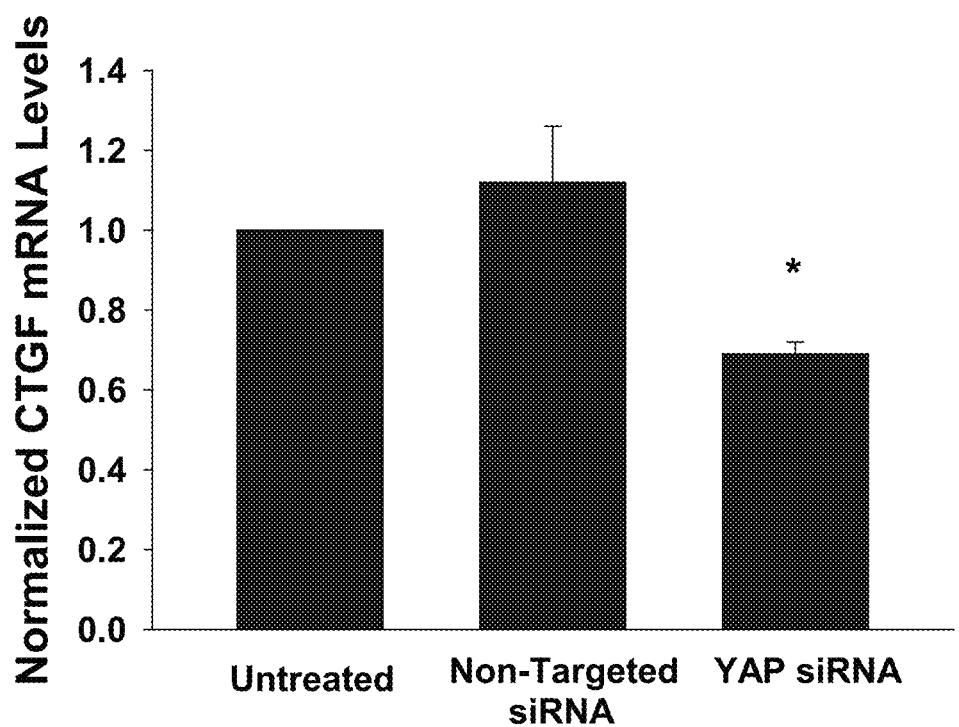
FIG. 19 illustrates that connective tissue growth factor mRNA is downregulated in cells that have YAP mRNA silenced. The mRNA levels of CTGF were significantly reduced in cells that had YAP mRNA silenced compared with untreated cells. The mRNAs extracted from the silencing experiment described in FIG. 7 were checked for levels of CTGF by qPCR. The amount of CTGF in the silenced cells was 69% of the untreated cells. Use of a non-targeted siRNA did not influence the level of CTGF mRNA.

With silencing, the level of CTGF was significantly reduced (p=0.006) in the HTM cells (FIG. 19). This result is consistent with the YAP and/or TAZ co-activating transcription and/or translation of this mRNA as has been previously reported (16). Levels of CTGF were similar in both the untreated cells as well as the cells treated with the non-targeted siRNA. This data indicate that the effects of the transfection protocol did not influence the levels of CTGF directly. Only when the siRNA for YAP was used did the level of CTGF decrease. Levels of TGF-β, transglutaminase 2, serpine 1, and thrombospondin can also be measured in the same series of experiments.

Figure 20:
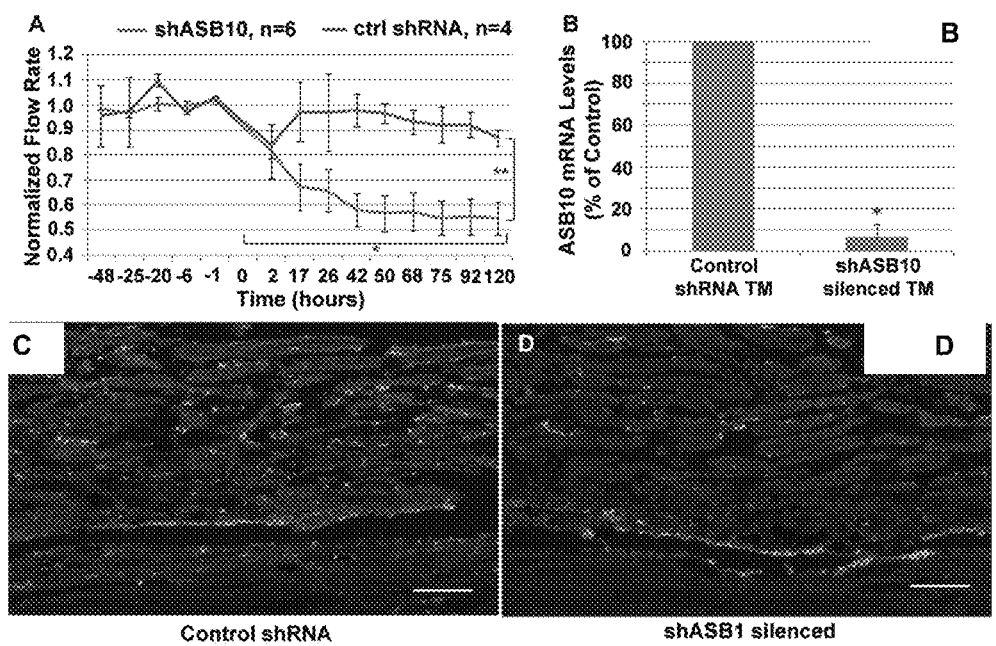
FIGS. 20A-D illustrate the effects of shASB10 (ankyrin repeats and suppressor of cytokine signaling box-containing protein 10) expression on outflow facility in human anterior segment perfusion culture. (A) shASB10 or control shRNA lentivirus was applied to human anterior segments in perfusion culture at time point 0. The number of replicates is shown. Error bars represent the standard error of the mean. Outflow facility was measured for a further 5 days. *$p=0.002$ flow rates just prior to application versus at 120 hours as determined by a paired Student's t-test. **$p=0.01$ control shRNA versus shASB10 by an unpaired Student's t-test. (B) Quantitative RT-PCR of ASB10 mRNA levels in TM tissue extracts after outflow experiments. ASB10 mRNA levels were reduced approximately 95% in shASB10-infected TM (n=5) as compared to control infected TM (n=3). *$p=0.02$ as determined by an unpaired Students t-test. (C, D) ASB10 immunostaining (red) of tissue post-silencing of control (C) and shASB10-infected (D) TM. Fibronectin (green) was used as a counter-stain in both images. The confocal settings were identical for each image and the images were representative of 5 shASB10-infected eyes and 3 controls. DAPI was used to stain the nuclei blue. These data show that silencing of specific mRNAs can influence outflow and can be successfully measured with human anterior segment perfusion culture. Scale bars=20 µm.

Our data showed that inhibiting the mRNA of ankyrin repeats and suppressor of cytokine signaling box-containing protein 10 (ASB10) reduced outflow facility by 50% (42) (FIG. 20).

Discussion

Substratum Compliance and YAP and TAZ

HTM cells on substrates with the compliances of glaucomatous HTM (pathomimetic) have altered location and expression of the mechanotransducers YAP and TAZ compared to normal HTM (homeomimetic).

Alterations in the composition and organization of the basement membrane modulate the surface topography and local stiffness that are fundamental biophysical attributes of the microenvironment of the HTM cell. We created substrates that mimic the vastly different values for compliance found in the normal and glaucomatous meshworks and documented that HTM cell behavior is profoundly modulated by the compliance of the substratum (14). According to the data in FIG. 14, the use of substrates with moduli similar to the compliance of tissues quantified in vivo (kPa) can reveal information not capable of being obtained by growth of cells on tissue culture plastic with moduli in the GPa range. Our data demonstrate the action of Lat B is not solely on the actin cytoskeletal network but also is involved in the alteration of gene expression.

The exact mechanistic pathway leading to the initiation and progression of glaucoma remains unknown. Although the prime event that initiates glaucoma is not currently known, we believe that modulation of YAP and/or TAZ is very close to this initiating cause. Alterations in the ECM surrounding the HTM cells would increase the levels of YAP and/or TAZ in the nucleus. The change in the location of YAP and/or TAZ can then increase the levels of proteins such as transglutaminase 2, which is directly involved in cross-linking of the ECM creating a less compliant or stiffer substrate. This alteration in ECM compliance can be one of the first steps in the initiation and development of glaucoma. We note that increased TGF-β and CTGF as a result of nuclear YAP and/or TAZ also foster the disease process. Thus, YAP and/or TAZ become candidates for therapeutic intervention at an early stage in the disease.

One or more embodiments involve YAP and/or TAZ in later stages or the progression of the disease following increased stiffness of the tissue. At this point, the actions of YAP and/or TAZ serve as a positive regulator to induce additional changes to the matrix and enhance the stiffening of the tissue. Regardless of the point in the disease, the actions of YAP and/or TAZ create a profound change in the HTM. The determination of the role of these two proteins can reveal novel targets for intervention in this disease.

TAZ in the HTM cells on the stiffer pathomimetic substrates had increased levels of nuclear staining compared to HTM cells on the softer homeomimetic hydrogels (FIG. 15). This is consistent with a previous report showing increased nuclear localization of YAP and/or TAZ on stiffer substrates (16). Our data shows that these co-activators of transcription would induce gene expression that would further increase the stiffness of the HTM. For example, increased transglutaminase 2 would lead to crosslinking and stiffening in the HTM. Other alterations in gene expression generated by these proteins are consistent with the profile of proteins localized to glaucomatous HTM.

The differences in cellular response as a result of interacting with substrates having different values of compliance can be readily seen in FIG. 14. Our results highlight the necessity for using the appropriate substrates with biomimetic compliances in vitro to improve the likelihood of the data obtained being predictive of the in vivo condition.

FIG. 15 showed that YAP and/or TAZ had increased nuclear localization on the pathomimetic hydrogels. The localization of YAP and/or TAZ influences the expression of other proteins believed to be involved in glaucoma in the HTM cells. Using similar design as described above, one skilled in the art can perform experiments to investigate alterations in TGF-β, CTGF, serpine 1, transglutaminase 2 and thromobospondin as a consequence of the changes in substrate stiffness. Studies can define the relationship between glucocorticoids, substrate stiffness and the actions of YAP and/or TAZ. By enumerating the changes to the proteins listed above, one can discern how glucocorticoids influence the normal HTM and elucidate their involvement on the raised IOP observed in some individuals.

We expect changes in the expression levels and cellular localization of YAP and/or TAZ on the different hydrogels as well as with different treatments of DEX or Lat B. We also expect changes in the proteins related to glaucoma as a result of changes in the location of the YAP and/or TAZ. Modulation of the concentrations of DEX and Lat B can vary the response of certain mRNA or protein expression levels. Clearly changes in the cytoskeleton influence the cell nucleus and recent data from our laboratory showed morphological alterations in the cell nucleus as well as to nuclear scaffolding proteins such as nesprins with alterations in cytoskeletal dynamics. Alterations to the cell nucleus lead to alterations in levels of gene expression as well.

The Wnt Pathway in HTM Cells is Modified by YAP and TAZ

Previous studied reported that sFRP1 was overexpressed in glaucoma and overexpression led to an increase in IOP in mice (41). Since TAZ can bind with Dvl, the Wnt pathway can be disrupted by increased TAZ in the cytoplasm. Besides the external interference of sFRP1 with the pathway, intracellular disruption of the pathway can also occur as a result of TAZ. Substrate compliance affected the amount of TAZ. Our results with HTM cells on homeomimetic gels show 46% less TAZ mRNA expression than in cells on the pathomimetic gels. This result shows that there are more TAZ in cells on stiffer substrates that may interact with the Dvl protein and potentially antagonize the Wnt pathway. The effects of YAP and/or TAZ on the Wnt pathway can be observed by monitoring the level of phosphorylation of β-catenin (FIG. 1). Increased phosphorylation results in the degradation of β-catenin indicating a disrupted Wnt pathway.

There was more staining in the cells on the pathomimetic hydrogel consistent with the increased expression of the TAZ mRNA on the stiffer gels (FIG. 17). In cells on the pathomimetic gels after treatment of HTM cells with dexamethasone, there was a large increase of phospho-β-catenin immunofluorescence. These results pointed to differential effects of dexamethasone as a direct result of compliance itself. The data are consistent with the conclusion that a disruption of the Wnt pathway on the pathomimetic hydrogels and a substantially deactivated Wnt pathway when glucocorticoids were added to HTM cells.

Lat B may also act on the Wnt pathway. We reported above our initial findings that YAP and TAZ levels change as a result of Lat B treatment. Determining how the changes in the levels of YAP and/or TAZ influence the Wnt pathway can give additional insight into the effects of this pathway in glaucoma. One can investigate changes in the amount of β-catenin, β-catenin phosphorylation and localization to fully assess the effects on the Wnt pathway. One can determine mRNA levels using qPCR and follow protein levels with Western blots and immunofluorescence. From previously reported work, the Wnt pathway clearly impacts IOP and can be an element in the initiation and progression of POAG.

There is disruption of the Wnt pathway as a result of alterations of YAP and/or TAZ. Substrate compliance and Lat B alter the expression of these proteins and thereby directly impact the Wnt pathway. One can alter the drug concentration to establish a correct dose response in the HTM cells. Changes in 14-3-3σ influence the degradation of YAP and/or TAZ and thereby protect Dvl and the Wnt pathway. Experiments to test these issues can use cells from a minimum of three donors and increase the number of donors if no clear trend developed. Measurements of β-catenin mRNA with qPCR, Western blotting and immunofluorescence can be used to assess proteins in the Wnt pathway in cultured HTM cells.

Silencing YAP and TAZ in the HTM

Silencing YAP and TAZ in the HTM causes an alteration in gene and protein expression in HTM cells and dramatically influences HTM function. As shown above, gene and protein expression in HTM cells is directed by substrate compliance.

Using the techniques applied in FIG. 19 and FIG. 20, one skilled in the art can measure outflow in the normal corneoscleral rims before and after addition of either YAP or TAZ shRNA or a non-targeted shRNA. One can deliver the shRNA using a lentivirus construct associated with the data of FIG. 20. After termination of the organ perfusion, the HTM is dissected from the button and the mRNA levels for CTGF, TGF-β, transglutaminase 2, serpine 1, and thrombospondin is determined. These experiments are novel because they are directed at proteins, YAP and TAZ in the HTM, which have not been considered previously as involved in glaucoma. These studies can verify the influence of YAP and/or TAZ on the function of the trabecular meshwork. One can use anterior segments from normal individuals. In order to understand the importance of YAP and/or TAZ on glaucoma, the function that these proteins play in the normal outflow pathway must be delineated.

To further test the effect of shRNA silencing, complementary 21 nucleotide shRNA sets as developed and tested earlier can be annealed to generate double-stranded (ds) DNA oligonucleotides and cloned into the pENTR/U6 vector using T4 ligase (Invitrogen). The resulting silencing cassette contains a human U6 promoter, the shRNA ds oligonucleotides and an RNA polymerase III terminator, all the elements required for RNA polymerase III-controlled expression of the silencing shRNA. Correct sequences is confirmed by DNA sequencing. The shRNA cassette is transferred into the pLenti6/BLOCK-iT-DEST vector by recombination using the Gateway LR clonase II enzyme (Invitrogen). This vector contains modified HIV-1 5' and 3' long terminal repeats and a HIV-1 psi sequence for viral packaging but the VSV-G gene from vesicular stomatitis virus is used in place of the HIV-1 envelope glycoprotein. The pLenti6 silencing vector is transformed into OneShot Stbl3 *E. coli* and purified using the Endo-free Plasmid Maxiprep kit (Qiagen, Valencia, Calif.).

Silencing YAP or TAZ can directly impact the mRNA levels of the five genes identified above. A differential response can be associated with varying substrate compliance (homeomimetic versus pathomimetic). If a change in the outflow as a result of the silencing is not observed, one can deplete the kinases that phosphorylate YAP and/or TAZ specifically LATS1 and 2. These kinases have been shown to be depleted when 17-allylamino-17-demethoxygelanamycin is added to cell cultures (34). This drug directly inhibits heat shock protein 90 with subsequent depletion of the kinases. Our data are consistent with the conclusion 25 nM of the drug reduced the amount of HSP90 by 50% accompanied by increased expression of YAP in HTM cells. One can check the levels of LATS 1 and 2 using Western blotting to verify that the drug does indeed deplete these kinases from the HTM. With depletion of the kinases, the degradation of YAP and/or TAZ is inhibited and the levels of these proteins should increase. If the proteins remain in the nucleus, they co-activate factors related to glaucoma. If they remain in the cytoplasm, the Wnt pathway is down regulated. Under either of these conditions, outflow decreases, which is an indicator that YAP and/or TAZ are directly involved with IOP regulation.

References for Example 3

1. Quigley, H. A., and A. T. Broman. 2006. The number of people with glaucoma worldwide in 2010 and 2020. Br J Ophthalmol 90:262-267.
2. Johnstone, M. A., and W. M. Grant. 1973. Pressure-dependent changes in structure of the aqueous outflow system of human and monkey eyes. Am J Ophthalmol. 365-383.
3. Johnson, M. 2006. 'What controls aqueous humour outflow resistance?'. Exp Eye Res 82:545-557.
4. The, A. I. 2000. The Advanced Glaucoma Intervention Study (AGIS): 7. the relationship between control of intraocular pressure and visual field deterioration. Am J Ophthalmol. 429-440.
5. Collaborative Normal-Tension Glaucoma Study, G. 1998. Comparison of glaucomatous progression between untreated patients with normal-tension glaucomaa and patients with therapeutically reduced intraocular pressures. Am J Ophthalmol 487-497.
6. Heijl, A., M. C. Leske, B. Bengtsson, L. Hyman, and M. Hussein. 2002. For the Early Manifest Glaucoma Trial Group: reduction of intraocular pressure and glaucoma progression. Arch Ophthalmol 1268-1279.
7. Last, J. A., T. Pan, Y. Ding, C. M. Reilly, K. Keller, T. S. Acott, M. P. Fautsch, C. J. Murphy, and P. Russell. 2011. Elastic Modulus Determination of Normal and Glaucomatous Human Trabecular Meshwork. Invest Ophthalmol Vis Sci 52:2147-2152.
8. Tovar-Vidales, T., R. Roque, A. F. Clark, and R. J. Wordinger. 2008. Tissue transglutaminase expression and activity in normal and glaucomatous human trabecular meshwork cells and tissues. Invest Ophthalmol Vis Sci 49:622-628.
9. Xue, W., R. Wallin, E. A. Olmsted-Davis, and T. Borras. 2006. Matrix GLA protein function in human trabecular meshwork cells: inhibition of BMP2-induced calcification process. Invest Ophthalmol Vis Sci 47:997-1007.
10. Borras, T., and N. Comes. 2009. Evidence for a calcification process in the trabecular meshwork. Exp Eye Res 88:738-746.
11. Rohen, J. W., E. Lutjen-Drecoll, C. Flugel, M. Meyer, and I. Grierson. 1993. Ultrastructure of the trabecular meshwork in untreated cases of primary open-angle glaucoma (POAG). Exp Eye Res 56:683-692.
12. Lutjen-Drecoll, E. 2005. Morphological changes in glaucomatous eyes and the role of TGFbeta2 for the pathogenesis of the disease. Exp Eye Res 81:1-4.
13. Gottanka, J., D. H. Johnson, P. Martus, and E. Lutjen-Drecoll. 1997. Severity of optic nerve damage in eyes with POAG is correlated with changes in the trabecular meshwork. J Glaucoma 6:123-132.
14. McKee, C. T., J. A. Wood, N. M. Shah, M. E. Fischer, C. M. Reilly, C. J. Murphy, and P. Russell. 2011. The effect of biophysical attributes of the ocular trabecular meshwork associated with glaucoma on the cell response to therapeutic agents. Biomaterials 32:2417-2423.
15. Haddadin, R. I., D. J. Oh, M. H. Kang, T. Filippopoulos, M. Gupta, L. Hart, E. H. Sage, and D. J. Rhee. 2009. SPARC-null Mice Exhibit Lower Intraocular Pressures. Invest Ophthalmol Vis Sci 50:3771-3777.
16. Dupont, S., L. Morsut, M. Aragona, E. Enzo, S. Giulitti, M. Cordenonsi, F. Zanconato, J. Le Digabel, M. Forcato, S. Bicciato, N. Elvassore, and S. Piccolo. 2011. Role of YAP and/or TAZ in mechanotransduction. Nature 474:179-183.
17. Zhao, B., L. Li, Q. Lei, and K. L. Guan. 2010. The Hippo-YAP pathway in organ size control and tumorigenesis: an updated version. Genes Dev 24:862-874.
18. Gulshan, K., S. S. Lee, and W. S. Moye-Rowley. 2011. Differential oxidant tolerance determined by the key transcription factor Yap1 is controlled by levels of the Yap1-binding protein, Ybp1. J Biol Chem 286:34071-34081.
19. Orumets, K., K. Kevvai, I. Nisamedtinov, T. Tamm, and T. Paalme. 2011. YAP1 over-expression in *Saccharomyces cerevisiae* enhances glutathione accumulation at its biosynthesis and substrate availability levels. Biotech J In Press
20. Qi, H., Y. Han, and J. Rong. 2011. Potential roles of PI3K/Akt and Nrf2-Keap1 pathways in regulating hormesis of Z-ligustilide in PC12 cells against oxygen and glucose deprivation. Neuropharmacology In Press.
21. Zhao, B., L. Li, and K. L. Guan. 2010. Hippo signaling at a glance. J Cell Sci 123:4001-4006.
22. Varelas, X., R. Sakuma, P. Samavarchi-Tehrani, R. Peerani, B. M. Rao, J. Dembowy, M. B. Yaffe, P. W. Zandstra, and J. L. Wrana. 2008. TAZ controls Smad nucleocytoplasmic shuttling and regulates human embryonic stem-cell self-renewal. Nature Cell Bio 10:837-848.
23. Varelas, X., P. Samavarchi-Tehrani, M. Narimatsu, A. Weiss, K. Cockburn, B. G. Larsen, J. Rossant, and J. L. Wrana. 2010. The Crumbs complex couples cell density sensing to Hippo-dependent control of the TGF-beta-SMAD pathway. Dev Cell 19:831-844.
24. Picht, G., U. Welge-Luessen, F. Grehn, and E. Lutjen-Drecoll. 2001. Transforming growth factor beta 2 levels in the aqueous humor in different types of glaucoma and the relation to filtering bleb development. Graefes Arch Clin Exp Ophthalmol 239:199-207.
25. Rohen, J. W., E. Lutjen-Drecoll, C. Flugel, M. Meyer, and I. Grierson. 1993. Ultrastructure of the trabecular meshwork in untreated cases of primary open-angle glaucoma (POAG). Exp Eye Res 56:683-692.
26. Welge-Lussen, U., C. A. May, and E. Lutjen-Drecoll. 2000. Induction of tissue transglutaminase in the trabecular meshwork by TGF-beta1 and TGF-beta2. Invest Ophthalmol Vis Sci 41:2229-2238.
27. Flugel-Koch, C., A. Ohlmann, R. Fuchshofer, U. Welge-Lussen, and E. R. Tamm. 2004. Thrombospondin-1 in the trabecular meshwork: localization in normal and glaucomatous eyes, and induction by TGF-beta1 and dexamethasone in vitro. Exp Eye Res 79:649-663.
28. Tovar-Vidales, T., A. F. Clark, and R. J. Wordinger. 2011. Transforming growth factor-beta2 utilizes the canonical Smad-signaling pathway to regulate tissue transglutaminase expression in human trabecular meshwork cells. Exp Eye Res 93:442-451.
29. Sethi, A., A. Jain, G. S. Zode, R. J. Wordinger, and A. F. Clark. 2011. Role of TGFbeta/Smad signaling in gremlin induction of human trabecular meshwork extracellular matrix proteins. Invest Ophthalmol Vis Sci 52:5251-5259.
30. Chudgar, S. M., P. Deng, R. Maddala, D. L. Epstein, and P. V. Rao. 2006. Regulation of connective tissue growth factor expression in the aqueous humor outflow pathway. Mol Vis 12:1117-1126.
31. Browne, J. G., S. L. Ho, R. Kane, N. Oliver, A. F. Clark, C. J. O'Brien, and J. K. Crean. 2011. Connective tissue growth factor is increased in pseudoexfoliation glaucoma. Invest Ophthalmol Vis Sci 52:3660-3666.
32. Junglas, B., A. H. Yu, U. Welge-Lussen, E. R. Tamm, and R. Fuchshofer. 2009. Connective tissue growth factor induces extracellular matrix deposition in human trabecular meshwork cells. Exp Eye Res 88:1065-1075.
33. Luna, C., G. Li, P. B. Liton, D. L. Epstein, and P. Gonzalez. 2009. Alterations in gene expression induced by cyclic mechanical stress in trabecular meshwork cells. Mol Vis 15:534-544.
34. Huntoon, C. J., M. D. Nye, L. Geng, K. L. Peterson, K. S. Flatten, P. Haluska, S. H. Kaufmann, and L. M. Karnitz. 2010. Heat shock protein 90 inhibition depletes LATS1 and LATS2, two regulators of the mammalian hippo tumor suppressor pathway. Cancer Res 70:8642-8650.
35. Remue, E., K. Meerschaert, T. Oka, C. Boucherie, J. Vandekerckhove, M. Sudol, and J. Gettemans. 2010. TAZ interacts with zonula occludens-1 and -2 proteins in a PDZ-1 dependent manner. FEBS Lett 584:4175-4180.
36. Teo, J. L., and M. Kahn. 2010. The Wnt signaling pathway in cellular proliferation and differentiation: A tale of two coactivators. Adv Drug Del Rev 62:1149-1155.
37. Freese, J. L., D. Pino, and S. J. Pleasure. 2010. Wnt signaling in development and disease. Neurobio Dis 38:148-153.
38. Hergovich, A., and B. A. Hemmings. 2010. TAZ-mediated crosstalk between Wnt and Hippo signaling. Develop Cell 18:508-509.
39. Varelas, X., B. W. Miller, R. Sopko, S. Song, A. Gregorieff, F. A. Fellouse, R. Sakuma, T. Pawson, W. Hunziker, H. McNeill, J. L. Wrana, and L. Attisano. 2010. The Hippo pathway regulates Wnt/beta-catenin signaling. Develop Cell 18:579-591.
40. Shyam, R., X. Shen, B. Y. Yue, and K. K. Wentz-Hunter. 2010. Wnt gene expression in human trabecular meshwork cells. Mol Vis 16:122-129.
41. Wang, W. H., L. G. McNatt, I. H. Pang, J. C. Millar, P. E. Hellberg, M. H. Hellberg, H. T. Steely, J. S. Rubin, J. H. Fingert, V. C. Sheffield, E. M. Stone, and A. F. Clark. 2008. Increased expression of the WNT antagonist sFRP-1 in glaucoma elevates intraocular pressure. J Clin Invest 118:1056-1064.
42. Pasutto, F., K. E. Keller, N. Weisschuh, H. Sticht, J. R. Samples, Y. F. Yang, M. Zenkel, U. Schlotzer-Schrehardt, C. Y. Mardin, P. Frezzotti, B. Edmunds, P. L. Kramer, E. Gramer, A. Reis, T. S. Acott, and M. K. Wirtz. 2011 Variants in ASB10 are associated with open-angle glaucoma. Human Mol Gen In Press.
43. Acott, T. S., P. D. Kingsley, J. R. Samples, and E. M. Van Buskirk. 1988. Human trabecular meshwork organ culture: morphology and glycosaminoglycan synthesis. Invest Ophthalmol Vis Sci 29:90-100.
44. Bradley, J. M., M. J. Kelley, X. Zhu, A. M. Anderssohn, J. P. Alexander, and T. S. Acott. 2001. Effects of mechanical stretching on trabecular matrix metalloproteinases. Invest Ophthalmol Vis Sci 42:1505-1513.
45. Bradley, J. M., J. Vranka, C. M. Colvis, D. M. Conger, J. P. Alexander, A. S. Fisk, J. R. Samples, and T. S. Acott. 1998. Effect of matrix metalloproteinases activity on outflow in perfused human organ culture. Invest Ophthalmol Vis Sci 39:2649-2658.
46. Keller, K. E., J. M. Bradley, and T. S. Acott. 2009. Differential effects of ADAMTS-1, -4, and -5 in the trabecular meshwork. Invest Ophthalmol Vis Sci 50:5769-5777.
47. Keller, K. E., J. M. Bradley, M. J. Kelley, and T. S. Acott. 2008. Effects of modifiers of glycosaminoglycan biosynthesis on outflow facility in perfusion culture. Invest Ophthalmol Vis Sci 49:2495-2505.

48. Keller, K. E., J. M. Bradley, J. A. Vranka, and T. S. Acott. 2011. Segmental versican expression in the trabecular meshwork and involvement in outflow facility. Invest Ophthalmol Vis Sci 52:5049-5057.
49. Keller, K. E., M. J. Kelley, and T. S. Acott. 2007. Extracellular matrix gene alternative splicing by trabecular meshwork cells in response to mechanical stretching. Invest Ophthalmol Vis Sci 48:1164-1172.
50. Rhee, D. J., E. R. Tamm, and P. Russell. 2003. Donor corneoscleral buttons: a new source of trabecular meshwork for research. Exp Eye Res 77:749-756.
51. Tschumper, R. C., and D. H. Johnson. 1990. Trabecular meshwork cellularity. Differences between fellow eyes. Invest Ophthalmol Vis Sci 31:1327-1331.
52. Caballero, M., P. B. Liton, D. L. Epstein, and P. Gonzalez. 2003. Proteasome inhibition by chronic oxidative stress in human trabecular meshwork cells. Biochem Biophys Res Commun 308:346-352.
53. Yu, A. L., R. Fuchshofer, A. Kampik, and U. Welge-Lussen. 2008. Effects of oxidative stress in trabecular meshwork cells are reduced by prostaglandin analogues. Invest Ophthalmol Vis Sci 49:4872-4880.
54. Gasiorowski, J. Z., and P. Russell. 2009. Biological properties of trabecular meshwork cells. Exp Eye Res 88:671-675.
55. Wood, J. A., N. M. Shah, C. T. McKee, M. L. Hughbanks, S. J. Liliensiek, P. Russell, and C. J. Murphy. 2011. The role of substratum compliance of hydrogels on vascular endothelial cell behavior. Biomaterials 32:5056-5064.

Example 4

YAP Translocation in Human Trabecular Meshwork Cells

Objective:

Yes-associated protein (YAP) is a transcriptional co-activator and a component of the Hippo pathway. It is only transcriptionally active while in the nucleus, and can be sequestered in the cytoplasm for degradation. Little is known about YAP in ocular tissue with the current literature primarily focusing on its role in organ size control, tumorigenesis, and proliferation. Glaucoma, a major cause of irreversible blindness, has been associated with loss of cellularity in the human trabecular meshwork (HTM). Additionally, soluble cytoactive factors are known to be altered in the aqueous humor of patients with glaucoma. Serum, used for cell culture in vitro, is a rich reservoir of soluble factors and its presence has a direct impact on various cellular functions such as proliferation, migration and stress response. Previous research has demonstrated that serum starvation induces YAP phosphorylation and cytoplasmic retention across a range of immortalized cell lines, and that nuclear localization can be induced with serum. In order to better understand the regulation of this important proliferative pathway in HTM cells, we investigated the role of serum-induced YAP regulation by examining the expression and localization of YAP in SV40 immortalized HTM cells (TM-1) and primary (HTM) cells.

Methods:

TM-1 cells and HTM cells from normal donors were cultured in DMEM containing 10% fetal bovine serum. They were then serum starved for 24 hours and then treated with either 10% serum containing media or serum free media as a control. The treatment lasted for 3 hours, after which they were fixed in and immuno-stained for YAP. YAP localization was then determined using immunofluorescence microscopy. Additionally, we serum starved the primaries for extended periods (1-8 days) before fixation and staining.

Figure 21:
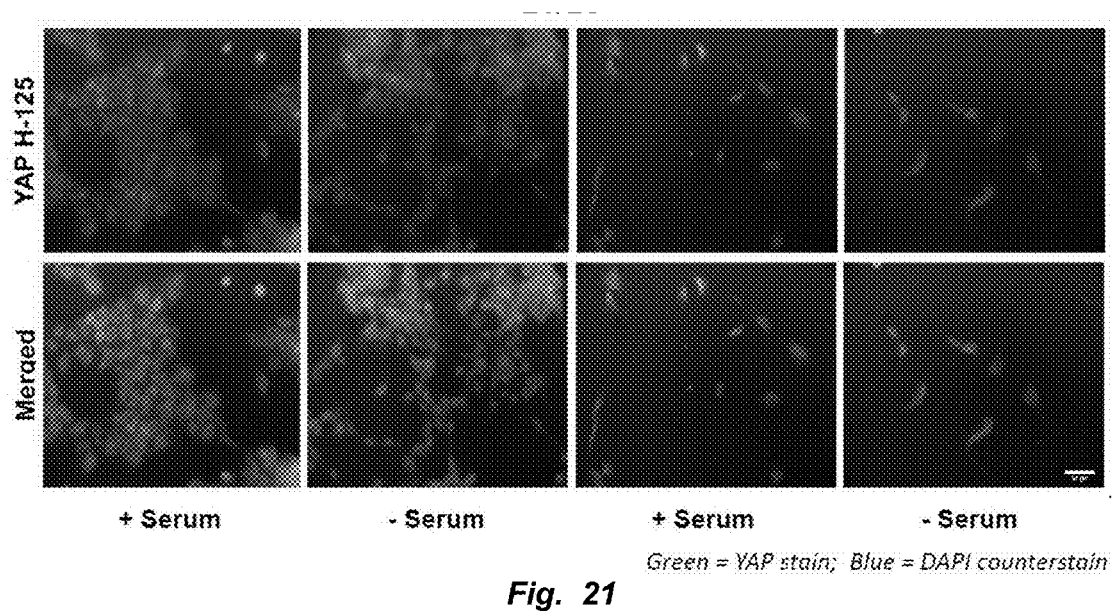
FIG. 21 illustrates that in immortalized HTM cells (TM-1) cells, 24-hour serum starvation induces cytoplasmic retention of YAP, which is reactivated after 6-hour serum treatment.
Figure 22:
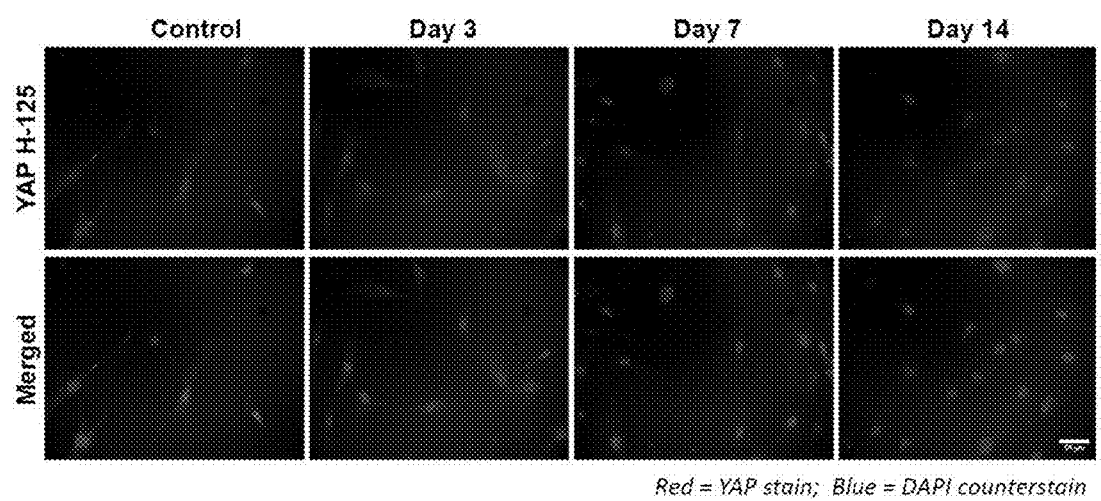
FIG. 22 illustrates that in primary HTM cells, YAP nuclear localization is observed even after prolonged serum-free conditions.
Figure 23:
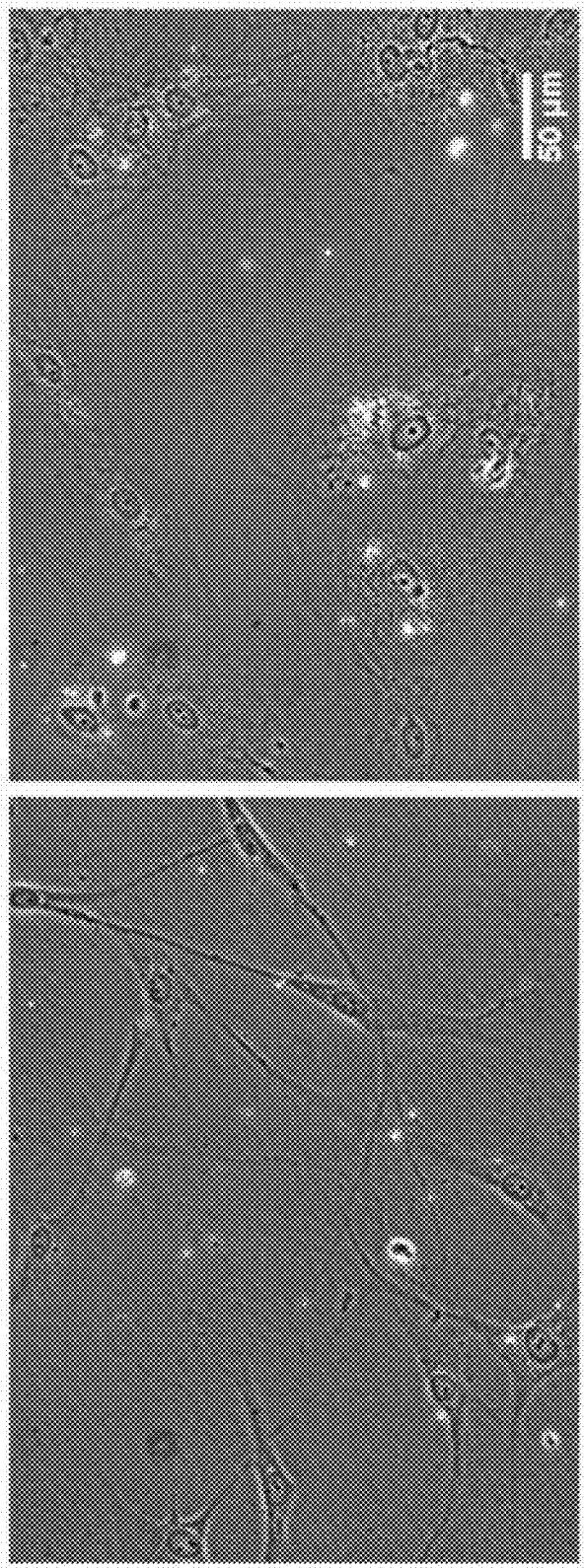
FIG. 23 illustrates that primary HTM cells demonstrate a change in morphology but otherwise remain viable after prolonged serum starvation.

Results:

In control (serum-free) TM-1 cells, YAP localized predominantly to the cytoplasm. With serum treatment, the TM-1 cells exhibited strong YAP nuclear localization. Primary HTM cells demonstrated nuclear localization of YAP in both the presence and absence of serum. To confirm if this was a lingering effect of serum during initial culture, we also fixed and stained HTM cells at 1, 4, 6, and 8 days. At all timepoints, primary HTM cells exhibited strong nuclear localization of YAP. Conclusions: The serum-starved TM-1 cells are consistent with previous reports of cytoplasmic retention of YAP and provide further evidence for YAP nuclear translocation following serum treatment. These results demonstrate that there are serum-derived factors that modulate the activation of YAP in TM-1 cells. Furthermore, these results indicate that this is not the dominant regulatory mechanism in primary HTM cells in vitro. Additional research will investigate the significance of YAP nuclear localization in HTM cells under serum-free conditions in vitro. Such differences are critical in considering choices of cell type for investigating signaling pathways pertaining to glaucoma or other diseases. Overall, these results provide insight on the function of YAP in the HTM and have broader implications in the study of glaucoma. The results are depicted in FIGS. 21-23.

In summary, immortalized HTM cells (TM-1) demonstrated cytoplasmic retention of YAP in serum starved conditions. The addition of serum induced YAP nuclear localization. Serum-free conditions did not elicit the same effect in primary HTM cell lines, where YAP nuclear localization was consistent even after prolonged exposure. These results point to the importance of examining primary cell lines and are consistent with the conclusion that there are mechanisms involved in HTM cell mechanotransduction that are not replicable in immortalized cell lines.

References for Example 4

Dupont S, et al. (2011) Role of YAP/TAZ in mechanotransduction. Nature 474:179-83.
Last J A, et al. (2011) Elastic modulus determination of normal and glaucomatous human trabecular meshwork. IOVS 52:2147-2152.
Wood J A, et al. (2011) Substratum compliance regulates human trabecular meshwork cell behaviors and response to latrunculin B. IOVS 52:9298-9303.
Yu F, et al. (2012) Regulation of the Hippo-YAP pathway by G-protein-coupled receptor signaling. Cell 150:780-91.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising an agent that inhibits the function of Yes-associated protein (YAP) transcriptional co-activator/transcriptional co-activator with PDZ binding motif (TAZ) formulated for ophthalmic administration, wherein the composition is formulated for administration to the eye via a route selected from the group consisting of topical, application to the eyelids, application to the conjunctival sac and intravitreous injection, wherein the composition is formulated in a form selected from the group consisting of a viscous solution, a suspension, an ointment, a small pellet to be placed under the eyelids, and a fine powder, wherein the agent is selected from the group consisting of dobutamine (CAS#34368-04-2), HSP90 inhibiting geldanamycin analogue 17-DMAG (CAS#467214-21-7), HSP90 inhibiting geldanamycin analogue 17-AAG (CAS#75747-14-7), HSP90 inhibitor STA-9090 (CAS#: 888216-25-9), HSP90 inhibitor NVP-HSP990 (CAS#934343-74-5), porphyrin family member verteporfin (CAS#129497-78-5), Ki16425 (CAS#355025-24-0), S32826 (CAS#1096770-84-1), PF-8380 (CAS#1144035-53-9), sphingosine kinase-1 inhibitor PF-543, Akt inhibitor X (CAS#925681-41-0), MK-2206 2HCl (CAS#1032350-13-2, 1032349-93-1 (free base), 1032349-77-1 (HCl)), Perifosine (CAS#157716-52-4), and mixtures and analogs thereof, wherein the composition comprises the agent in or on a cotton pledget, in a collagen shield saturated with the agent, or in an agent-impregnated contact lens.

2. A composition comprising an agent that inhibits the function of Yes-associated protein (YAP) transcriptional co-activator/transcriptional co-activator with PDZ binding motif (TAZ) formulated for ophthalmic administration, wherein the composition is formulated for administration to the eye via a route selected from the group consisting of topical, application to the eyelids, application to the conjunctival sac and intravitreous injection, wherein the composition is formulated in a form selected from the group consisting of a viscous solution, a suspension, an ointment, a small pellet to be placed under the eyelids, and a fine powder, wherein the agent is selected from the group consisting of dobutamine (CAS#34368-04-2), HSP90 inhibiting geldanamycin analogue 17-DMAG (CAS#467214-21-7), HSP90 inhibiting geldanamycin analogue 17-AAG (CAS#75747-14-7), HSP90 inhibitor STA-9090 (CAS#: 888216-25-9), HSP90 inhibitor NVP-HSP990 (CAS#934343-74-5), porphyrin family member verteporfin (CAS#129497-78-5), Ki16425 (CAS#355025-24-0), S32826 (CAS#1096770-84-1), PF-8380 (CAS#1144035-53-9), sphingosine kinase-1 inhibitor PF-543, Akt inhibitor X (CAS#925681-41-0), MK-2206 2HCl (CAS#1032350-13-2, 1032349-93-1 (free base), 1032349-77-1 (HCl)), Perifosine (CAS#157716-52-4), and mixtures and analogs thereof, wherein the compositon further comprises an agent that disrupts the cytoskeleton of a trabecular meshwork cell.

3. The composition of claim 2, wherein the agent that disrupts the cytoskeleton is selected from the group consisting of an agent that disrupts intermediate filaments; an agent that disrupts microtubules; an agent that disrupts actin polymerization, and mixtures thereof.

4. The composition of claim 3, wherein the agent that disrupts microtubules is selected from the group consisting of colchicine, colecemid, vinblastine, vincristine, vinorelbine, vindesine, podophyllotoxin, capecotobine, nocodazole, tryprostatin A, rhizoxin, vinflunine, epothilones, ixabepilone, methyl benzimidazol-2-yl-carbamate, estramustine sodium phosphate, paclitaxel, docetaxil, colchitaxel, and indibulin, and mixtures thereof.

5. The composition of claim 3, wherein the agent that disrupts actin polymerization is selected from the group consisting of Cytochalasin A, Cytochalasin B, Cytochalasin C, Cytochalasin D, Cytochalasin E, Cytochalasin F, Cytochalasin G, Cytochalasin H, Cytochalasin I, Cytochalasin J, latrunculin A, latrunculin B, Swinholide A, Misakinolide A, Bistheonelide A, Scytophycin A, Scytophycin B, Scytophycin D, Scytophycin E, 19-0-Demethylscytophycin C, 6 Hydroxyscytophycin B, 6-Hydroxy-7-o-methylscytophycin E, tolytoxin, Mycalolide A, Mycalolide B, Mycalolide C, secomycalolide A and 30-hydroxymycalolide A, Halichondramide, (19Z)-halichondramide, kabiramides B, kabiramides C, kabiramides D, kabiramides G, kabiramides J, kabiramides K, ulapualide A, jaspamide, Dihydrohalichondramide, Aplyronine A, Aplyronine B, Aplyronine C, Pectenotoxin 2, Pectenotoxin 6, Migrastatin, cucurbitane-type tritepenes B&E, olivetoric acid, chivosazole A, chivosazole F, desmethoxymajusculamide C, rho kinase inhibitors, blebbistatin and mixtures thereof.

* * * * *